(12) United States Patent
Arai et al.

(10) Patent No.: US 12,064,276 B2
(45) Date of Patent: Aug. 20, 2024

(54) PANORAMIC X-RAY IMAGING APPARATUS

(71) Applicants: NIHON UNIVERSITY, Tokyo (JP); J. MORITA MANUFACTURING CORPORATION, Kyoto (JP)

(72) Inventors: Yoshinori Arai, Chiyoda-ku (JP); Hideki Yoshikawa, Kyoto (JP)

(73) Assignees: NIHON UNIVERSITY, Tokyo (JP); J. MORITA MANUFACTURING CORPORATION, Kyoto (JP)

( * ) Notice: Subject to any disclaimer, the term of this patent is extended or adjusted under 35 U.S.C. 154(b) by 293 days.

(21) Appl. No.: 17/661,965

(22) Filed: May 4, 2022

(65) Prior Publication Data

US 2022/0361832 A1 Nov. 17, 2022

(30) Foreign Application Priority Data

May 11, 2021 (JP) .................. 2021-080277

(51) Int. Cl.
*A61B 6/14* (2006.01)
*A61B 6/00* (2006.01)
(Continued)

(52) U.S. Cl.
CPC .......... *A61B 6/4441* (2013.01); *A61B 6/4028* (2013.01); *A61B 6/42* (2013.01); *A61B 6/4452* (2013.01)

(58) Field of Classification Search
CPC ....... A61B 6/51; A61B 6/4441; A61B 6/4452; A61B 6/4458; A61B 6/512; A61B 1/24;
(Continued)

(56) References Cited

U.S. PATENT DOCUMENTS

2017/0311910 A1* 11/2017 Inglese .................. H04N 5/32
2020/0315555 A1 10/2020 Sugihara et al.
2021/0093282 A1 4/2021 Sadakane et al.

FOREIGN PATENT DOCUMENTS

DE 20 2020 104 200 U1 12/2020
EP 3 586 751 A1 1/2020
(Continued)

OTHER PUBLICATIONS

Extended European Search Report issued Aug. 26, 2022 in European Patent Application No. 22172285.3, 6 pages.

*Primary Examiner* — Don K Wong
(74) *Attorney, Agent, or Firm* — Oblon, McClelland, Maier & Neustadt, L.L.P.

(57) ABSTRACT

A panoramic X-ray imaging apparatus includes: an X-ray generating unit; an X-ray detecting unit; a support that supports the X-ray generating unit and the X-ray detecting unit; a drive mechanism that turns at least the X-ray generating unit and the X-ray detecting unit by driving the support; a displacement mechanism that adds movement including a displacement component in a direction different from the turning to the X-ray detecting unit; a subject holding unit that holds an imaging subject; a turning controller that controls the turning by a drive mechanism and the displacement mechanism. The turning controller controls the drive mechanism and the displacement mechanism so as to add the movement avoiding the contact with the shoulder of the imaging subject during the turning of the X-ray generating unit and the X-ray detecting unit by the drive mechanism during the panoramic X-ray imaging.

12 Claims, 27 Drawing Sheets

(51) Int. Cl.
*A61B 6/40* (2024.01)
*A61B 6/42* (2024.01)

(58) Field of Classification Search
CPC .. A61B 6/02; A61B 6/027; A61B 6/03; A61B 6/04; A61B 6/08
See application file for complete search history.

(56) References Cited

FOREIGN PATENT DOCUMENTS

| | | |
|---|---|---|
| EP | 3 733 074 A1 | 11/2020 |
| JP | 2001-346796 A | 12/2001 |
| JP | 2009-136363 A | 6/2009 |
| KR | 10-2010-0106879 A | 10/2010 |

\* cited by examiner

F I G. 1
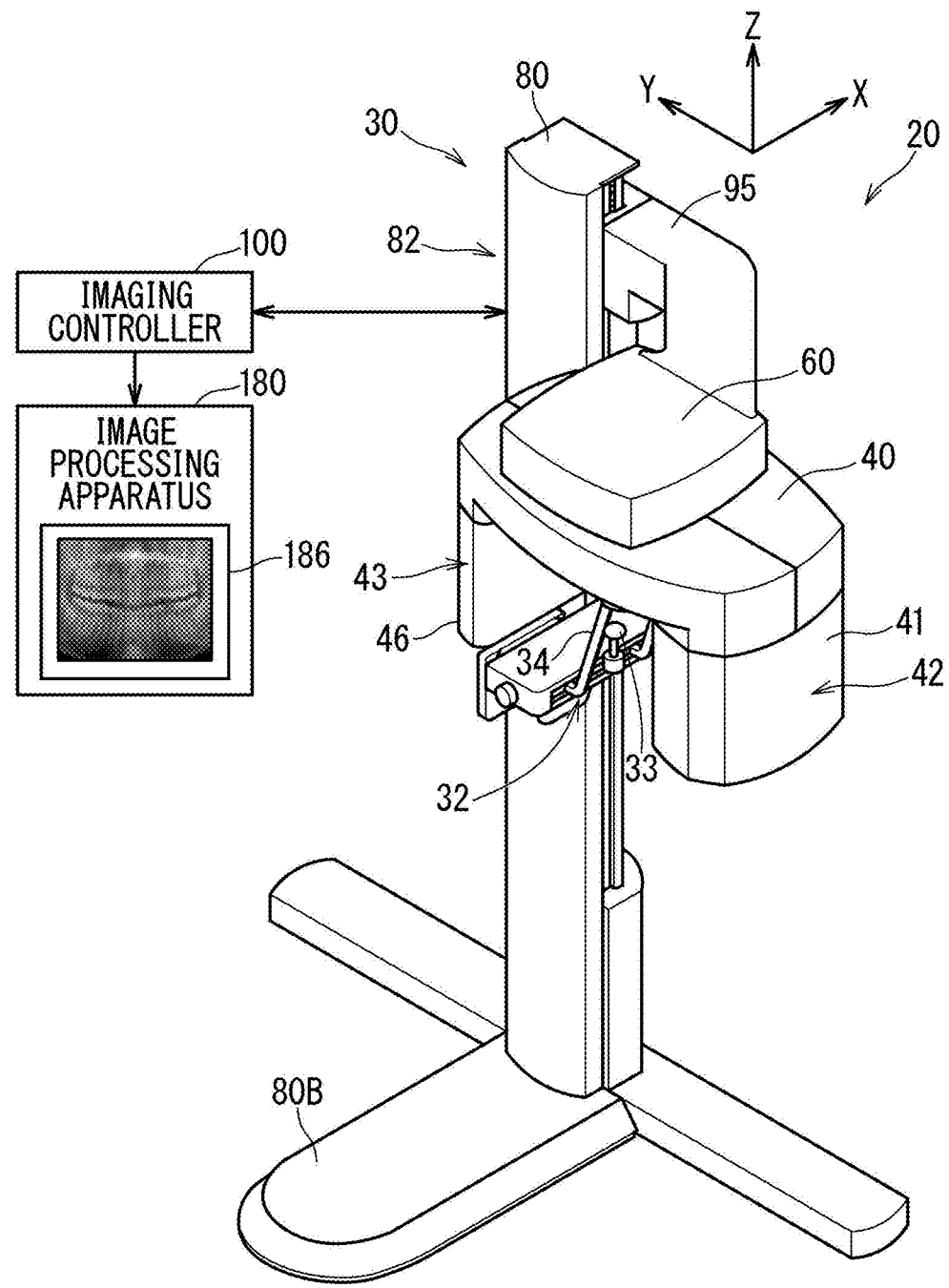

F I G. 4
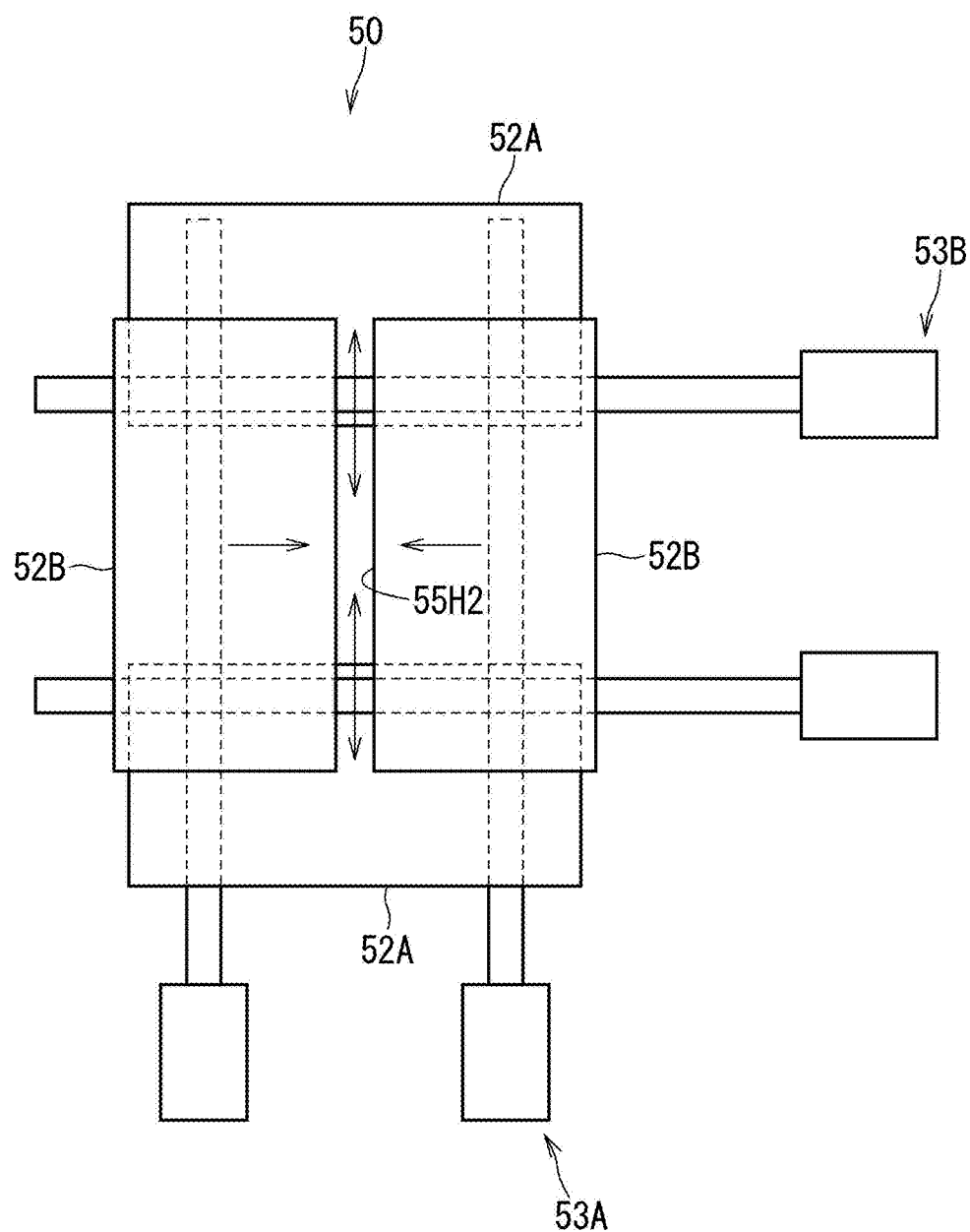

F I G. 10
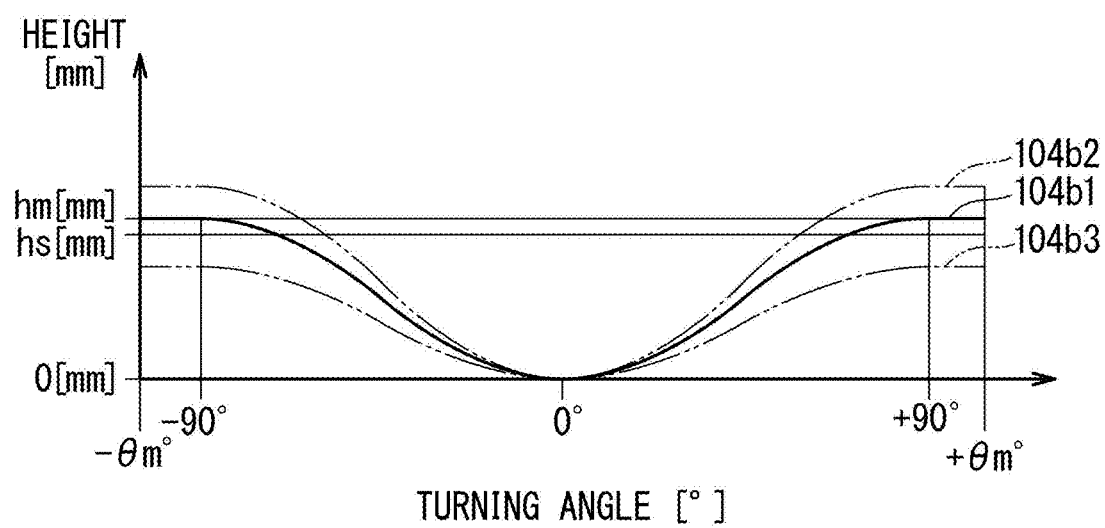

PANORAMIC X-RAY IMAGING APPARATUS

BACKGROUND OF THE INVENTION

Field of the Invention

The present invention relates to a technique that performs panoramic X-ray imaging by rotating an X-ray generator and an X-ray detector around a subject.

Description of the Background Art

Japanese Patent Application Laid-Open No. 2009-136363 discloses that presence or absence of a possibility of a shoulder hitting of a patient is detected by a shoulder hitting detection means such as a camera, and a warning of shoulder hitting is issued when the shoulder hitting is detected.

SUMMARY

Here, it is required to improve resolution (fine expressive power of an imaging target region) of a panoramic image. The resolution of the panoramic image is improved as the X-ray detector is closer to an imaging target region.

According to Japanese Patent Application Laid-Open No. 2009-136363, a posture of the patient is corrected when the warning of the shoulder hitting is issued. However, correcting the posture of the patient does not lead to bringing the X-ray detector close to the imaging target region. For this reason, it is difficult to improve the resolution of the panoramic image.

An object of the present disclosure is to improve the resolution of the panoramic image while preventing an X-ray detecting unit including the X-ray detector from hitting the shoulder.

In order to solve the above problem, a panoramic X-ray imaging apparatus includes: a first housing that accommodates an X-ray generator; a second housing that accommodates an X-ray detector; a support that supports the first housing and the second housing such that the X-ray generator and the X-ray detector are opposite to each other; a shaft located between the X-ray generator and the X-ray detector; a first motor that turns the support around the shaft; a second motor that provides power to add movement including a displacement component in a direction different from the turning to the second housing; a subject holder that holds an imaging subject; and a processor that controls drive of the support by the first motor and addition of movement to the second housing by the second motor such that panoramic X-ray imaging is performed by turning around a head of the imaging subject while the head of the imaging subject held by the subject holder is positioned between the X-ray generator and the X-ray detector. The processor controls the first motor and the second motor so as to add the movement avoiding the contact with the shoulder of the imaging subject to the second housing during the turning of the X-ray generator and the X-ray detector by the first motor during the panoramic X-ray imaging.

The resolution of the panoramic image can be improved while the X-ray detecting unit including the X-ray detecting unit is prevented from hitting the shoulder.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a perspective view illustrating an X-ray imaging apparatus according to a first embodiment;

FIG. 4 is an explanatory view illustrating the X-ray beam shape adjuster;

FIG. 10 is a view illustrating an example of a vertical displacement pattern;

DESCRIPTION OF THE PREFERRED EMBODIMENTS

First Preferred Embodiment

A panoramic X-ray imaging apparatus according to a first embodiment will be described below.

<Entire Configuration>

Figure 2:
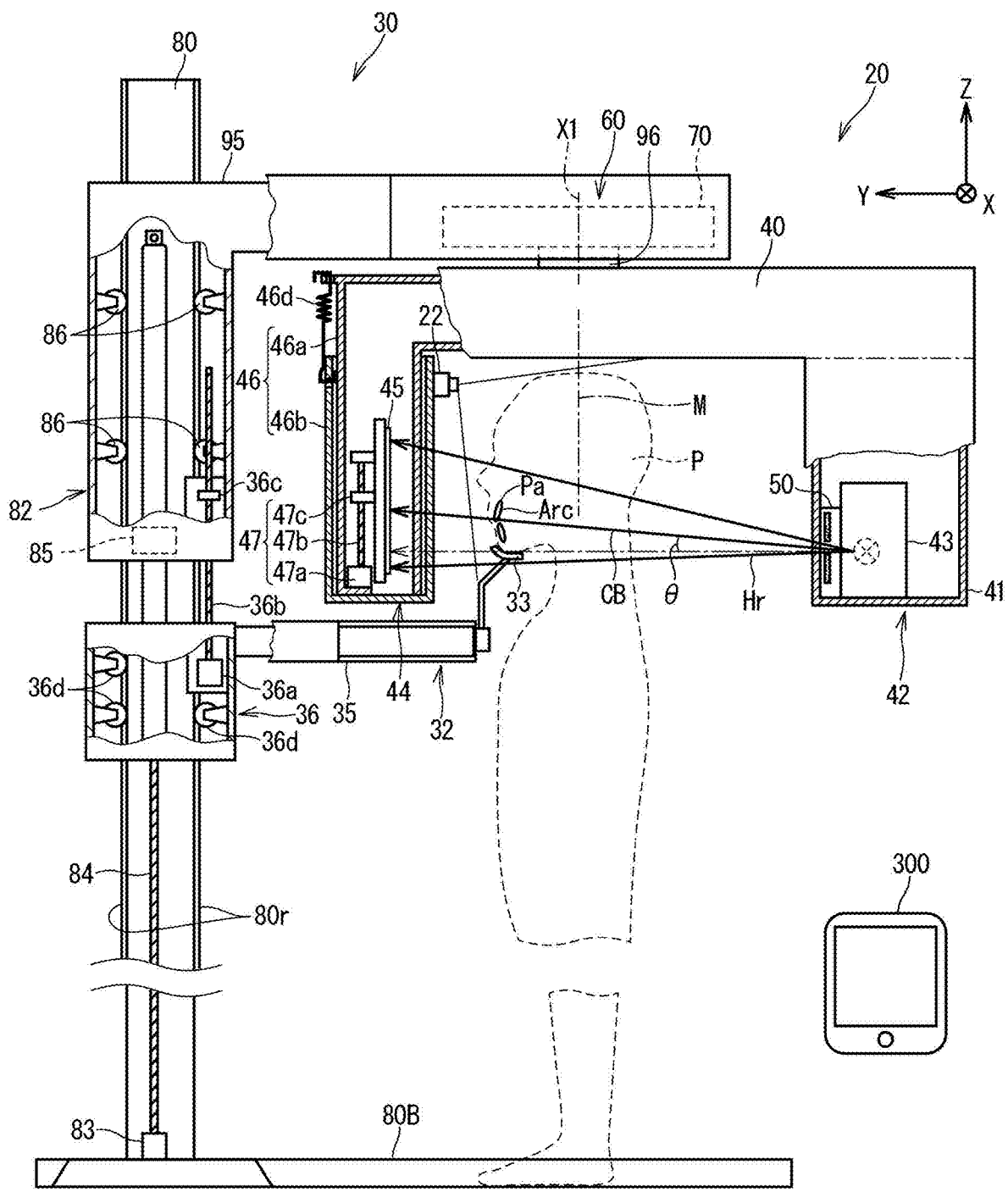
FIG. 2 is a partially sectional side view illustrating the X-ray imaging apparatus of the first embodiment.

An overall configuration of an X-ray imaging apparatus that is an example of the panoramic X-ray imaging apparatus will be described. FIG. 1 is a perspective view illustrating an X-ray imaging apparatus 20. In FIG. 1, a part of the configuration is indicated by a functional block. FIG. 2 is a partially sectional side view illustrating the X-ray imaging apparatus 20.

A direction is defined for the sake of convenience. An XYZ-orthogonal coordinate system is an orthogonal coordinate system defined in a three-dimensional space in which an imaging main body 30 is installed. A direction parallel to an axial direction of a mechanical turning axis X1 is set to a Z-axis direction. In the first preferred embodiment, the direction parallel to the axial direction of the mechanical turning axis X1 and a moving direction of a vertical drive unit 82 are matched with the Z-axis direction. A direction orthogonal to the Z-axis direction is set to a Y-axis direction, and a direction orthogonal to the Z-axis direction and the Y-axis direction is set to an X-axis direction. A front-rear direction of a head P of an imaging subject M held by a subject holding unit 32 is set to the Y-axis direction, and a right and left direction of the head P is set to the X-axis direction. In the present invention, sometimes the Z-axis direction is referred to as a Z direction, the Y-axis direction is referred to as a Y direction, and the X-axis direction is referred to as an X direction. As for a line-of-sight direction, for example, a line-of-sight direction viewed from the −Z side to a +Z side is referred to as a +Z direction view, a line-of-sight direction viewed from a −o (o is any of X, Z, Y) side to a +o side or a line-of-sight direction parallel to the line-of-sight direction is defined as a "+o direction view", and a line-of-sight direction viewed from the +o side to the −o side or a line-of-sight direction parallel to the line-of-sight direction is defined as a "−o direction view". When it is simply described as "in a o direction view", it may be in the +o direction view or the −o direction view. A two-dimensional surface extending in the X direction and the Y direction may be referred to as an XY-plane, and a two-dimensional surface extending in the o direction and the Δ (Δ is any one of X, Z, Y) direction may be referred to as a "oΔ-plane".

The direction from the head P toward a base 80B, namely, a lower side is set to the −Z side, and the direction away from the base 80B from the head P, namely, an upper side is set to the +Z side. A front side of the head P is set to a +Y side, and a rear side is set to a −Y side. A right side of the head P viewed from a face side is set to a +X side, and a left side is set to a −X side. FIGS. 1 and 2 illustrate each axial direction.

For example, the X-ray imaging apparatus 20 includes the imaging main body 30 and an X-ray image processing apparatus 180 (also simply referred to as an image processing apparatus 180). The imaging main body 30 is configured to be able to execute the panoramic X-ray imaging. For example, the imaging main body 30 may be configured to be capable of performing at least one of simple transmission X-ray imaging, X-ray computed tomography (CT) imaging, and cephalogram imaging in addition to the panoramic X-ray. The imaging main body 30 performs the X-ray imaging such as the panoramic X-ray imaging to collect X-ray imaging data (also referred to as projection data). The collected X-ray imaging data is processed by the X-ray image processing apparatus 180, and generates various X-ray images (specifically, an X-ray CT imaging image, a panoramic imaging image, a cephalographic imaging image, and the like). In this example, the X-ray image processing apparatus 180 processes the X-ray imaging data collected by the panoramic X-ray imaging processing to generate the panoramic X-ray image. The panoramic X-ray image is an X-ray image in which a dental arch is continuously expressed by an X-ray transmission image in the direction orthogonal to the dental arch. Depending on a part of the dental arch, orthogonality may be intentionally avoided to some extent in order to avoid another hard tissue such as a jawbone. In such the panoramic X-ray image, adjacent teeth are represented so as not to overlap each other as little as possible. The X-ray imaging apparatus 20 may be configured as an apparatus that collects the X-ray imaging data, and may be configured that the X-ray image processing apparatus 180 is omitted. The X-ray imaging apparatus 20 may be configured to include only some functions of the X-ray image processing apparatus 180.

The imaging main body 30 includes an X-ray generating unit 42, an X-ray detecting unit 44, a turning arm 40 that is an example of the supporting unit, a drive mechanism 60, a vertical drive unit 82 that is an example of the displacement mechanism, and an imaging controller 100.

The X-ray generating unit 42 includes an X-ray generator 43 that generates an X-ray (X-ray beam). The X-ray detecting unit 44 includes an X-ray detector 45 that detects the X-ray. The turning arm 40 supports the X-ray generating unit 42 and the X-ray detecting unit 44 such that the X-ray generating unit 42 and the X-ray detecting unit 44 are opposite to each other. The drive mechanism 60 drives the turning arm 40. For example, the drive is turning drive. The drive mechanism 60 drives the turning arm 40 to turn at least the X-ray generating unit 42 and the X-ray detecting unit 44. The vertical drive unit 82 is a mechanism that adds movement including a displacement component in a direction different from the turning by the drive mechanism 60 to the X-ray detecting unit 44. For example, the displacement component to be added is a direction parallel to a turning axis X1 by the drive mechanism 60, namely, a vertical direction (Z-axis direction). During the panoramic X-ray imaging, the imaging subject M is held at a fixed position by the subject holding unit 32. The subject holding unit 32 is preferably fixed and positioned so as to restrict the movement of the head P of the imaging subject during the X-ray imaging. In a state where the imaging subject M is held by the subject holding unit 32, and in a state where the head P of the imaging subject M held by the subject holding unit 32 is positioned between the X-ray generating unit 42 and the X-ray detecting unit 44, the drive of the turning arm 40 by the drive mechanism 60 and the addition of the movement to the X-ray detecting unit 44 by the vertical drive unit 82 are controlled such that the X-ray generating unit 42 and the X-ray detecting unit 44 turn around the head P to perform the panoramic X-ray imaging under the control of the imaging controller 100. The movement of the X-ray detecting unit 44 added by the imaging controller 100 is such the movement that contact with a shoulder S of the imaging subject M can be avoided during the turning of the X-ray generating unit 42 and the X-ray detecting unit 44.

The configuration of each unit will be described more specifically.

The turning arm 40 is formed in a shape elongated in one direction. For example, the turning arm 40 is provided along a horizontal direction. The X-ray generating unit 42 is provided in a hanging manner at one end of the turning arm 40, and the X-ray detecting unit 44 is provided in a hanging manner at the other end of the turning arm 40. Thus, the X-ray generating unit 42 and the X-ray detecting unit 44 are opposite to each other while the head P can be disposed between the X-ray generating unit 42 and the X-ray detecting unit 44. In this state, the X-ray generating unit 42 irradiates the head P with an X-ray beam. The X-ray detecting unit 44 receives and detects the X-ray beam transmitted through the head P.

The X-ray generating unit 42 includes an X-ray generator 43 and the X-ray beam shape adjuster 50. In the preferred embodiment, the X-ray generating unit 42 further includes a housing 41 that accommodates the X-ray generator 43 and the X-ray beam shape adjuster 50. The housing 41 is an example of a first housing. The housing 41 includes a bottom portion and a peripheral wall portion surrounding a space above the bottom portion. The housing 41 is supported by one end of the turning arm 40 so as to protrude downward.

The X-ray generator 43 includes an X-ray tube that is an X-ray source emitting the X-ray. Intensity (output intensity) of the X-ray beam emitted from the X-ray generator 43 can be controlled by changing voltage and/or current supplied to the X-ray tube. The control (in particular, the control of a voltage amount and/or a current amount) of the X-ray generator 43 is performed by an irradiation controller 102*d* of the imaging controller 100.

The X-ray beam shape adjuster 50 regulates spread of the X-ray beam emitted from the X-ray generator 43, and adjusts the X-ray beam into a shape according to an imaging purpose. That is, the X-ray beam shape adjuster 50 controls an X-ray irradiation range with respect to the imaging subject M (subject). The X-ray beam shape adjuster 50 is controlled by the irradiation controller 102*d*.

Figure 3:
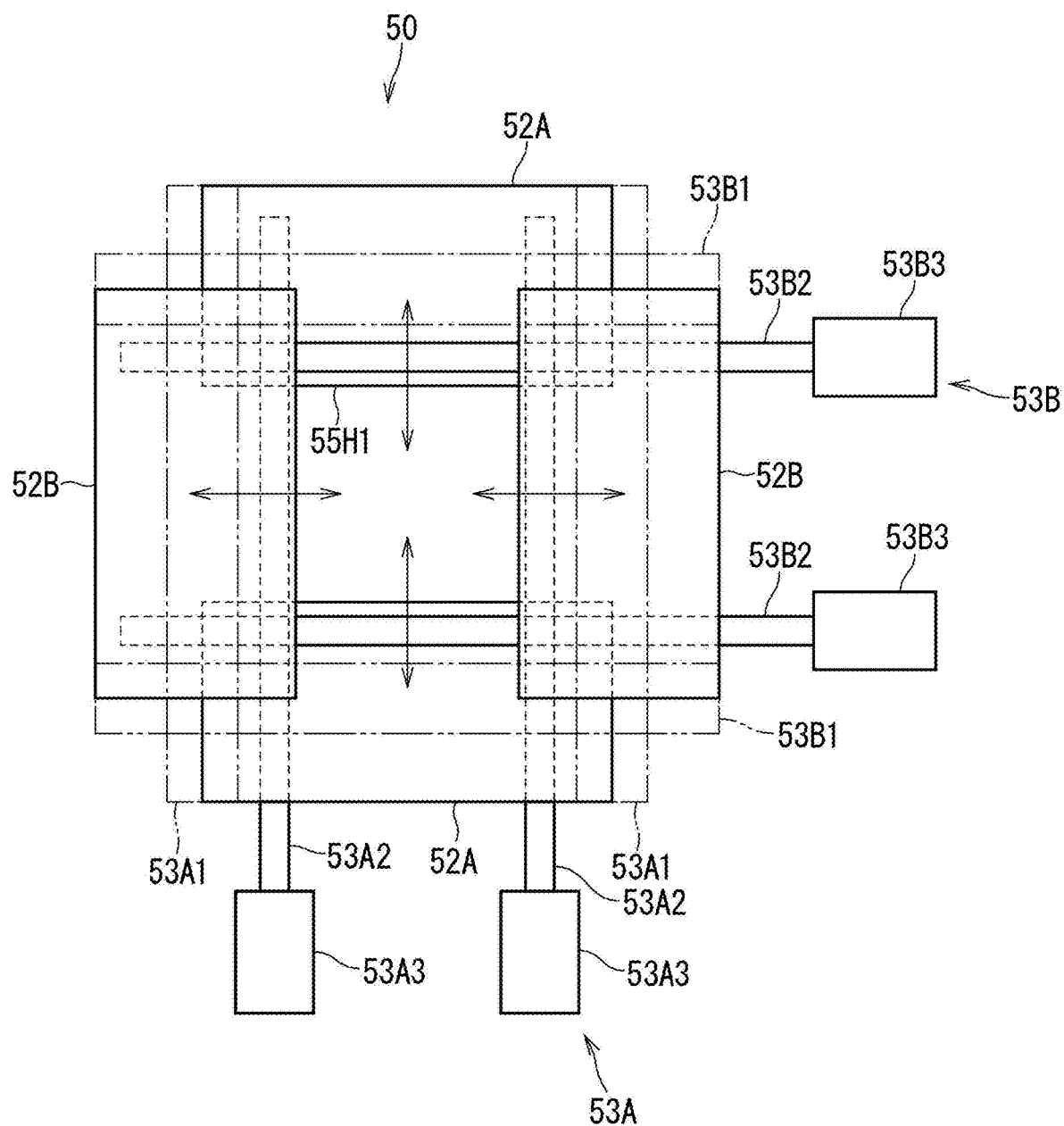
FIG. 3 is an explanatory view illustrating an X-ray beam shape adjuster.

FIGS. 3 and 4 are views illustrating a configuration example of the X-ray beam shape adjuster 50. The X-ray beam shape adjuster 50 includes two shielding members 52A, a shielding member drive unit 53A that drives to open and close the two shielding members 52A, two shielding members 52B, and a shielding member drive unit 53B that drives to open and close the two shielding members 52B. In FIGS. 3 and 4, portions (a motor, a shaft, and the like) that drive the shielding members 52A, 52B and the shielding members 52A, 52B are indicated by a solid line or a hidden line (broken line), and guides 53A1, 53B1 are indicated by a virtual line (two-dot chain line).

The shielding members 52A, 52B are made of a material (such as lead) absorbing the X-rays, and are formed into a rectangular plate shape.

In the four shielding members 52A, 52B, the two shielding members 52A are provided at upper and lower positions on a front side of an emission port of the X-ray generator 43. The sides on the opposite sides in the two shielding members 52A are along the horizontal direction.

The shielding member drive unit 53A drives the two shielding members 52A to approach and separate along a vertical direction. For example, the shielding member drive unit 53A includes two guides 53A1, two shafts 53A2, and two motors 53A3 that drive the two shafts 53A2. The shielding member 52A and the shaft 53A2 can be configured such that, for example, a screw provided on an outer periphery of the shaft 53A2 is screwed into a screw groove provided in the shielding member 52A to displace the shielding member 52A by rotational drive of the shaft 53A2. Each individual drive control may be performed such that one of the shielding members 52A is driven by one of the shafts 53A2 while the other of the shielding members 52A is driven by the other of the shafts 53A2.

A pair of guides 53A1 supports both ends of each of the two shielding members 52A so as to be movable in the vertical direction.

The two shielding members 52A are individually moved and driven in the vertical direction.

The other two shielding members 52B of the four shielding members 52A, 52B are provided at right and left positions on the front side of the emission port of the X-ray generator 43 at positions different from the two shielding members 52A in an emission direction of the X-ray from the X-ray generator 43. The sides on the opposite sides in the two shielding members 52B are along the vertical direction.

The shielding member drive unit 53B drives the two shielding members 52B to approach and separate along the left-right direction. The shielding member drive unit 53B and the shielding member 52B may have the same structure in which only the directions of the drive and the movement are different from those of the shielding member drive unit 53A and the shielding member 52A, and the directions of the drive and the movement may be different by 90° around the axis of the X-ray irradiation. Then, the two shielding members 52B are individually moved and driven in the left-right direction by the clockwise or counterclockwise rotational drive of the two motors 53B3.

A linear motor mechanism, a rack-and-pinion mechanism, a mechanism using a belt and a pulley, or the like may be used as the shielding member drive units 53A, 53B.

In this example, the shape of the X-ray beam, the position to be the irradiation destination, and the like are adjusted according to openings 55H1, 55H2 formed by the two opposing upper and lower inner sides of the two shielding members 52A and the two opposing left and right inner sides of the two shielding members 52B.

For example, a rectangular opening 55H1 (see FIG. 3) is formed in the state where two opposing upper and lower inner sides of the two shielding members 52A are largely open and two opposing left and right inner sides of the two shielding members 52B are largely open. The X-ray beam emitted from the X-ray generator 43 is shaped into an X-ray cone beam spreading in a regular quadrangular pyramidal shape by passing through the rectangular shape, for example, the truncated square-shaped opening 55H1. For example, the X-ray cone beam is used for CT imaging.

Furthermore, for example, the elongated opening 55H2 is formed (see FIG. 4) in the state where two opposing upper and lower inner sides of the two shielding members 52A are largely open and two opposing left and right inner sides of the two shielding members 52B are slightly open. The X-ray beam emitted from the X-ray generator 43 is shaped into an X-ray narrow beam spreading in a vertically elongated truncated pyramidal shape by passing through the opening 55H2 having a vertically elongated slit shape. For example, the X-ray narrow beam is used for the panoramic X-ray imaging.

The two shielding members 52B is moved in the same direction, for example, the right direction while the shape of the opening 55H2 is maintained, so that an irradiation destination of the X-ray narrow beam can be scanned from the left direction to the right direction. In addition, the two shielding members 52B is moved in the same direction, for example, the upward direction while the shape of the opening 55H2 is maintained, so that the irradiation destination of the X-ray narrow beam can be moved from the downward direction to the upward direction.

For example, during the panoramic X-ray imaging, the X-ray beam shape adjuster 50 can shape the X-ray beam emitted from the X-ray generator 43 into the X-ray narrow beam in which a center beam CB that is the center of the X-ray beam is incident upward from obliquely downward with respect to a body axis (vertical direction) of the imaging subject M, the X-ray narrow beam having a length in the direction of the body axis (see FIG. 2). For example, an angle θ of the center beam CB with respect to a horizontal direction Hr may be 4 degrees to 8 degrees. In this manner, the X-ray beam is incident on the imaging subject M from the lower side to the upper side with respect to the horizontal direction, whereby shade and shadow of an obstacle due to a hard palate, a mandibular angle, a spine, and the like are reduced on the panoramic image. In this manner, the incidence of the X-ray beam on the imaging subject M from the obliquely lower side to the obliquely upper side may be referred to as oblique launch irradiation.

When the panoramic X-ray imaging is performed, it is not necessary that the X-ray beam is incident on the imaging subject M from the lower side to the upper side with respect to the horizontal direction. For example, the X-ray beam may be incident on the imaging subject M along the horizontal direction.

The X-ray beam shape adjuster may have another configuration. For example, the X-ray beam shape adjuster may include two shielding members formed in an L-shaped plate shape, and the opening may be formed by a combination of edges configuring the inner corner portions of the two shielding members. In this case, the two shielding members are preferably movable in the vertical direction and the left-right direction by an XY-table mechanism or the like that is moved and driven in two orthogonal directions. Similarly to the above, the shape of the opening is adjusted by moving and driving the tow shielding members using the mechanism. The X-ray beam shape adjuster may include a single shielding member in which one or a plurality of openings are formed. In this case, when the shielding member is moved and driven by a linear movement mechanism, the position of the opening is moved, and the irradiation destination of the X-ray beam can be moved. The plurality of openings can be selectively opposite to the emission port of the X-ray generating unit 42.

As illustrated in FIGS. 1 and 2, the X-ray detecting unit 44 includes the X-ray detector 45 and an X-ray detector vertical movement drive unit 47. The X-ray detector 45 detects the X-ray beam emitted from the X-ray generating unit 42. The X-ray detector 45 may be configured of a flat panel detector (FPD) including a detection surface spreading flat or X-ray image intensifier tube (an image intensifier (I.I.)).

The plurality of detecting elements arranged on the detection surface of the X-ray detector 45 convert the intensity of the incident X-ray into an electric signal. The electric signal is input to the imaging controller 100 and the image processing apparatus 180 as an output signal, and the X-ray image is generated based on the output signal.

In the first preferred embodiment, the X-ray detecting unit 44 includes a housing 46 that accommodates the X-ray detector 45. The X-ray detector 45 is provided in the housing 46 in a posture in which a detection surface faces the X-ray generating unit 42. The detection surface of the X-ray detector 45 is irradiated with the X-ray beam emitted from the X-ray generating unit 42. The housing 46 is supported by the other end of turning arm 40 while accommodating the X-ray detector 45 and the X-ray detector vertical movement drive unit 47. The housing 46 is an example of a second housing.

The X-ray detector vertical movement drive unit 47 moves the X-ray detector 45 in the vertical direction (Z-axis direction) with respect to the turning arm 40. The X-ray detector vertical movement drive unit 47 includes a motor 47a as a second motor, a ball screw 47b, and a nut 47c. The motor 47a rotates the ball screw 47b extending in the Z-axis direction about the Z-axis. The nut 47c is screwed to the ball screw 47b, and is attached to a back surface of the X-ray detector 45 opposite to the detection surface so as not to rotate with respect to the X-ray detector 45. The X-ray detector 45 may be guided by a rail (not illustrated) so as to move in the Z-axis direction in a posture facing the side of the X-ray generating unit 42.

The motor 47a is controlled by an X-ray detecting unit drive controller 102e. The motor 47a rotates the ball screw 47b based on the control signal from the X-ray detecting unit drive controller 102e, whereby the nut 47c and the X-ray detector 45 are moved in the Z-axis direction.

The housing 46 includes a cylindrical unit 46a formed in a cylindrical shape that is opened downward while extending downward from the other end of the turning arm 40 and an outer housing 46b that covers the outside of the cylindrical unit 46a while being opened upward.

The motor 47a is fixed to the cylindrical unit 46a. The outer housing 46b is biased upward by a spring 46d provided to connect the turning arm 40 or the cylindrical unit 46a and the outer housing 46b in the vertical direction. The lower end of the X-ray detector 45 can abut on the inside of the bottom surface of the outer housing 46b. When the X-ray detector vertical movement drive unit 47 moves the X-ray detector 45 downward, the X-ray detector 45 abuts on the bottom surface of the outer housing 46b to push down the outer housing 46b. At this time, the spring 46d elastically extends, and elastic restoring force is accumulated in the spring 46d. When the X-ray detector vertical movement drive unit 47 moves the X-ray detector 45 upward, the outer housing 46b is pulled upward by the elastic restoring force of the spring 46d. Consequently, the outer housing 46b is raised while abutting on the raising X-ray detector 45 so as to follow the X-ray detector 45.

The configuration in which the X-ray detecting unit 44 is moved up and down with respect to the turning arm 40 may be omitted.

The outer housing 46b moves up and down with respect to the inside cylindrical unit 46a according to a height position of the X-ray detector 45, whereby the housing 46 expands and contracts in the vertical direction. The X-ray detector 45 in which the position in the height direction changes can be properly protected by the expansion and contraction of the housing 46. The housing 46 is disposed at a position as high as possible by the spring 46d, so that the housing 46 is hardly in contact with the imaging subject M during the X-ray imaging. That is, the cylindrical unit 46a, the outer housing 46b, the spring 46d, the X-ray detector vertical movement drive unit 47, and the X-ray detector 45 form an X-ray detecting unit expansion and contraction mechanism that guides and drives the movement in the elevation direction of the bottom of the X-ray detecting unit 44 and the X-ray detector 45 itself on the bottom side to expand and contract the X-ray detecting unit 44 in the Z direction. The X-ray detecting unit expansion and contraction mechanism can also function as an X-ray detecting unit bottom position changing mechanism that changes the position in the Z direction of the bottom of the X-ray detecting unit 44 and the X-ray detector 45 itself on the bottom side with respect to the turning arm 40.

In the first preferred embodiment, when the X-ray detector 45 is disposed at the highest position (that is, when the outer housing 46b is disposed at the highest position), the lowermost end (that is, the lowermost end of the housing 46) of the outer housing 46b may be configured so as to be located lower than the lowermost end of the housing 41 of the X-ray generating unit 42. That is, in this case, regardless of the height of the X-ray detector 45, the lowermost end of the housing 41 is always located lower than the lowermost end of the housing 46.

When the X-ray beam is obliquely launch-irradiated, the X-ray detector 45 can be positioned upward according to the position of the irradiation destination. Consequently, the lower end of outer housing 46b can be rotated at the position as high as possible when the panoramic X-ray imaging is performed by the oblique launch irradiation. It is not essential to vertically move the X-ray detecting unit 44 and the housing 46 according to the irradiation destination of the X-ray beam. For example, when the detection surface of the X-ray detecting unit 44 has a sufficiently wide size to detect the X-ray beam regardless of the irradiation destination of the X-ray beam, the X-ray detecting unit 44 may not move up and down. In addition, as a matter of course, when the irradiation direction of the X-ray beam is not changed vertically, the X-ray detecting unit 44 and the housing 46 may not be moved vertically.

The turning arm 40 supporting the X-ray generating unit 42 and the X-ray detecting unit 44 is supported by an upper frame 95 through the drive mechanism 60.

The upper frame 95 is supported by a post 80. The post 80 is supported in a standing state with respect to the floor by, for example, a base 80B extending in the horizontal direction with respect to the floor. In the first preferred embodiment, a proximal end of the upper frame 95 is supported by the post 80 in a cantilevered state, and the distal end of the upper frame 95 extends outward along the horizontal direction from the post 80. A turning shaft 96 extending in the Z-axis direction is provided at a distal end of the upper frame 95. The lower end of the turning shaft 96 is connected to an intermediate portion between the X-ray generating unit 42 and the X-ray detecting unit 44 in the turning arm 40. Consequently, the turning arm 40 is supported by the upper frame 95 in the hanging state through the turning shaft 96.

The drive mechanism 60 is an apparatus that drives the turning arm 40 such that the X-ray generating unit 42 and the X-ray detecting unit 44 turn around the head P of the imaging subject M. The drive mechanism 60 can drive the turning arm 40 so as to change at least the turning orbit of the X-ray detecting unit 44.

In the first preferred embodiment, the drive mechanism 60 includes a turning mechanism 62 and a turning axis moving mechanism 70 (hereinafter, sometimes simply referred to as the axis moving mechanism 70). The turning mechanism 62 turns the turning arm 40 around the axis of the turning shaft 96, namely, around the turning axis. The axis moving mechanism 70 moves the turning shaft 96 in a direction intersecting (in this case, orthogonal to) the axial direction of the turning shaft 96. The axis moving mechanism 70 is an example of the two-dimensional moving mechanism that moves the X-ray generating unit 42 and the X-ray detecting unit 44 in a two-dimensional direction (in the first referred embodiment, the horizontal plane) along the turning plane of the X-ray generating unit 42 and the X-ray detecting unit 44 by the turning mechanism 62.

Figure 6:
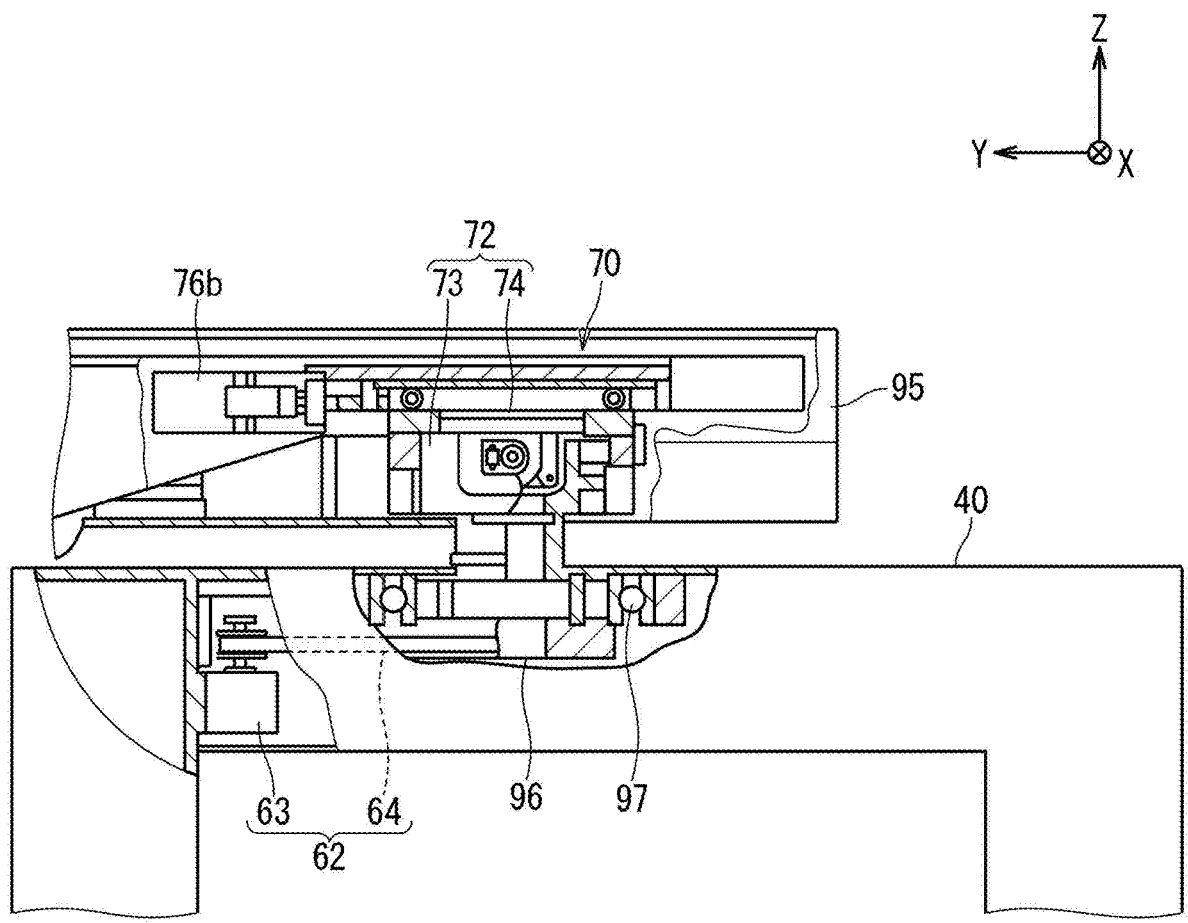
FIG. 6 is a partially broken front view illustrating the turning axis moving mechanism.

More specifically, as illustrated in FIG. 6, the turning arm 40 is rotatably supported around the central axis of the turning shaft 96 with respect to the lower end of the turning shaft 96. A bearing 97 may be interposed between the turning shaft 96 and the turning arm 40 such that the turning arm 40 can smoothly rotate with respect to the turning shaft 96.

The turning mechanism 62 is provided inside the turning arm 40. The turning mechanism 62 includes a turning motor 63 as a first motor. More specifically, the turning mechanism 62 includes the turning motor 63 fixed to the turning arm 40 and an endless annular belt 64. A rotation direction of the turning motor 63 is controlled by a support controller 102a. The endless annular belt 64 is wound around an annular member (such as a pulley) fixed to the shaft of the turning motor 63 and an annular member receiving drive force on the side of the turning arm 40 fixed to the lower end of the turning shaft 96. In this case, the turning shaft 96 is fixed so as not to rotate with respect to the upper frame 95. When rotational force is transmitted to the endless annular belt 64 by the drive of the turning motor 63, the turning motor 63 itself rotates in response to reaction from the endless annular belt 64, and the turning arm 40 having a fixed relationship with the turning motor 63 rotates. The endless annular belt 64 may be an annular chain. Instead of or in addition to the endless annular belt 64, one or a plurality of gears may be interposed between the turning motor 63 and the turning shaft 96. The turning motor 63 may be directly connected to the turning shaft 96.

The turning mechanism 62 may be provided in the upper frame 95. In this case, the turning shaft 96 and the turning arm 40 may be fixedly connected, and the turning shaft 96 rotatably supported with respect to the upper frame 95 may be rotated together with the turning arm 40.

A center axis X1 of the turning shaft 96 is located between the X-ray generating unit 42 on one end side of the turning arm 40 and the X-ray detecting unit 44 on the other end side of the turning arm 40. The turning mechanism 62 rotates the turning arm 40, so that the X-ray generating unit 42 and the X-ray detecting unit 44 can turn about the center axis X1 of the turning shaft 96.

In the first preferred embodiment, an imaging apparatus 22 is provided in the turning arm 40. The imaging apparatus 22 is provided at a position where the head P held by the subject holding unit 32 can be imaged. For example, the imaging apparatus 22 is a visible light camera. Here, the imaging apparatus 22 is supported on an upper portion of the housing 46 facing the X-ray generating unit 42 so as to face the X-ray generating unit 42. For example, an imaging range by the imaging apparatus 22 is set to a range including the head P and the shoulder S of the imaging subject M held by the subject holding unit 32. The imaging apparatus 22 may be omitted. A modification using the imaging apparatus 22 will be described later.

Figure 5:
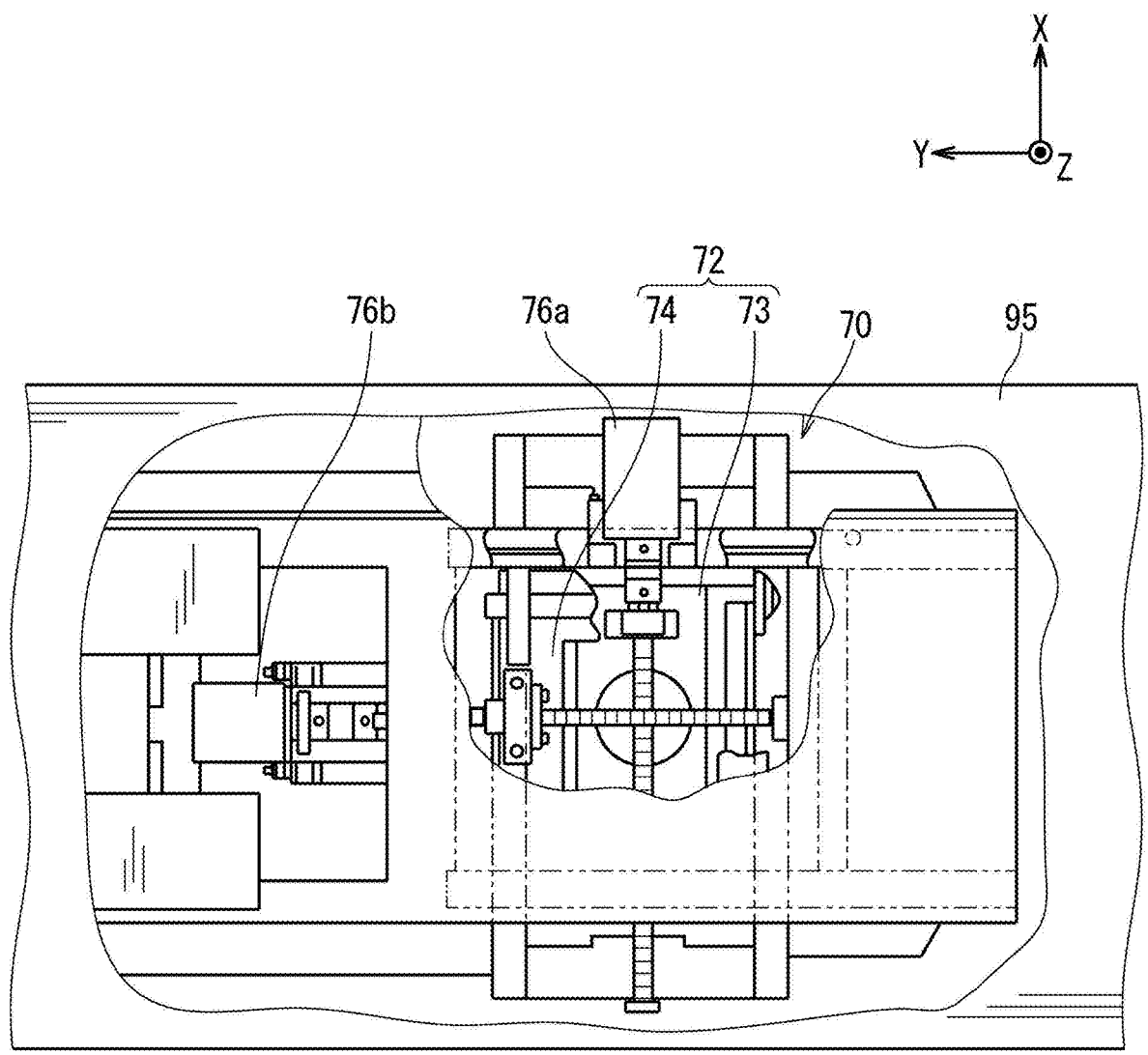
FIG. 5 is a partially broken plan view illustrating a turning axis moving mechanism.

As illustrated in FIGS. 5 and 6, the axis moving mechanism 70 is a mechanism that moves the turning shaft 96 in the direction intersecting (in this case, orthogonal to) the center axis of the turning shaft 96, and in the first preferred embodiment, the turning axis moving mechanism 70 is an XY-direction moving mechanism that moves the turning shaft 96 in the X-axis direction and the Y-axis direction. For example, the axis moving mechanism 70 includes an XY-table 72 and drive motors 76a, 76b. For example, the axis moving mechanism 70 is provided in the upper frame 95.

The XY-table 72 includes an X direction movable table 73 and a Y direction movable table 74. The X direction movable table 73 is provided so as to be movable along the X direction, and moves the turning arm 40 in a lateral direction (X-axis direction). The Y direction movable table 74 is provided so as to be movable along the Y direction, and moves the turning arm 40 in a front-rear direction (Y-axis direction). For example, the Y direction movable table 74 is supported so as to be movable in the Y direction with respect to the upper frame 95, and the X direction movable table 73 is supported so as to be movable in the X direction with respect to the Y direction movable table 74. The X direction movable table 73, the turning shaft 96, and the turning arm 40 move along the Y direction along with the movement of the Y direction movable table 74. In addition, the turning shaft 96 and the turning arm 40 move along the X direction along with the movement of the X direction movable table 73.

The drive motors 76a, 76b include an X-axis drive motor 76a that drives the X direction movable table 73 and a Y-axis drive motor 76b that drives the Y direction movable table 74. For example, the screw groove is formed in a rotary shaft of the X-axis drive motor 76a, and the rotary shaft is screwed into a screw hole provided in the X direction movable table 73. The X direction movable table 73 moves in both directions along the X direction according to the rotational drive in the forward direction or the reverse direction of the X-axis drive motor 76a. The configuration in which the Y-axis drive motor 76b moves the Y direction movable table 74 can be similarly configured. For example, the X-axis drive motor 76a and the Y-axis drive motor 76b are controlled by the support controller 102a.

The X direction movable table 73 and the Y direction movable table 74 may be moved and driven by a linear motor mechanism, a rack-and-pinion mechanism, a mechanism using a belt and a pulley, or the like. The axis moving mechanism 70 is not necessarily an XY-direction moving mechanism, but may be an articulated robot arm apparatus. A two-dimensional moving motor may be such as one or more motor like the drive motors 76a, 76b It is not essential that the drive mechanism 60 include the axis moving mechanism 70 in addition to the turning mechanism 62. The drive mechanism 60 may be configured such that the X-ray detector 45 is turned about the turning axis at the fixed position by the turning mechanism 62.

In the first preferred embodiment, the axis moving mechanism 70 moves the turning shaft 96, the turning mechanism 62, and the turning arm 40 in the X-axis direction and the Y-axis direction. For this reason, during the turning of the turning arm 40 by the turning mechanism 62, the mechanical turning axis X1 of the turning arm 40 (the center axis of the turning shaft 96) can be moved along the XY-directions. Consequently, the X-ray detecting unit 44 and the X-ray generating unit 42 can perform a combined motion of a turning motion of the turning mechanism 62 and an axis moving motion of the axis moving mechanism 70. The turning orbits of the X-ray detecting unit 44 and the X-ray generating unit 42 can be set by adjusting a movement path of the turning shaft 96 by the axis moving mechanism 70.

The turning axis moving mechanism may be provided on the turning arm side. In this case, the lower end of the turning shaft 96 fixed at a fixed position in the XY-plane of the upper frame 95 is supported by the turning shaft moving mechanism provided in the turning arm side. The turning axis moving mechanism relatively moves the turning shaft 96 in the XY-direction with respect to the turning arm 40, so that the turning arm can move in the XY-direction with respect to the turning shaft 96 at the fixed position.

It is not essential that the drive mechanism 60 include the axis moving mechanism 70. For example, instead of providing the axis moving mechanism 70, the end of the turning arm 40 on the side of the X-ray detecting unit 44 may be configured to be driven to expand and contract along the longitudinal direction of the turning arm 40 by an expansion and contraction mechanism such as a linear motor or a rack and pinion mechanism. In this case, the X-ray detecting unit 44 moves in the two-dimensional direction along the turning surface of the X-ray detecting unit 44 or the like by the expansion and contraction drive of the turning arm 40, whereby the turning orbit of the X-ray detecting unit 44 can be changed. In addition, the X-ray detecting unit 44 may be configured to be movable close to and away from the X-ray generating unit 42 by a movable support mechanism such as a linear motor or a rack and pinion mechanism at the end of the turning arm 40. In this case, the movable support mechanism moves the X-ray detecting unit 44 back and forth with respect to the X-ray generating unit 42, so that the turning orbit of the X-ray detecting unit 44 can be changed.

The two-dimensional moving mechanism does not need to be the axis moving mechanism 70. For example, the end of the turning arm 40 on the side of the X-ray detecting unit 44 may be configured to be driven to expand and contract along the longitudinal direction of the turning arm 40 by the expansion and contraction mechanism such as a linear motor and a rack and pinion mechanism. In this case, the X-ray detecting unit 44 can move in the two-dimensional direction along the turning surface of the X-ray detecting unit 44 or the like by the expansion and contraction drive of the turning arm 40. In addition, the X-ray detecting unit 44 may be configured to be movable close to and away from the X-ray generating unit 42 by a movable support mechanism such as a linear motor or a rack and pinion mechanism at the end of the turning arm 40. In this case, the X-ray detecting unit 44 can move in the two-dimensional direction along the turning surface of the X-ray detecting unit 44 or the like by the movable support mechanism.

The vertical drive unit 82 is an example of the displacement mechanism. More specifically, the vertical drive unit 82 is an example of the vertical displacement mechanism that vertically displaces the X-ray detecting unit 44 with respect to the head P. The vertical drive unit 82 as the vertical displacement mechanism may be expressed as an example of the displacement mechanism that adds the movement in the vertical direction to the X-ray detecting unit 44. The vertical drive unit 82 may be expressed as an example of the displacement mechanism that adds the movement including the displacement component in the vertical direction to the X-ray detecting unit 44. In the first preferred embodiment, the vertical drive unit 82 vertically moves the turning arm 40 with respect to the head P. The X-ray detector 45 can vertically move together with the X-ray generating unit 42 by the vertical movement of the turning arm 40.

More specifically, the vertical drive unit 82 elevation-drives the turning arm 40 with respect to the post 80. More specifically, as illustrated in FIGS. 1 and 2, the upper frame 95 is supported by the post 80 so as to be movable up and down. The vertical drive unit 82 that elevates the upper frame 95 along the Z-axis direction is provided in the post 80. The vertical drive unit 82 is a mechanism that elevation-drives the upper frame 95 with respect to post 80. The vertical drive unit 82 includes a motor 83 as a second motor, a ball screw 84, a nut 85, and a plurality (in this case, four) of rollers 86.

A base end of the upper frame 95 surrounds a part in the vertical direction of the post 80. The roller 86 is provided at the base end of the upper frame 95. The roller 86 is supported in the base end of the upper frame 95 so as to be able to travel along a rail 80r that is provided on the surface of the post 80 and extends in the Z-axis direction. Thus, the upper frame 95 is supported so as to be movable up and down along the post 80. At this time, the rotation of the upper frame 95 about the Z-axis with respect to the post 80 is prevented by the roller 86 moving along the rail. When the vertical drive unit 82 is considered to include an element that guides the moving direction of the upper frame 95, the vertical drive unit 82 may be considered to include the motor 83, the ball screw 84, the nut 85, the roller 86, and the rail 80r.

The motor 83 is supported at a fixed position with respect to the post 80. In the example of FIG. 2, the motor 83 is provided below the post 80. The motor 83 rotates the ball screw 84 extending in the Z-axis direction about the Z-axis. The nut 85 is supported in the base end of the upper frame 95, and the ball screw 84 is screwed into the nut 85. The nut 85 is unrotatably fixed to the base end of the upper frame 95. As the ball screw 84 rotates according to the rotation of the motor 83 in the forward direction or the reverse direction, the nut 85 moves in the upward direction or the downward direction. The upper frame 95 moves up and down in the Z-axis direction as the nut 85 rotates. Consequently, the turning arm 40 and the X-ray generating unit 42 and the X-ray detecting unit 44, which are supported by the turning arm 40, move up and down in the Z-axis direction.

The displacement mechanism does not need to move up and down the X-ray detecting unit 44 together with the turning arm 40. For example, the vertical drive unit that moves up and down the entire turning arm 40 during the X-ray imaging with respect to the head P may be omitted, and only the X-ray detecting unit may be vertically displaced. More specifically, the X-ray detector 45 and the outer housing 46b may be regarded as the X-ray detecting unit, and the X-ray detector vertical movement drive unit 47 that vertically moves the X-ray detector 45 and the outer housing 46b may be regarded as the displacement mechanism. In this case, for example, while the X-ray detecting unit 44 is turning, the X-ray detecting unit including the X-ray detector 45 and the outer housing 46b may be moved up and down by the X-ray detector vertical movement drive unit 47. Consequently, the X-ray detector vertical movement drive unit 47 can also add the movement different from the turning of the X-ray detector 45, particularly the movement in the vertical direction orthogonal to the turning surface to the X-ray detecting unit including the X-ray detector 45 and the outer housing 46b. In this case, the X-ray detector vertical movement drive unit 47 can function as the vertical drive unit 82. So the motor 83 can serve as the second motor. The X-ray beam shape adjuster 50 may adjust the irradiation direction of the X-ray beam according to the vertical movement of the X-ray detector 45 by the X-ray detector vertical movement drive unit 47, and the X-ray beam may irradiate the X-ray detector 45. As an example in which the X-ray detector vertical movement drive unit 47 is used to retract the X-ray detecting unit 44 in the +Z direction, the state in which the X-ray detector 45 abuts on the bottom surface of the outer housing 46b to push down the outer housing 46b may be set to a normal setting, and the X-ray detector 45 may be moved in the +Z direction to avoid the abutment on the shoulder S to retract the X-ray detecting unit 44 in the +Z direction.

The displacement mechanism provides the outer housing 46b a vertical movement. And here, the vertical movement means a movement which causes a change of position in vertical direction (Z direction). So that, for example, the vertical movement of the outer housing 46b contains a movement of the outer housing 46b along vertical straight line orbit, other straight line orbit, curved line orbit, diagonal line orbit and so on as any orbits which cause positional change in vertical direction.

The subject holding unit 32 is a member that holds the imaging subject M (head P). In the first preferred embodiment, the subject holding unit 32 includes a front tooth region fixing portion that fixes a front tooth region Pa in the head P. More specifically, the subject holding unit 32 includes a chin rest 33, a head holder 34 (see FIG. 1), and a lower frame 35.

The chin rest 33 supports the tip of the lower jaw of the head P, thereby supporting the front tooth region Pa at a fixed position. Here, the front tooth region Pa refers to a front tooth and a region serving as a base supporting the front tooth in the head P, and for example, is the front tooth itself and a lower jaw (particularly, a jaw tip). That is, the chin rest is an example of the front tooth region fixing portion. The front tooth region fixing portion may not be the chin rest, but for example, may be a bite piece that is bitten by upper and lower front teeth.

The head holder 34 positions the head P with respect to the X-axis direction by holding the head P from both sides of the head holder 34. In the subject holding unit 32, the front tooth region fixing portion or the head holder 34 may be omitted.

The base end of the lower frame 35 is supported by the post 80 in a cantilever manner, and the distal end of the lower frame 35 extends from the post 80 along the horizontal direction. The chin rest 33 and the head holder 34 are supported at the distal end of the lower frame 35. The chin rest 33 and the head holder 34 are supported so as to go between the X-ray generating unit 42 and the X-ray detecting unit 44 that are supported by the turning arm 40. The head P supported by the subject holding unit 32 is held at the fixed position between the X-ray generating unit 42 and the X-ray detecting unit 44 during the turning of the X-ray generating unit 42 and the X-ray detecting unit 44.

The subject holding unit 32 is elevation-driven by a holding-unit drive unit 36. That is, the base end of the lower frame 35 is supported so as to be movable in the Z-axis direction with respect to the post 80. The lower frame 35 is elevation-driven in the Z-axis direction by drive of the holding-unit drive unit 36.

The holding-unit drive unit 36 includes a motor 36a, a ball screw 36b, a nut 36c, and a plurality of (in this case, four) rollers 36d. The base end of the lower frame 35 surrounds a part in the vertical direction of the post 80. The roller 36d is provided in the base end of the lower frame 35. The roller 36d is fixed in the lower frame 35 so as to be able to travel along the rail 80r that is provided on the post 80 and extends in the Z-axis direction. Thus, the lower frame 35 is supported so as to be movable up and down along the post 80. At this time, the rotation of the lower frame 35 about the Z-axis with respect to the post 80 is prevented by the roller 36d moving along the rail. When an element guiding the moving direction of the lower frame 35 is also considered to be included in the holding-unit drive unit 36, the holding-unit drive unit 36 may be considered to include the motor 36a, the ball screw 36b, the nut 36c, the roller 36d, and the rail 80r.

The motor 36a rotates the ball screw 36b extending in the Z-axis direction about the Z-axis. In this case, the motor 36a is supported by the base end of the lower frame 35, and the ball screw 36b extends upward from the base end of the lower frame 35 to reach the base end of the upper frame 95.

The nut 36c is supported by the base end of the upper frame 95. The nut 36c is unrotatably fixed to the base end of the upper frame 95. A ball screw 36b reaching the base end of the upper frame 95 is screwed into the nut 36c.

The ball screw 36b rotates according to the rotation in the forward direction or the reverse direction of the motor 36a, and the lower frame 35 can move up and down with respect to the nut 36c into which the ball screw 36b is screwed according to the rotation of the ball screw 36b. When the lower frame 35 moves up and down, the chin rest 33 and the head holder 34 supported by the lower frame 35 can also move up and down. Thus, the vertical holding position of the head P by the subject holding unit 32 and the vertical positions in the X-ray imaging regions by the X-ray generating unit 42 and the X-ray detecting unit 44 can be adjusted synchronously or separately.

The turning arm 40 is relatively elevated with respect to the head P while the height of the head P is held constant by the subject holding unit 32, which allows a spot irradiated with the X-ray in the head P to be changed in the Z-axis direction. Specifically, the turning arm 40 and the subject holding unit 32 are moved up and down by the vertical drive unit 82 according to the actual position of the head P while the state in which the lower frame 35 is not moved up and down with respect to the upper frame 95 by the holding-unit drive unit 36 is maintained, and the head P is held by the chin rest 33 and the head holder 34. Then, the vertical drive unit 82 raises the turning arm 40, and the holding-unit drive unit 36 relative lowers the subject holding unit 32 with respect to the turning arm 40 so as to keep the subject holding unit 32 at a constant height position. Alternatively, the vertical drive unit 82 lowers the turning arm 40, and the holding-unit drive unit 36 relatively raises the subject holding unit 32 with respect to the turning arm 40 so as to keep the subject holding unit 32 at a constant height position.

The upper frame 95 and the lower frame 35 are connected to each other through the ball screw 36b. For this reason, the turning arm 40 and the subject holding unit 32 are integrally moved up and down by the vertical drive unit 82.

The upper frame 95 is also an imager supporter that supports the imagers such as the X-ray generating unit 42 and the X-ray detecting unit 44. The lower frame 35 is also a subject supporter that supports a subject holder called the subject holding unit 32. The upper frame 95 and the lower frame 35 are an imager supporter subject supporter coupling type imaging supporter in which the upper frame 95 and the lower frame 35 are connected to each other by the ball screw 36b. The vertical drive unit 82 is also an imager elevator that elevates at least the imager supporter. The holding-unit drive unit 36 is also a subject elevator that elevates the subject supporter. The holding-unit drive unit 36 is also an imager-to-object distance adjuster that adjusts a distance between the imager supporter and the subject supporter. The vertical drive unit 82 moves up and down the imaging supporter, and the distance between the imager supporter configuring the imaging supporter and the subject supporter is adjusted by the imager inter-subject distance adjuster.

The holding-unit drive unit 36 is not provided, and the vertical drive unit 82 moves up and down only the imager supporter, so that another vertical drive unit independent of the vertical drive unit 82 may move up and down the subject supporter. In this case, the vertical drive unit 82 can also function as an imager-to-subject distance adjuster by moving up and down the imager supporter.

In any case, the X-ray imaging apparatus 20 includes the imager elevator and the imager-subject distance adjuster with respect to the moving up and down in the Z direction.

The imaging controller 100 controls the X-ray imaging operation of the imaging main body 30, and is a kind of computer apparatus. In the first preferred embodiment, the imaging controller 100 can function as a turning controller that controls the turning operation of the turning arm 40 by the drive mechanism 60 and a movement additional operation by the vertical drive unit 82 during the panoramic X-ray imaging. Other various pieces of control may be performed in addition to the imaging controller 100 controlling the operation of the turning arm 40. For example, the operation of an operation display 110 may be controlled to perform operation reception control and display control.

Figure 7:
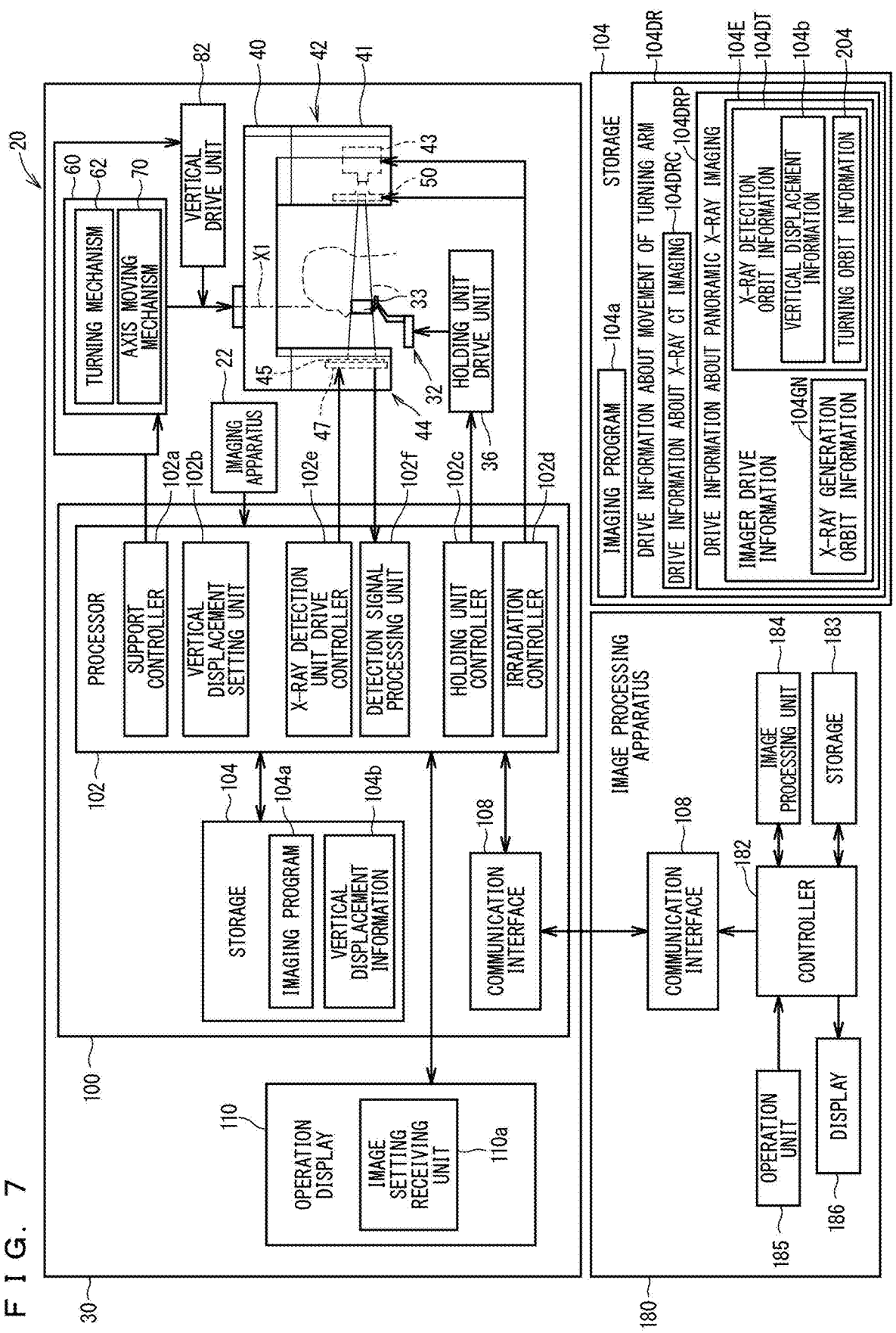
FIG. 7 is a block diagram illustrating an example of an electric configuration of the X-ray imaging apparatus.

FIG. 7 is a block diagram illustrating an example of an electric configuration of the X-ray imaging apparatus 20. For example, the imaging controller 100 includes at least one processor 102 and a storage 104.

The storage 104 is configured of a nonvolatile storage device such as a flash memory or a hard disk drive. An imaging program 104a, which controls the X-ray imaging operation by controlling the turning mechanism 62, the axis moving mechanism 70, the vertical drive unit 82, holding-unit drive unit 36, the X-ray generator 43, the X-ray beam shape adjuster 50, and the like according to various instructions while receiving the various instructions relating to the X-ray imaging, is stored in the storage 104. The storage 104 stores vertical displacement information 104b. The vertical displacement information 104b is information setting the vertical displacement operation of the X-ray detecting unit 44 during the panoramic X-ray imaging.

The movement orbit of the X-ray detecting unit 44 during the X-ray imaging is defined as an X-ray detection orbit DTL. The orbit on the XY-plane of the X-ray detecting unit 44 by the drive mechanism 60 is referred to as a horizontal orbit HZL, and the orbit of the turning on the XY-plane of the X-ray detecting unit 44 is referred to as a horizontal turning orbit HRL. The orbit of the movement in the vertical direction of the X-ray detecting unit 44 by the vertical drive unit 82 is set to an elevation orbit ELL. When the X-ray imaging in which the vertical displacement is involved in the horizontal turning of the X-ray detecting unit 44 is performed, the X-ray detection orbit DTL becomes a combined orbit of the horizontal turning orbit HRL and the elevation orbit ELL. The combined orbit may be referred to as a turning elevation orbit REL.

The X-ray detection orbit DTL of the X-ray detecting unit 44 during the panoramic X-ray imaging may be set to the turning elevation orbit REL. The turning elevation orbit REL may include the case where the movement amount of the vertical displacement of the X-ray detecting unit 44 is zero. The information defining the horizontal orbit HZL of the X-ray detecting unit 44 is set as horizontal movement information HZI, and the information defining the horizontal turning orbit HRL of the X-ray detecting unit 44 is set as horizontal turning movement information HRI. The information defining the elevation orbit ELL of the X-ray detecting unit 44 is defined as elevation information ELI. The vertical displacement information 104b is an example of the elevation information ELI. The elevation information ELI may include the case where the displacement amount of the movement in the vertical direction of the X-ray detecting unit 44 is zero.

The movement of the X-ray detecting unit 44 during the panoramic X-ray imaging becomes the movement in which the movement in the vertical direction by the vertical drive unit 82 is added to the turning operation of the X-ray detecting unit 44 by the turning mechanism 62. For example, the vertical displacement information 104b is information in which the turning operation of the X-ray detecting unit 44 by the drive mechanism 60 is associated with the movement operation in the vertical direction of the X-ray detector 45 by the vertical drive unit 82 with respect to the turning operation.

The support controller 102a controls the drive mechanism 60 and the vertical drive unit 82 based on the vertical displacement information 104b and the horizontal turning movement information HRI, so that the movement of the vertical drive unit 82 can be added to the X-ray detector 45 while the X-ray detector 45 is turning.

The movement of the X-ray detecting unit 44 may be the combined movement of the turning operation of the X-ray detecting unit 44 by the turning mechanism 62 and the movement operation of the turning shaft 96 by the axis moving mechanism 70 during the turning by the turning mechanism 62. Thus, the turning orbit of the X-ray detector 45 can be set to a non-circular orbit, or a size of the orbit can be changed. An example in which the turning orbit is changed will be described later.

The processor 102 includes a central processing unit (CPU) and the like. The processor 102 executes the imaging program 104a to implement various functions of the processor 102. The processor 102 is configured by a circuit, and includes the support controller 102a, a vertical displacement setting unit 102b, an X-ray detecting unit drive controller 102e, a detection signal processing unit 102f, a holding unit controller 102c, and an irradiation controller 102d as functional blocks implemented by the execution of the imaging program 104a. That is, the processor 102 is configured by a circuit that executes the imaging program 104a to perform, for example, support control, vertical displacement setting, drive control of the X-ray detecting unit, processing of a detection signal, holding unit control, and irradiation control.

The support controller 102a controls the turning operation of the turning arm 40 by the turning mechanism 62 and the axis moving mechanism 70 such that the X-ray generating unit 42 and the X-ray detecting unit 44 turn around the head P to perform the panoramic imaging while the head P of the imaging subject M held by the subject holding unit 32 is positioned between the X-ray generating unit 42 and the X-ray detecting unit 44.

The support controller 102a may control the operation of the vertical drive unit 82 to control the moving up and down of the turning arm 40.

The vertical displacement setting unit 102b sets the movement in the vertical direction of the X-ray detector 45 during the turning of the X-ray detector 45 in the panoramic X-ray imaging. The movement in the vertical direction of the X-ray detector 45 is a movement avoiding the contact with the shoulder S of the imaging subject M.

The X-ray detecting unit drive controller 102e controls the X-ray detector vertical movement drive unit 47 to adjust the vertical position of the X-ray detecting unit 44. In the first preferred embodiment, it is assumed that the adjustment of the vertical position of the X-ray detector 45 by the X-ray detector vertical movement drive unit 47 is performed before the panoramic X-ray imaging.

The detection signal processing unit 102f generates the X-ray imaging data suitable for the generation of the panoramic X-ray image based on the electric signal from the X-ray detector 45. The X-ray imaging data is provided to the image processing apparatus 180.

The holding unit controller 102c may control the holding-unit drive unit 36 to control the height position of the subject holding unit 32.

The irradiation controller 102d controls the X-ray generator 43 and the X-ray beam shape adjuster 50. For example, when the X-ray panoramic imaging is performed, the X-ray beam shape adjuster 50 is controlled to form the X-ray beam into the X-ray narrow beam. In the X-ray panoramic imaging, the X-ray beam shape adjuster 50 is controlled according to a launch angle when the launch irradiation is performed. The elevation position of the X-ray detecting unit 44 may also be adjusted by the X-ray detector vertical movement drive unit 47 according to the launch angle. The irradiation controller 102d can control the presence or absence of the emission of the X-ray and the intensity of the X-ray by controlling at least one of the voltage and the current supplied to the X-ray tube of the X-ray generator 43.

In this case, the operation when the imaging controller 100 performs the panoramic X-ray imaging will be mainly described, and the imaging controller 100 controls each unit of the X-ray imaging apparatus 20 to execute various pieces of processing based on the electric signal from the X-ray detector 45 also when performing other X-ray CT imaging and cephalogram imaging.

The imaging controller 100 is connected to the operation display 110. The operation display 110 includes a display apparatus that displays various types of information and an information input apparatus that inputs various types of information (including an imaging condition) and commands to the imaging controller 100. The display apparatus is implemented by a liquid crystal display apparatus, an organic electroluminescent (EL) display apparatus, or the like. The information input apparatus can be implemented by a switch, a pointer, a touch detection apparatus of a touch panel, or the like. For example, the operation display 110 may be configured of a touch panel display apparatus in which a touch detection apparatus is incorporated in a display surface of a display apparatus. The operation display 110 may have the configuration in which the display apparatus and the information input apparatus are separated. The operation display 110 may be provided at any member (for example, the post 80 and the housing 46) of the X-ray imaging apparatus 20, or may be provided at a spot (for example, an outer wall surface of the X-ray protection chamber or on another table) different from the X-ray imaging apparatus 20. The operation display 110 can function as an imaging setting receiving unit 110a.

The imaging controller 100 is connected to the image processing apparatus 180 through a communication interface 108. The image processing apparatus 180 is a kind of computer apparatus. The image processing apparatus 180 generates the X-ray image data, particularly the X-ray panoramic image data, based on the X-ray imaging data from the imaging controller 100. For example, the X-ray image processing apparatus 180 includes a controller 182, a storage 183, an image processing unit 184, an operation unit 185, and a display 186. The storage 183 is a non-volatile storage device such as a flash memory or an HDD, and stores the control program, the X-ray imaging data, the X-ray image data, and the like. The controller 182 includes at least one processor, and operates according to the control program stored in the storage 183 to execute processing of generating the X-ray image data (particularly, the X-ray panoramic imaging data) based on the X-ray imaging data transmitted from the imaging controller 100. For example, when the panoramic imaging is executed by the X-ray imaging apparatus 20, the imaging controller 100 performs the arithmetic processing of acquiring the panoramic image in which a target section is imaged. Specifically, the imaging controller 100 acquires one panoramic X-ray image by performing shift addition processing, in which the pixel value is added to a plurality of rectangular-shaped X-ray projection images acquired in the imaging main body 30 while the plurality of X-ray projection images are mutually shifted according to the position on the section.

FIG. 7 illustrates an image processing unit implemented by a processor for image processing. The processing of generating the X-ray image data may be implemented by a general-purpose processor included in the imaging controller 100, implemented by an image processing processor, or implemented by cooperation of these processors. The generated X-ray image data may be stored in the storage 183, or stored in another storage device, for example, the storage device of the imaging controller 100 or the storage device of the server.

The operation unit 185 is an input apparatus inputting various types of information and the support to the image processing apparatus 180, and can be implemented by a switch, a pointer, a touch detection apparatus of a touch panel, or the like.

The display 186 is implemented by a liquid crystal display apparatus, an organic electroluminescent (EL) display apparatus, or the like. The panoramic X-ray image generated by the image processing apparatus 180 may be displayed on the display 186 (see FIG. 1).

A part or whole of the function implemented in each of the above units may be implemented in a hardware manner using a dedicated logic circuit or the like. A part or whole of the function implemented in each of the above units may be processed by a single processor in an integrated manner, or appropriately processed by a plurality of processors in a distributed manner.

The storage 104 stores drive information 104DR (support drive information 104DR) about the movement of the turning arm 40 that is the support in the X-ray imaging. For example, the drive information 104DR includes drive information 104DRP about the panoramic X-ray imaging and drive information 104DRC about the X-ray CT imaging. When consequently determining the orbit of the X-ray detecting unit 44 in the X-ray imaging, the drive information 104DR is also information determining the orbit of the X-ray detecting unit 44. When consequently determining the orbit of the X-ray generating unit 42 in the X-ray imaging, the drive information 104DR is also information determining the orbit of the X-ray generating unit 42. In the drive information 104DR, an element defining the orbit of the X-ray detecting unit 44 may be considered as X-ray detection orbit information 104DT, and an element defining the orbit of the X-ray generating unit 42 may be considered as X-ray generation orbit information 104GN. When a set of the X-ray generating unit 42 and the X-ray detecting unit 44 is the imager, the drive information 104DR defines the orbit of the X-ray generating unit 42 and the X-ray detecting unit 44, namely, the imager, so that the drive information 104DR may be considered as imager orbit information 104E. It may be considered that the X-ray detection orbit information 104DT in the drive information 104DRP includes the vertical displacement information 104b and the horizontal turning movement information HRI.

<Operation of X-Ray Imaging Apparatus>

Figure 8:
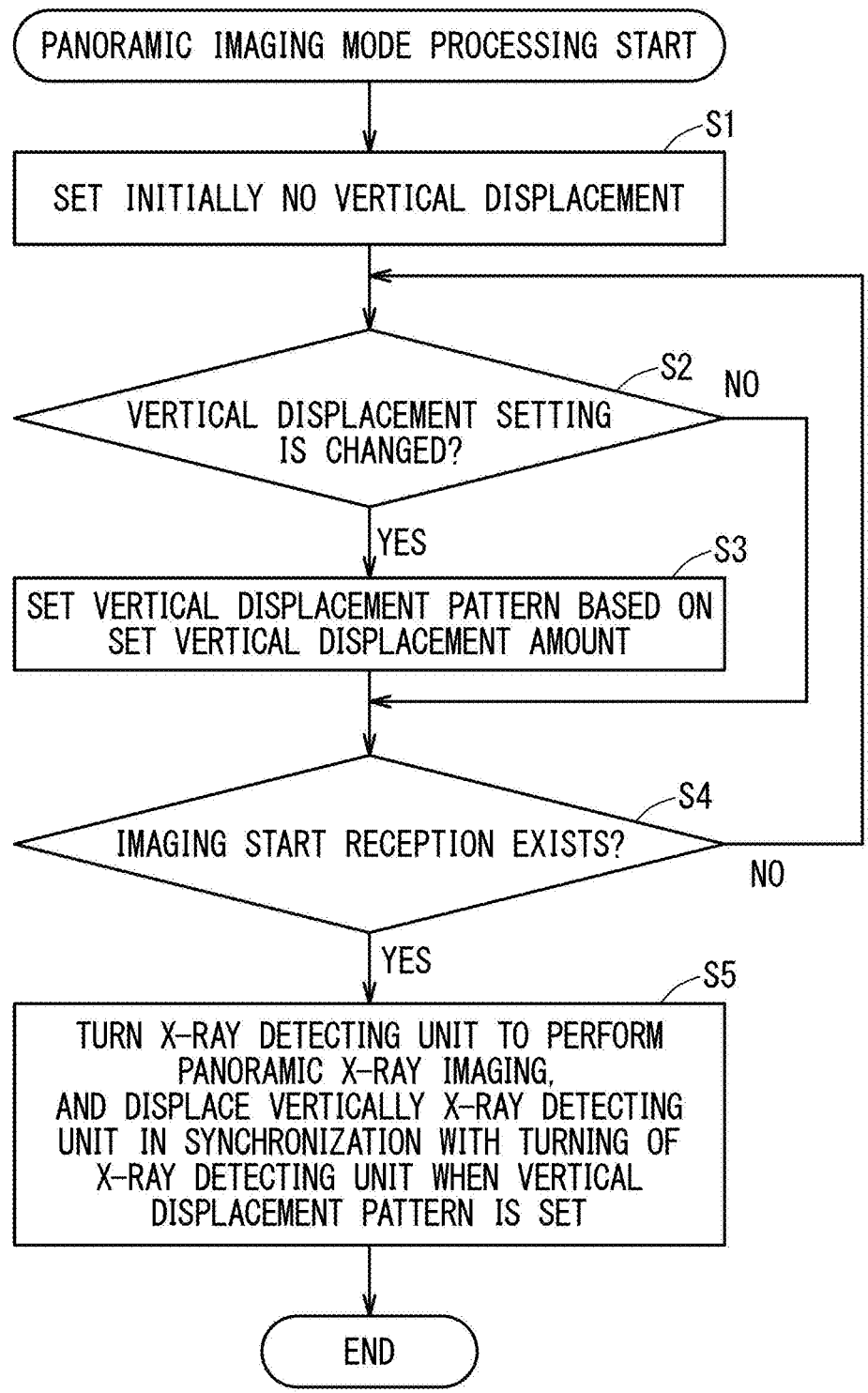
FIG. 8 is a flowchart illustrating an example of processing performed by an imaging controller.

The operation of the X-ray imaging apparatus will be described focusing on the panoramic X-ray imaging. The following operation is performed under the control of the imaging controller 100, particularly the processor 102. FIG. 8 is a flowchart illustrating an example of processing related to the panoramic X-ray imaging.

When the X-ray imaging apparatus 20 is activated, electricity is supplied to each unit, so that the imaging main body 30, the imaging controller 100, and the image processing apparatus 180 become a standby state. Then, a setting screen of the imaging mode is displayed on the operation display 110. For example, the setting screen of the imaging mode is a screen selecting one mode from the panoramic X-ray imaging mode, the X-ray CT imaging mode, and the like. When the panoramic X-ray imaging mode is selected through a touch operation of the operation display 110 or the like, the panoramic imaging mode processing is started.

In performing the panoramic X-ray imaging, the heights of the turning arm 40 and the subject holding unit 32 are adjusted according to the height position of the head P of the imaging subject M. The height adjustment may be performed by the operator inputting an instruction to raise or lower the turning arm 40 and the subject holding unit 32 through the operation display 110 or the like.

The disposition in the Z direction of the subject holding unit 32 and the upper frame 95, namely, the relationship between the heights of the subject holding unit 32 and the upper frame 95 may be set so as to adapt to the shape of the standard head P before the panoramic X-ray imaging. When the lower jaw is longer than the standard head P, the distance in the Z direction of the upper frame 95 with respect to the subject holding unit 32 may be increased by the imager-subject distance adjuster, and then the X-ray imaging may be performed, which corresponds to an individual skeleton.

When the panoramic imaging mode processing is started, no vertical displacement is initially set in step S1. For this reason, when the special instruction related to the vertical displacement does not exist, the X-ray detecting unit 44 turns without the vertical displacement to execute the panoramic X-ray imaging.

The imaging orbit of the X-ray detector 45 during the X-ray CT imaging may be a orbit centered on the turning axis X1 at a fixed position. That is, the X-ray CT imaging may be performed while the turning arm 40 is turned by the turning mechanism 62 without moving the turning shaft 96 by the axis moving mechanism 70 (while the turning shaft 96 is stopped).

Figure 9:
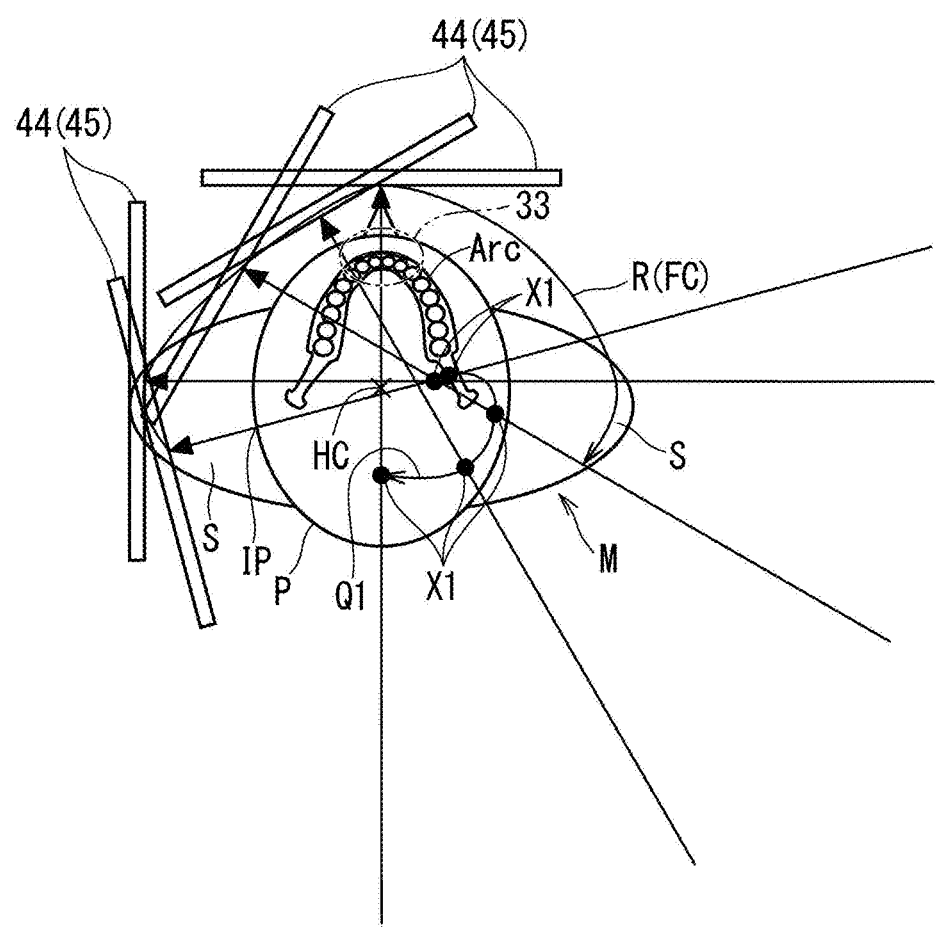
FIG. 9 is an explanatory view illustrating an example of a turning orbit (first turning orbit)

The imaging orbit of the X-ray detector 45 during the panoramic X-ray imaging may be an orbit centered on the moving turning axis X1. That is, the panoramic X-ray imaging may be performed by turning the turning arm 40 using the turning mechanism 62 while the turning shaft 96 is moved by the axis moving mechanism 70. For example, FIG. 9 illustrates an example of the turning orbit R. FIG. 9 illustrates the shape of the head P. It is assumed that the shape of the shoulder S is standard.

The turning orbit R is an arc-shaped line along an outer peripheral side of the dental arch Arc. The turning orbit may be set in a range in which the X-ray transmitted through the front tooth and the molar in the dental arch, and the region including a vicinity of the mandibular angle from the temporomandibular joint is detected. From this viewpoint, the turning orbit R may be an arc-shaped orbit in a range (for example, a range of)±115° exceeding 90° to the left and right with a front portion at the center in the left-right direction of the head P as the center. The turning orbit R is an example of the horizontal turning orbit HRL.

The center of the head P is defined as a head center HC, and a point through which the X-ray narrow beam passes in the head surface is defined as a point IP. There are various ways of determining the head center HC. For example, the head center HC may be set to an intersection od the front-back center and the left-right center. A direction in which the X-ray travels at the point IP as viewed in the Z direction and a direction parallel to this direction are referred to as a forward irradiation direction, and an opposite direction of the forward irradiation direction is referred to as a reverse irradiation direction. The distance between the head center HC and the point IP varies depending on the position of the point IP as the irradiation direction changes, so that the movement of the X-ray detecting unit 44 and the turning shaft 96 is required to cope with this change. The movement amount is considered as an offset value, and a relationship between the movement according to the distance between the X-ray detecting unit 44 and the surface of the head P and the movement of the turning shaft 96 is considered. In the case of the first preferred embodiment, the turning orbit R is an orbit that moves the X-ray detecting unit 44 away from the surface of the head P on the lateral of the head P and moves the X-ray detecting unit 44 closer to the surface of the head P in front of the head P. That is, the distance of the X-ray detecting unit 44 to the surface of the head P is small on the front and is large on the lateral. The orbit may be referred to as a front approach orbit FC. In this manner, the turning orbit R may be set to the front approach orbit FC. In order to move the X-ray detecting unit 44 along the turning orbit R, the turning shaft 96 is moved by the axis moving mechanism 70 when the X-ray detecting unit 44 turns about the turning shaft 96. For example, the position of the turning shaft 96 may be adjusted according to the distance of the turning orbit R with respect to the surface of the head P. For example, the movement close to the surface is implemented by the moving the turning shaft 96 in the reverse irradiation direction in a portion (in front of the head P) of the turning orbit R moving close to the surface of the head P, and the movement away from the surface is implemented by moving the turning shaft 96 in the forward irradiation direction in a portion (in the lateral of the head P) of the turning orbit R moving away from the surface of the head P.

In this case, the storage 104 preferably stores turning orbit information 204 defining the turning orbit. The turning orbit information 204 is an example of the horizontal turning movement information HRI, and for example, is information that defines the position of the turning axis X1 in the turning operation of the X-ray detecting unit 44. When the imaging controller 100 controls the turning operation of the X-ray detecting unit 44 by the turning mechanism 62, the X-ray detecting unit 44 can move along the turning orbit R by moving the turning shaft 96 by the axis moving mechanism 70 based on the turning orbit information 204. The user may arbitrarily set the turning orbit information 204. The user may change the turning orbit information 204 stored in the storage 104 to set the new turning orbit information 204.

The turning orbit R may be set so as to pass through the position within 10 cm from the surface of the head P in front of the head P. The turning orbit R may be set so as to pass through the position within 10 cm from the surface of the head P over the entire circumference of the head P.

Regarding the disposition of the X-ray detecting unit 44, when a distance AD between the X-ray detecting unit 44 and the surface (point IP) of the head P in a certain disposition AA is smaller than a distance BD between the X-ray detecting unit 44 and the surface of the head P in another disposition BA, in the comparison between the disposition AA and the disposition BA, the state of the disposition AA is expressed as "the approach degree is high", and the state of the disposition BA is expressed as "the approach degree is low".

The distance between the X-ray detecting unit 44 and the surface (point IP) of the head P when the X-ray detecting unit 44 is located in front of the head P is defined as a distance FD, and the distance between the X-ray detecting unit 44 and the surface (point IP) of the head P when the X-ray detecting unit 44 is located on the lateral of the head P is defined as a distance SD. A value of distance FD/distance SD is set as a proximity separation ratio FSR. The smaller proximity separation ratio FSR is expressed as "a front approach ratio is high" and "a lateral approach ratio is low", and the larger proximity separation ratio FSR is expressed as "a front approach ratio is low" and "a lateral approach ratio is high" Compared with the turning orbit in which the distance FD and the distance SD are equal, the turning orbit R of the first preferred embodiment has the higher front approach ratio.

The distance to the front surface of the head P in front of the head P (at least in front of the center in the left-right direction of the head P) may be expressed as a separation distance of the orbit with respect to the center portion in the left-right direction of the front portion of the head. The distance to the side surface of the head P in the side (at least the left and right at the center in the front-back direction of the head P) of the head P may be expressed as the separation distance of the orbit with respect to the center portion in the front-back direction of the side of the head.

In step S2 after step S1, it is checked whether the setting of the vertical displacement amount is changed. For example, the setting of the vertical displacement amount is changed through the operation display 110. For example, an icon setting the vertical displacement amount is displayed on the operation display 110, and the setting change of the vertical displacement amount is received by touching the icon. When it is determined that the setting of the vertical displacement amount is changed, the processing proceeds to step S3. When it is determined that the setting is not changed, the processing skips step S3 and proceeds to step S4.

In step S3, a vertical displacement pattern is set based on the set vertical displacement amount.

Figure 16:
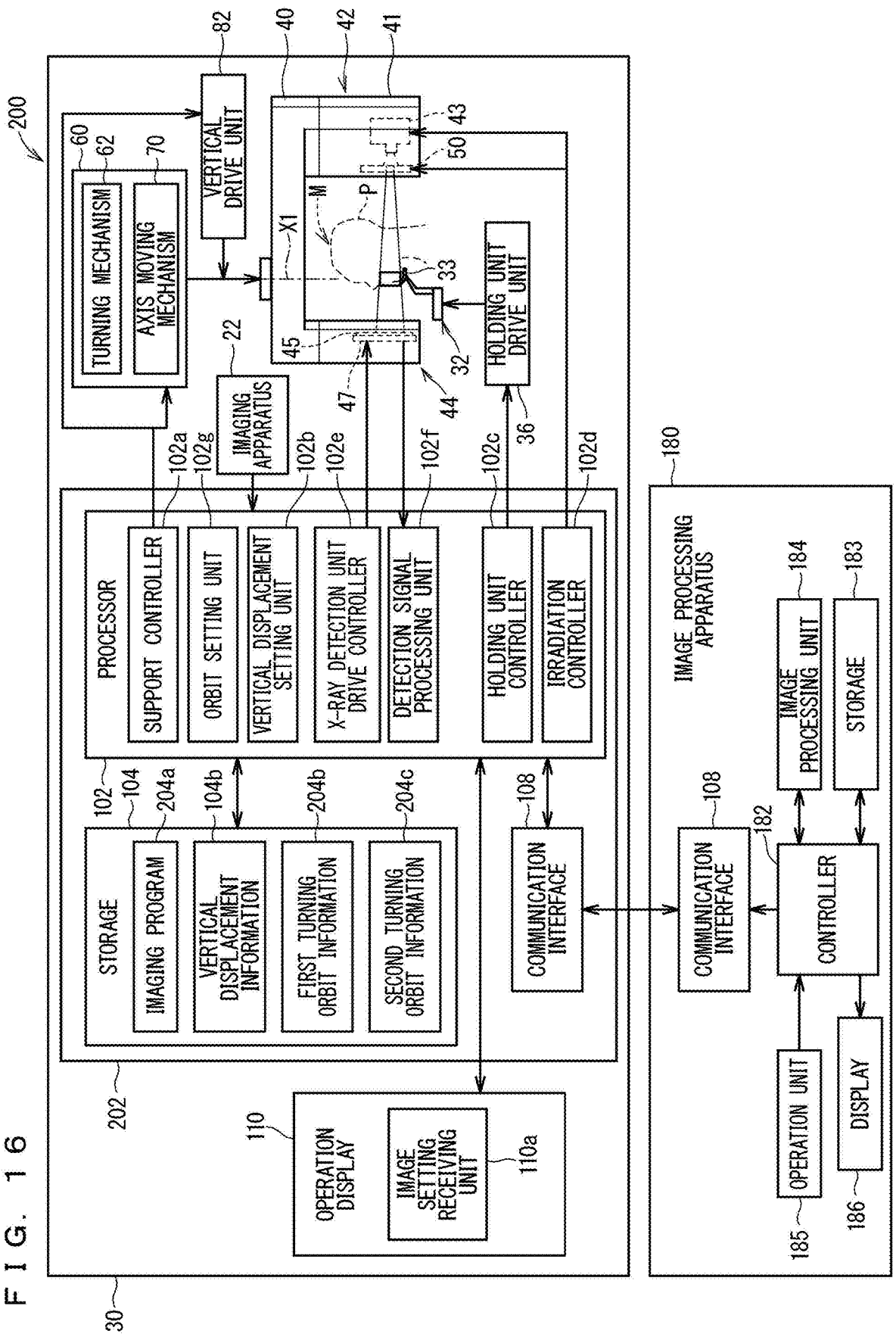
FIG. 16 is a block diagram illustrating an example of an electric configuration of an X-ray imaging apparatus according to a second embodiment.

Here, a setting example of the vertical displacement amount will be described. For example, as illustrated in FIG. 16, the vertical displacement information 104b includes a vertical displacement pattern 104b1 in which the height information of the X-ray detecting unit 44 is associated with the turning angle of the X-ray detecting unit 44 during the panoramic X-ray imaging. The data of the vertical displacement pattern 104b1 may be expressed by a data string or an expression having a swing angle as a variable. Assuming that the initial position of the turning angle is a front position at the center in the left-right direction (X direction) of the head P, that the clockwise direction from the initial position is a + direction, and that the counterclockwise direction from the initial position is a − direction, the height is smallest at the turning angle 0° and the height is largest at the turning angle ±90°. At the turning angle (for example, ±90°) at which the X-ray detecting unit 44 is located in the lateral of the head P, a height hm [mm] of the X-ray detecting unit 44 is set to exceed a height hs [mm] of the shoulder S. In other words, the vertical displacement pattern 104b1 determines the position of the X-ray detecting unit 44 during the turning of the X-ray detecting unit 44 such that the position of the lower end of the X-ray detecting unit 44 passing through the lateral of the head P is located higher than the position of the lower end of the X-ray detecting unit 44 passing through the front of the head P. The imaging controller 100 controls the drive of adding the vertical movement to the X-ray detecting unit 44 by the vertical drive unit 82 along the vertical displacement pattern 104b1. The vertical drive unit 82 functions as a mechanism that moves the turning arm 40 up and down with respect to the head P. At the turning angle (for example, ±90°) at which the X-ray detecting unit 44 is located in the lateral of the head P, a height hm [mm] of the X-ray detecting unit 44 is set to exceed a height hs [mm] of the shoulder S. The height is set to smoothly change while drawing a curve between the turning angle 0° and the turning angle ±90°. In the range where the turning angle exceeds the turning angle ±90°, the height at the turning angle ±90° may be maintained, or the height may be changed so as to be small. The imaging controller 100 may adjust the height position of the X-ray detecting unit 44 as the height position of the initially-positioned X-ray detecting unit 44 is the height at the turning angle 0°.

The vertical displacement information 104b may include only one vertical displacement pattern 104b1. In this case, the setting whether to perform the vertical displacement is input in step S2, and the one vertical displacement pattern 104b1 is set as the vertical displacement pattern in step S3.

The vertical displacement information 104b may include a plurality of vertical displacement patterns 104b1, 104b2, 104b3. The plurality of vertical displacement patterns 104b1, 104b2, 104b3 are different from each other in height difference. The vertical displacement patterns 104b1, 104b2, 104b3 may be considered as an example of the elevation information regarding the movement in the vertical direction of the X-ray detecting unit 44. In FIG. 10, at the position of the turning angle ±90°, the vertical displacement pattern 104b2 has the largest height, the vertical displacement pattern 104b3 has the smallest height, and the vertical displacement pattern 104b1 has an intermediate height. Thus, by applying any one of the vertical displacement patterns 104b1, 104b2, 104b3 according to the position of the shoulder S of the imaging subject M, the X-ray detecting unit 44 can be brought close to the head P to perform the panoramic X-ray imaging while minimizing the vertical displacement of the X-ray detecting unit 44 within the range in which the X-ray detecting unit 44 can avoid coming into contact with the shoulder S. In the illustrated example, the position of the shoulder S is higher than the vertical displacement pattern 104b3 at the position of the turning angle ±90°, so that the vertical displacement pattern 104b1 or 104b2 is selected.

The height of the X-ray detecting unit 44 with respect to the head P when the X-ray detecting unit 44 is located in front of the head P is defined as a height FH, and the height of the X-ray detecting unit 44 with respect to the head P when the X-ray detecting unit 44 is located in the lateral of the head P is defined as a height SH. A difference between the height FH and the height SH is defined as a height difference FS. Consequently, the vertical displacement pattern 104b2 has the height difference FS larger than that of the vertical displacement pattern 104b3, and the vertical displacement pattern 104b3 has the height difference FS smaller than that of the vertical displacement pattern 104b2.

When the plurality of vertical displacement patterns 104b1, 104b2, 104b3 are included as the vertical displacement information 104b, in step S2, the user observes the physical constitution (physique) and the like, and sets and inputs which of the vertical displacement patterns 104b1, 104b2, 104b3 is applied, or inputs how much the vertical displacement is performed. In step S3, according to the selected pattern, the vertical displacement patterns 104b1, 104b2, 104b3 are read and set as the vertical displacement pattern, or the vertical displacement pattern according to the input vertical displacement amount is set. In this way, the setting of the height difference in the turning orbit R of the X-ray detecting unit 44 can be changed.

The turning orbit R can be set so that the X-ray detecting unit 44 passes over the shoulder S or passes over at least a part of the shoulder S in a timing the X-ray detecting unit 44 comes to the lateral of the head P. At this setting, the placement of the X-ray detecting unit 44 on X-Y coordinate in the timing the X-ray detecting unit 44 comes to the lateral of the head P can be set to a position of a shoulder S of a standard physical constitution of the imaging subject M, or can be set to a position of a shoulder of an individual physical constitution.

In next step S4, it is determined whether the reception of imaging start is performed. For example, the imaging start may be received through a pushbutton switch (referred to as a deadman switch) connected to the imaging controller 100. When it is determined that the imaging start reception is not performed, the processing returns to step S2, and the pieces of processing of steps S2, S3 are repeated. When it is determined that the imaging start reception is performed, the processing proceeds to step S5. When it is determined that the imaging start reception is not performed, the processing may not return to step S2 but may return to immediately after step S2 or immediately before step S4 itself.

The initial setting in step S1 and the check whether the setting of the vertical displacement amount (height difference) is changed in step S2 can be deformed from those described above. For example, the vertical displacement can be performed as the initial setting of step S2. In this case, whether the setting of the vertical displacement amount is changed in step S2 is determined by whether the displacement amount is changed from the vertical displacement amount in step S1. For example, the vertical displacement pattern 104b3 is set as the initial setting, and when the vertical displacement pattern 104b1 or 104b2 is required from the position of the shoulder S, it is determined in step S2 that the setting change of setting the vertical displacement amount from small to large is performed by checking the input of the vertical displacement pattern 104b1 or 104b2. The setting change of the vertical displacement amount may include a setting change of setting the vertical displacement amount from large to small. For example, although the vertical displacement pattern 104b2 is set as the initial setting, the contact with the shoulder S can be sufficiently avoided, and when the target region is likely to be lost, the vertical displacement pattern 104b2 is changed to the vertical displacement pattern 104b3, or the vertical displacement is changed to no vertical displacement.

In step S5, the X-ray detecting unit 44 is turned to perform the panoramic X-ray imaging. At this time, when the vertical displacement is set, the X-ray detecting unit 44 is vertically displaced according to the set vertical displacement pattern in synchronization with the turning of the X-ray detecting unit 44. Consequently, the vertical drive unit 82 can vertically move the X-ray detecting unit 44 such that the lower end position of the X-ray detecting unit 44 passing through the lateral of the head P is located higher than the lower end position of the X-ray detecting unit 44 passing through the front of the head P with respect to the X-ray detecting unit 44. When the vertical displacement is not set, the panoramic X-ray imaging without the normal vertical displacement is performed.

During the turning, the X-ray emitted from the X-ray generating unit 42 passes through the head P to enter the X-ray detecting unit 44. The X-ray imaging data is generated based on the electric signal corresponding to the X-ray detected by the X-ray detecting unit 44, and the X-ray imaging data is provided to the image processing apparatus 180. Thus, the image processing apparatus 180 generates the panoramic X-ray image based on the X-ray imaging data.

In performing the panoramic X-ray imaging, the range of the panoramic imaging region or the like may be set through the operation display 110 or the like, and the X-ray beam shape adjuster 50 may be controlled according to the setting.

In performing the panoramic X-ray imaging, the launch angle of the X-ray beam may be set through the operation display 110, the X-ray beam shape adjuster 50 may be controlled according to the setting to adjust the irradiation direction of the X-ray beam, and the X-ray detector vertical movement drive unit 47 may be controlled according to the irradiation direction to adjust the vertical position of the X-ray detecting unit 44.

<Panoramic X-Ray Imaging Example>

Figure 11:
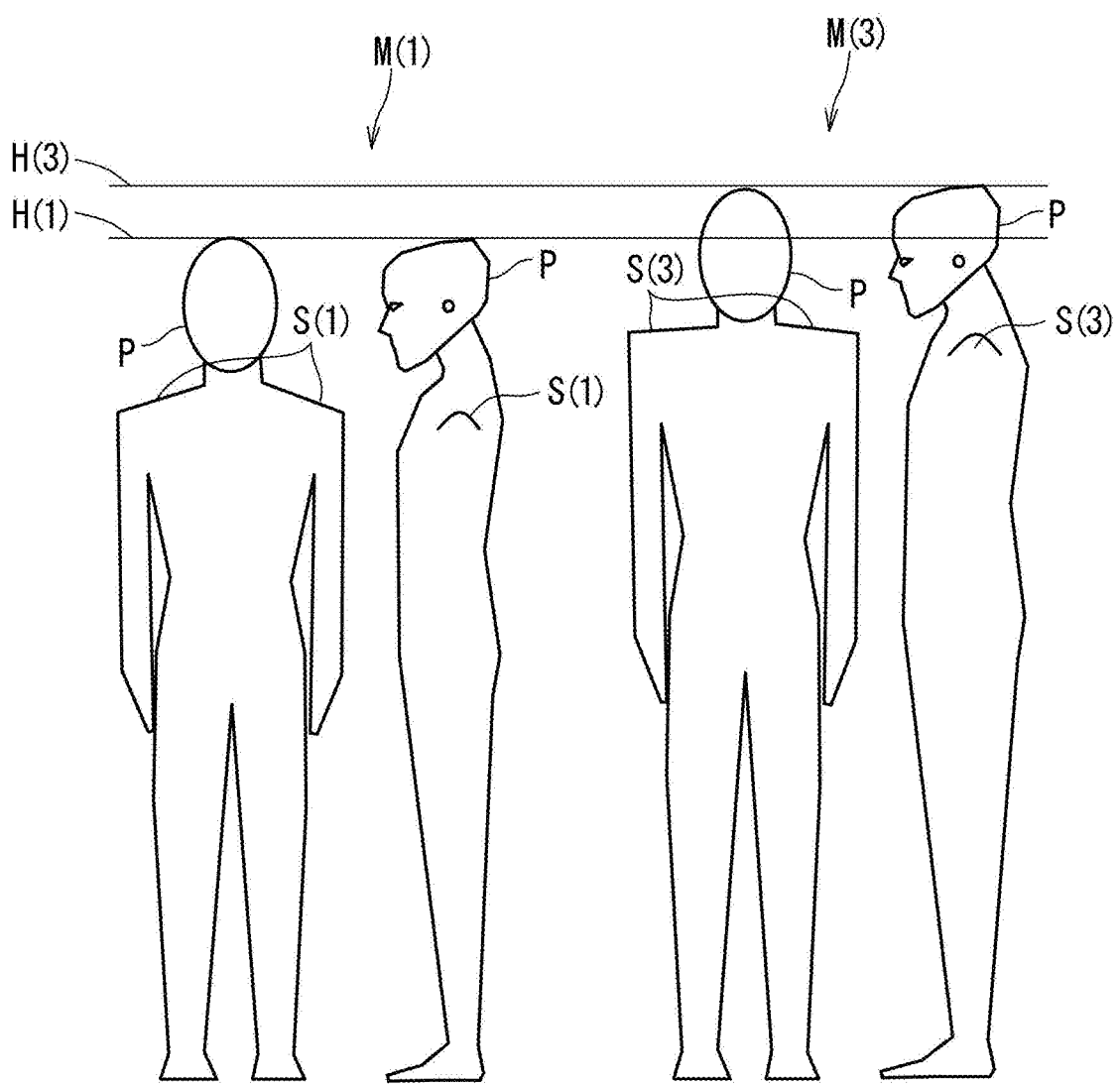
FIG. 11 is an explanatory view illustrating physical constitution examples of a plurality of imaging subjects.

FIG. 11 is a view illustrating physical constitution examples of imaging subjects M(1), M(3). The imaging subject M(1), M(3) have different heights, and a height H(1) of the imaging subject M(1) is smaller than a height H(3) of the imaging subject M(3). The imaging subject M(1) has a shoulder S(1) that is normally lowered with respect to the head P. A shoulder S(3) of the imaging subject M(3) is a square shoulder. The relative position of the shoulder S(3) with respect to the head P of the imaging subject M(3) is higher than the relative position of the shoulder S(1) with respect to the head P of the imaging subject M(1).

Figure 12:
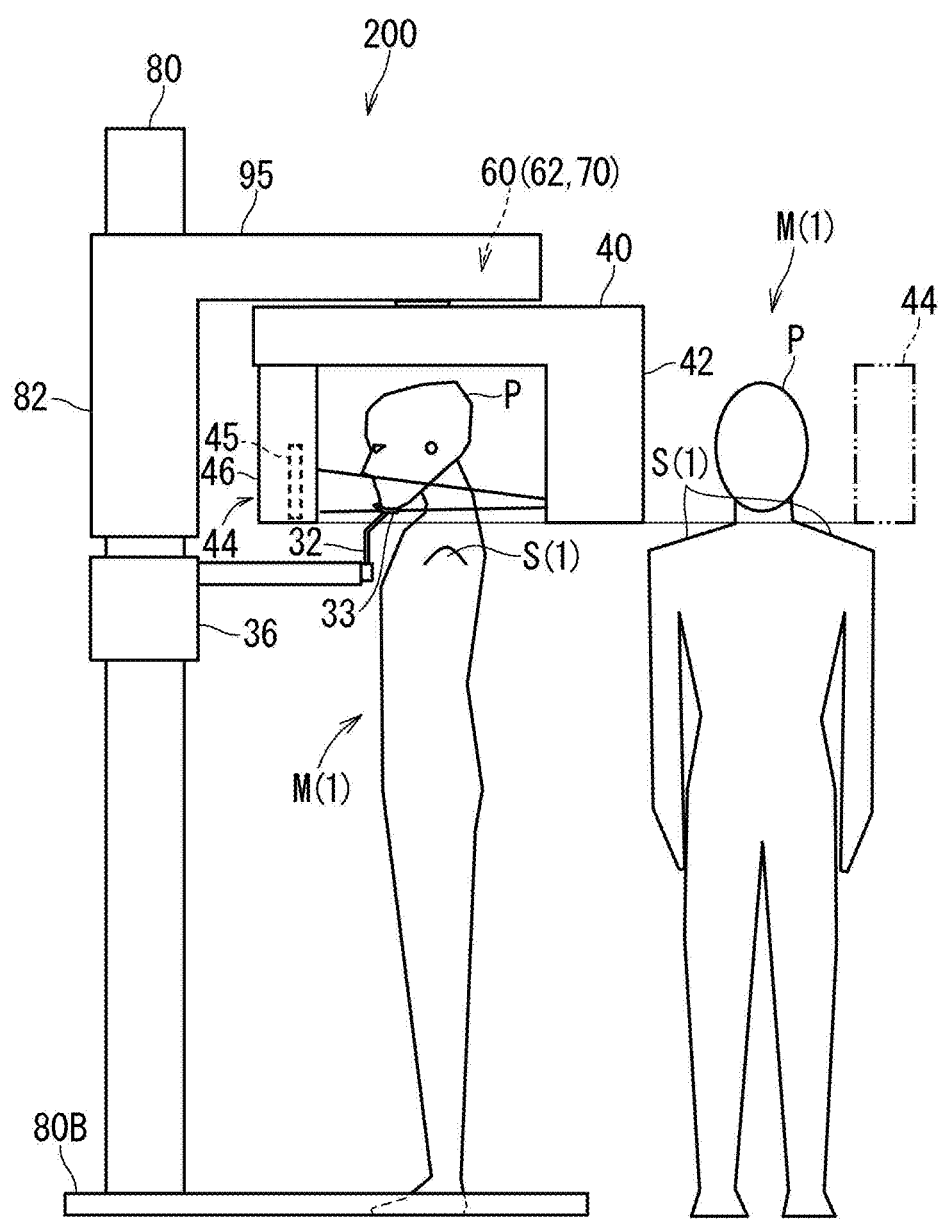
FIG. 12 is an explanatory view illustrating a positional relationship between an X-ray detecting unit and a housing with respect to the imaging subject during panoramic imaging.
Figure 13:
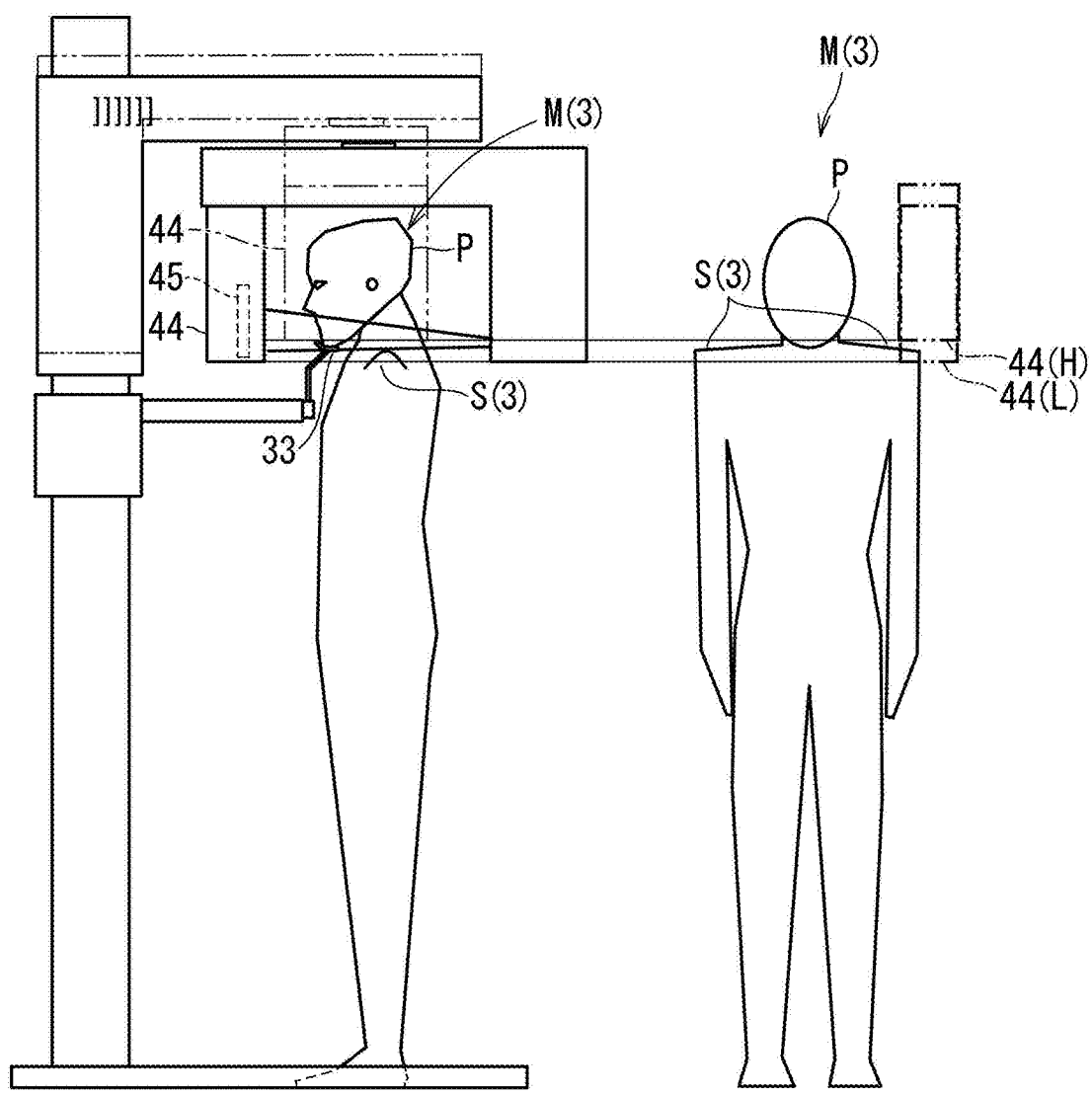
FIG. 13 is an explanatory view illustrating the positional relationship between the X-ray detecting unit and the housing with respect to the imaging subject during the panoramic imaging.

With reference to FIGS. 12 and 13, the case of performing the panoramic X-ray imaging on the imaging subjects M(1), M(3) will be described. In each of FIGS. 12 and 13, the positional relationship of the X-ray detecting unit 44 with respect to the imaging subjects M(1), M(3) viewed from the side is illustrated on the left side, and the positional relationship of the X-ray detecting unit 44 with respect to the imaging subject M(1), M(3) viewed from the front is illustrated on the right side. FIGS. 12 and 13 illustrate an example, in which the X-ray beam is launch-irradiated and the lower end of the housing 41 accommodating the X-ray generator 43 and the lower end of the housing 46 accommodating the X-ray detector 45 are aligned at the same height position. It is not essential that the X-ray beam is launch-irradiated, and thus, the lower end of the housing 41 accommodating the X-ray generator 43 may be located below the lower end of the housing 46 accommodating the X-ray detector 45.

When the imaging subject M(1) is targeted, as illustrated in FIG. 12, the X-ray detecting unit 44 can turn without contacting with the imaging subject M(1) in front of the head P. In addition, the shoulder S(1) is normally lowered with respect to the head P. For this reason, in the lateral of the head P, the shoulder S(1) is positioned below the jaw chip or the like of the head P. Thus, the X-ray detecting unit 44 hardly contacts the shoulder S (1) even in the lateral of the head P. Consequently, even when the X-ray detecting unit 44 is not vertically displaced, the X-ray detecting unit 44 can be turned around the head P to perform the panoramic X-ray imaging.

When the imaging subject M(3) is targeted, as illustrated in FIG. 13, the X-ray detecting unit 44 can turn without contacting with the imaging subject M(3) in front of the head P. However, the shoulder S(3) is the square shoulder. For this reason, in the lateral of the head P, there is a possibility that the shoulder S(3) may be located near the height position of the jaw chip or the like of the head P.

In this case, there is a possibility that the X-ray detecting unit 44 comes into contact with the shoulder S(3) in the lateral of the head P (see the position of an X-ray detecting unit 44(L) in FIG. 13). In such a case, it is also conceivable to perform the panoramic X-ray imaging without the vertical displacement while the X-ray detecting unit 44 is disposed at the height position (see the lowermost end position of an X-ray detecting unit 44(H)) that is not in contact with the shoulder S(3) in the state where the X-ray detecting unit 44 is located in the lateral of the head P. However, in this case, the lowermost end of the X-ray detecting unit 44 is located above the jaw chip, and there is a possibility that the front lower end of the dental arch Arc may not be imaged in the panoramic X-ray image. Accordingly, the vertical displacement pattern is set as described in steps S2, S3, and the X-ray detection orbit in which the X-ray detecting unit 44 is vertically displaced is set such that the X-ray detecting unit 44 becomes lower in front of the head P and becomes higher in the lateral of the head P (see the X-ray detecting unit 44(H) in FIG. 13) as described in step S5. Consequently, the X-ray detecting unit 44 can be turned along the turning orbit R while avoiding the contact of the X-ray detecting unit 44 with the shoulder S. Consequently, the panoramic X-ray image in which the front lower end of the dental arch Arc is imaged while avoiding the contact of the X-ray detecting unit 44 with the shoulder S(3) can be generated.

According to the X-ray imaging apparatus 20 configured as described above, the movement in which the contact with the imaging subject M is avoided is added to the X-ray detecting unit 44 when the X-ray generating unit 42 and the X-ray detecting unit 44 turn around the head P located therebetween. Thus, the X-ray detecting unit 44 can be brought as close to the head P as possible while the shoulder hitting of the X-ray detecting unit 44 is prevented. In other words, even when the turning orbit of the X-ray detecting unit 44 is the orbit close to the head P, the X-ray detecting unit 44 can be prevented from hitting the shoulder. When the X-ray detecting unit 44 can be brought close to the head, the X-ray transmitted through the head P is clearly projected on the X-ray detecting unit 44, so that the resolution of the panoramic X-ray image can be improved.

When the X-ray detecting unit 44 is vertically displaced according to the vertical displacement patterns 104b1, 104b2, 104b3, an oblique panoramic X-ray image in which a region gradually going upward from the front toward the rear in the side view is imaged is generated. The dental arch Arc extends so as to gradually go upward from the front toward the rear in the side view, so that the dental arch Arc can be sufficiently imaged even in the oblique panoramic X-ray image.

In addition, a human body region that easily comes into contact with the turning X-ray detecting unit 44 hardly exists below the front of the head P. The shoulder S can exist below the lateral of the head P as the human body region that easily comes into contact with the turning X-ray detecting unit 44. When the displacement mechanism is the vertical drive unit 82 that is a position example of the vertical displacement mechanism vertically displacing the X-ray detecting unit 44 with respect to the head P, the X-ray detecting unit 44 can be positioned at the lower side when passing through the front of the head P, and the X-ray detecting unit 44 can be positioned at the upper side when passing through the lateral of the head P. Consequently, it is possible to add effective motion can be added in order to bring the X-ray detecting unit 44 closer to the head P while preventing the contact of the X-ray detecting unit 44 with the shoulder S.

For example, at the front position of the head P, the X-ray detecting unit 44 may have the height located at the center of the dental arch and the outer periphery of the jaw chip. The lateral position of the head P may be the height positioned around the outer periphery of the mandibular angle from the temporomandibular joint of both end portions of the dental arch Arc.

When the vertical drive unit 82 is a mechanism that moves the turning arm 40 up and down with respect to the head P, the X-ray generating unit 42 and the X-ray detecting unit 44 can be moved up and down together by moving the turning arm 40 up and down. Thus, the relative positional relationship between the X-ray generating unit 42 and the X-ray detecting unit 44 can be kept constant during the turning of the X-ray detecting unit 44, and the separate height control, the control of the launch angle, and the like become unnecessary.

In the configuration in which the drive mechanism 60 includes the turning mechanism 62 and the two-dimensional moving mechanism (axis moving mechanism 70), when the X-ray generating unit 42 and the X-ray detecting unit 44 are turned, the X-ray generating unit 42 and the X-ray detecting unit 44 can be moved in the two-dimensional direction along the turning surfaces by the two-dimensional moving mechanism (axis moving mechanism 70). Consequently, the turning orbits of the X-ray generating unit 42 and the X-ray detecting unit 44 can be changed to another orbit other than the circular orbit. For example, the turning orbit can be set such that the X-ray detecting unit 44 approaches the surface of the head P in front of the head P and moves away from the surface of the head P in the lateral of the head P. Thus, it is easy to set the orbit in which the X-ray detecting unit 44 is brought as close as possible to the head P while avoiding the contact with the shoulder S.

In particular, when the two-dimensional moving mechanism is the axis moving mechanism 70 that moves the turning shaft 96 in the direction intersecting the axial direction of the turning axis X1, the turning shaft 96 is moved by the axis moving mechanism 70 in synchronization with the turning of the turning arm 40 by the turning mechanism 62, and the turning arm 40 is caused to perform the combined motion, so that the turning orbit of the X-ray detecting unit 44 can be changed.

<Modifications>

Figure 14:
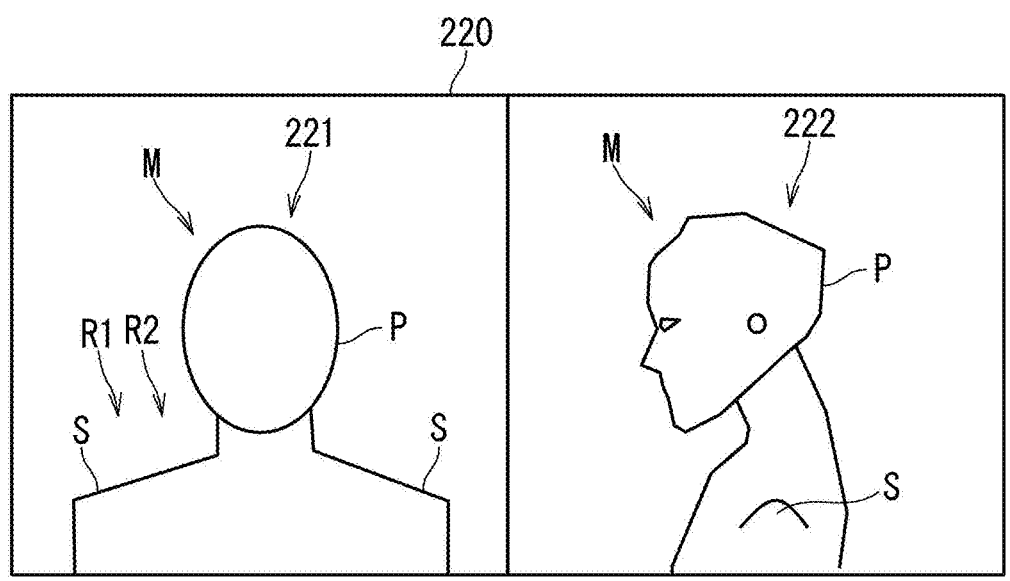
FIG. 14 is an explanatory view illustrating an image example for detecting a position of a shoulder.

Modifications of the first preferred embodiment will be described below. In the first preferred embodiment, the vertical displacement amount may be set based on a detection result from the detecting unit that detects the position of the shoulder S. For example, as illustrated in FIG. 14, the imaging apparatus 22 images the front and side surfaces of the imaging subject M. An imaging image 220 includes a front image 221 including the head P and the shoulder S. The imaging image 220 may include a side image 222 including the head P and the shoulder S. The imaging controller 100 executes image recognition processing such as edge extraction processing based on the imaging image 220 to extract an upper boundary or the like of the shoulder S. Then, the height position and the like of the shoulder S in the passage region of the set turning orbit R are recognized. Because the front image 221 and the side image 222 express the physical constitution of the imaging subject M, the imaging apparatus 22 is an example of a physical constitution detecting unit that detects the physical constitution of the imaging subject M. The imaging controller 100 may set the movement orbit of the X-ray detecting unit 44 according to the detected physical constitution. The imaging controller 100 controls the drive of the vertical drive unit 82 according to the detection result by the imaging apparatus 22. The imaging controller 100 determines whether the vertical movement avoiding the contact with the shoulder S is required according to the detection result of the imaging apparatus 22, and performs the control to add the vertical movement to the X-ray detecting unit 44 by the vertical drive unit 82 when it is determined that the vertical movement is required. For example, the imaging controller 100 calculates how much the X-ray detecting unit 44 rises with respect to the height position of the lower end of the X-ray detecting unit 44 initially set with respect to the imaging subject M in order to avoid the contact with the shoulder S. The vertical displacement amount of the X-ray detecting unit 44 is determined based on the calculation result, and the vertical displacement pattern can be set based on the vertical displacement amount to set the safe X-ray detection orbit. In this way, the setting of the height difference in the turning elevation orbit REL of the X-ray detecting unit 44 can be changed.

Figure 15:
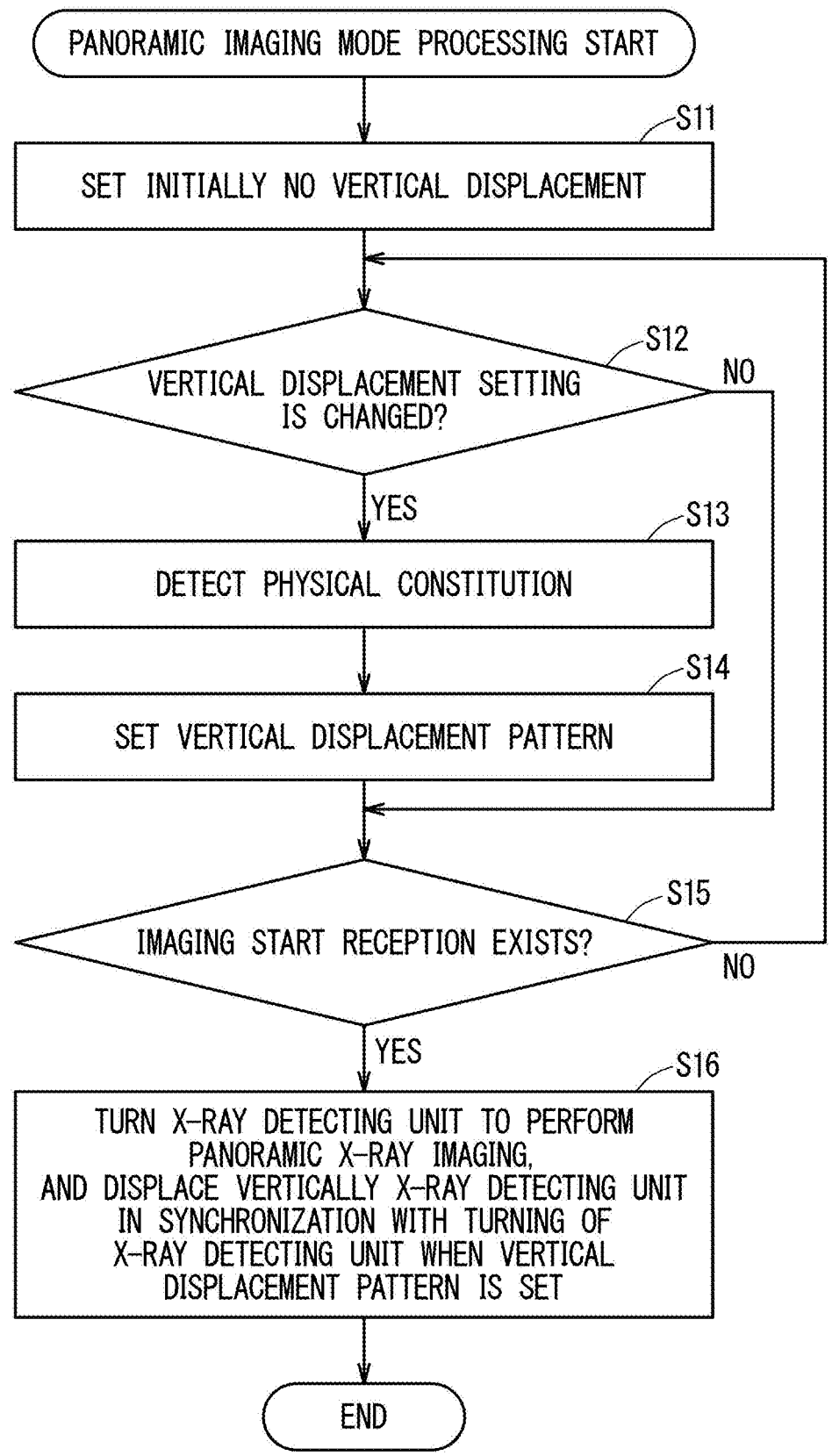
FIG. 15 is a flowchart illustrating an example of processing performed by a imaging controller according to a modification.

FIG. 15 is a flowchart illustrating an example of processing performed by the imaging controller 100 according to a modification.

Step S11 is similar to step S1. In step S12 after step S11, it is determined whether the setting of the vertical displacement amount is changed. When the instruction to change the setting of the vertical displacement amount is input according to the touch operation or the like to the operation display 110 or the like, it is determined that the vertical displacement amount setting is changed, and the processing proceeds to step S13. When the input of the setting changing instruction does not exist, the processing proceeds to step S15.

In steps S13 and S14, the physical constitution of the imaging subject M is detected by imaging the head P and the shoulder S using the imaging apparatus 22 that is the physical constitution detecting unit, and at least one of the presence or absence of the vertical movement and the amount of the vertical movement is determined according to the detected physical constitution of the imaging subject M.

That is, in step S13, the head P and the shoulder S that are held by the subject holding unit 32 are imaged by the imaging apparatus 22. For example, the X-ray detecting unit 44 may be turned along the turning orbit (orbit sufficiently away from the head P) that hardly contacts with the imaging subject M, and the image data obtained by imaging the head P from a plurality of spot directions may be used as the detection result. Because the image data includes the surface shapes of the head P and the shoulder S, the image data is an example of the physical constitution data including the physical constitutions of the head P and the shoulder S of the imaging subject M. For example, the imaging controller 100 executes the image recognition processing such as the edge extraction processing on the imaging image 120 to extract the upper boundary or the like of the shoulder S. Thus, the physical constitution of the imaging subject M can be grasped as data. The positional relationship of the imaging apparatus 22 with respect to the turning arm 40 and the X-ray detecting unit 44 can be known information. For this reason, the imaging range of the imaging apparatus 22 with respect to the turning arm 40 and the X-ray detecting unit 44 can also be the known information. Consequently, the boundary position of the shoulder S in the imaging image 120 can be obtained as the relative position with respect to the turning arm 40 and the X-ray detecting unit 44.

In step S14, the vertical displacement pattern is set based on the detected physical constitution. The setting of the vertical displacement pattern includes the presence or absence of the setting of the vertical displacement pattern that vertically displaces the X-ray detecting unit 44. The setting of the vertical displacement pattern also includes a setting of how much the X-ray detecting unit 44 is vertically displaced.

For example, the upper boundary position of the shoulder S at the position corresponding to the turning orbit R is specified based on the imaging image 120 (particularly, the front image 221). This boundary position is defined as a lower limit position of the lower end of the X-ray detecting unit 44 in the lateral of the head P. Based on the initial height position (for example, set as a position suitable for imaging the front of the dental arch Arc) of the X-ray detecting unit 44 set at the initial imaging, how much the X-ray detecting unit 44 needs to be moved upward from the initial position in front of the head P is calculated such that the lower end of the X-ray detecting unit 44 is disposed at the same position as or above the lower limit position in the lateral of the head P. When the required upward movement amount is "zero", the setting of the vertical displacement pattern is not required. When the required upward movement amount exceeds "zero", the vertical displacement pattern is set. The vertical displacement pattern may be set according to the magnitude of the required movement amount. For example, when the vertical displacement information 104b includes the plurality of vertical displacement patterns 104b1, 104b2, 104b3, the vertical displacement pattern having the smallest vertical movement amount among the vertical displacement patterns 104b1, 104b2, 104b3 having the required movement amount or more may be set as the vertical displacement pattern according to the detected physical constitution. When the vertical displacement pattern is expressed by a relational expression having the vertical movement amount as a variable, the vertical displacement pattern according to the detected physical constitution may be set by substituting the required movement amount as the vertical displacement amount into the relational expression.

The imaging apparatus 22 may perform the imaging of the head P and the shoulder S from a plurality of directions, and the imaging controller 100 may generate three-dimensional surface shape data representing the surface shapes of the head P and the shoulder S based on the imaging images from the plurality of directions. The imaging controller 100 can also specify the vertical position of the shoulder S in the turning orbit R based on the three-dimensional surface shape data.

The physical constitution detecting unit may be a mobile terminal device 300 having an imaging apparatus such as a smartphone or a tablet terminal apparatus (see FIG. 2). The mobile terminal device 300 performs the imaging of the image in which the head P, the shoulder S, and the reference region in the X-ray imaging apparatus 20 are imaged, and performs image processing or the like based on the imaging image, so that the surface position of the shoulder S in the X-ray imaging apparatus 20 can be recognized. Thus, similarly to the above, the vertical displacement pattern can be set according to the physical constitution.

Furthermore, for example, a visible light sensor or a laser sensor that detects the position of the shoulder S may be incorporated in the turning arm 40, and the physical constitution, particularly the position of the shoulder S may be detected based on the output of the sensor. The data including these detection results is an example of the physical constitution data. The position of the shoulder S is specified based on the detection results, so that the vertical displacement pattern can be set similarly to the above.

When it is determined in step S12 that the change of the vertical displacement amount setting does not exist, and after the vertical displacement pattern is set in step S14, the processing proceeds to step S15. In step S15, similarly to step S4, it is determined whether the reception of imaging start exists. The processing returns to step S12 when it is determined that the reception of the imaging start does not exist, and the processing proceeds to step S16 when it is determined that the reception of the imaging start exists. When it is determined that the imaging start reception does not exist, the processing may return to an appropriate process from immediately after step S12 to immediately before step S15 itself without returning to step S12.

In step S16, similarly to step S5, the panoramic X-ray imaging is performed while the X-ray detecting unit 44 is turned. At this time, when the vertical displacement pattern is set, the X-ray detecting unit 44 is vertically displaced in synchronization with the turning of the X-ray detecting unit 44. Consequently, the X-ray detecting unit 44 can be turned to perform the panoramic X-ray imaging while the contact of the X-ray detecting unit 44 with the shoulder S is avoided according to the individual physical constitution of the imaging subject M.

According to the modification, the imaging controller 100 controls the drive of the vertical drive unit 82 according to the detection result by the imaging apparatus 22 that is an example of the physical constitution detecting unit. Thus, the operation of the vertical drive unit 82 can be controlled according to the physical constitution of the imaging subject M, and the shoulder hitting of the X-ray detecting unit 44 can be prevented.

In the above example, the description has been made assuming that the vertical position when the X-ray detecting unit 44 passes through the front portion of the head P is initially set by the user or the like. The position of the jaw chip may be specified based on the side image and the like, and the vertical position when the X-ray detecting unit 44 passes through the front portion of the head P may be set based on the position of the jaw chip. For example, the vertical position when the X-ray detecting unit 44 passes through the front portion of the head P may be set such that the lower end of the X-ray detecting unit 44 or a lower edge of the detection surface of the X-ray detector 45 is matched with the position of the jaw chip.

According to this modification, the operation of the vertical drive unit 82 can be controlled according to the physical constitution of the imaging subject M, and the shoulder hitting of the X-ray detecting unit 44 can be prevented. In particular, the operation of the vertical drive unit 82 is controlled according to the detection result of the imaging apparatus 22 that is an example of the physical constitution detecting unit, so that the performance of the panoramic X-ray imaging can be contributed to by preventing the shoulder hitting of the X-ray detecting unit 44 while the vertical displacement amount of the X-ray detecting unit 44 is reduced as much as possible.

For example, it is conceivable that the imaging controller 100 determines whether the vertical movement avoiding the contact with the shoulder S is required according to the detection result of the imaging apparatus 22 that is an example of the physical constitution detecting unit and the vertical drive unit 82 adds the vertical movement to the X-ray detecting unit 44 when the vertical movement is determined to be required. Thus, the panoramic X-ray image imaged without vertically displacing the X-ray detecting unit 44 is obtained depending on the physical constitution (for example, see the imaging subject M(1)). Consequently, the situation in which the lower portion of the imaging target region including the dental arch Arc or the like is not imaged in the panoramic X-ray image is avoided in the panoramic X-ray image.

It is conceivable that the imaging controller 100 determines the vertical displacement amount avoiding the contact with the shoulder S according to the detection result of the imaging apparatus 22 that is an example of the physical constitution detecting unit and the vertical drive unit 82 adds the vertical movement to the X-ray detecting unit 44 similarly to the vertical displacement patterns 104*b*1, 104*b*2, 104*b*3 according to the determined vertical displacement amount. Thus, the panoramic X-ray imaging can be performed with an appropriate amount according to the physical constitution, for example, the vertical displacement amount as small as possible within the range in which the contact with the shoulder S is avoided according to the physical constitution. In particular, when the panoramic X-ray imaging is performed with the X-ray detecting unit 44 extremely close to the head P within 10 cm, the X-ray detecting unit 44 easily hits the shoulder S. In such a case, it is effective to be able to set the vertical displacement amount as small as possible within the range in which the contact with the shoulder S can be avoided.

In the modification, the presence or absence of the setting of the vertical displacement pattern and the example of setting the vertical displacement amount in the case of setting the vertical displacement pattern according to the detection result of the physical constitution have been described. However, only the presence or absence of the setting of the vertical displacement pattern may be performed according to the detection result of the physical constitution, or only the vertical displacement amount may be set on the premise of the vertical displacement.

In the flowchart of FIG. 15, the input of the instruction to change the vertical displacement amount setting is received in step S12, and when the input of the instruction to change the vertical displacement amount setting exists, the physical constitution is detected in step S13 and the vertical displacement pattern based on the physical constitution is set in step S14. However, the progress may be fully automatic. That is, step S12 may be omitted, first the physical constitution may be detected in step S13, the imaging controller 100 may automatically determine whether the vertical displacement amount setting change is required, the vertical displacement amount setting may be changed when the vertical displacement amount setting change is required, and the currently-set vertical displacement pattern setting may be maintained when the vertical displacement amount setting change is not required. In this case, a loop returning to immediately before step S15 may be used when the negative determination is made in step S15. Furthermore, the initial setting without vertical displacement may be omitted. In this case, step S11 is omitted. For example, such a progress can be used when the specification is set such that the setting of the previous shooting is left.

Second Preferred Embodiment

An X-ray imaging apparatus 200 according to a second preferred embodiment will be described. In the description of the second preferred embodiment, the same components as those described in the first preferred embodiment are denoted by the same reference numerals, and the description thereof will be omitted. FIG. 16 is a block diagram illustrating an example of an electric configuration of the X-ray imaging apparatus 200.

In the second preferred embodiment, an example in which a first turning orbit R1 and a second turning orbit R2 can be set as the turning orbit R of the X-ray detecting unit 44 in the panoramic X-ray imaging with respect to the same imaging subject M will be described. That is, depending on the case of the imaging subject M or the like, the panoramic X-ray imaging is performed by bringing the X-ray detecting unit 44 close to the head P, whereby the case where the clearer panoramic X-ray image is obtained is generated. In such a case, when the turning orbit in which the X-ray detecting unit 44 is brought close to the head P can be set within the range in which the contact between the X-ray detecting unit 44 and the shoulder S can be avoided according to the physical constitution of the imaging subject M, the panoramic X-ray image can be made clearer.

An example in which the hitting of the shoulder S is avoided by vertically displacing the X-ray detecting unit 44 when the turning orbit in which the X-ray detecting unit 44 is brought close to the head P is set is illustrated in the second preferred embodiment.

In the X-ray imaging apparatus 200, in addition to the processing function of the imaging program 104*a*, the imaging program 204*a* stored in the storage 104 can set the first turning orbit R1 and the second turning orbit R2 as the panoramic turning orbits of the X-ray detecting unit 44 with respect to the same imaging subject, and has a function of selectively setting one of the first turning orbit R1 and the second turning orbit R2 as the actual turning orbit in the panoramic X-ray imaging. In addition, the storage 104 stores first turning orbit information 204*b* and second turning orbit information 204*c* as the turning orbit information 204. The first turning orbit information 204*b* and the second turning orbit information 204*c* are information determining the orbit of the X-ray detecting unit 44 when the panoramic X-ray imaging is performed. The first turning orbit information 204*b* and the second turning orbit information 204*c* define different orbits. In addition to the functions in the first preferred embodiment, the processor 102 includes an orbit setting unit 102*g* that sets the turning orbit based on the first turning orbit information 204*b* and the second turning orbit information 204*c* by executing processing according to the imaging program 204*a*. The second turning orbit R2 may be set to have the higher approach degree than the first turning orbit R1 in at least a part thereof.

The second turning orbit R2 can be set so that the X-ray detecting unit 44 passes over the shoulder S or passes over at least a part of the shoulder S in a timing the X-ray detecting unit 44 comes to the lateral of the head P. At this setting, the placement of the X-ray detecting unit 44 on X-Y coordinate in the timing the X-ray detecting unit 44 comes to the lateral of the head P can be set to a position of a shoulder S of a standard physical constitution of the imaging subject M, or can be set to a position of a shoulder of an individual physical constitution.

Further, the first turning orbit R1 can be set so that the X-ray detecting unit 44 does not pass over the shoulder in a timing the X-ray detecting unit 44 comes to the lateral of the head P.

The first turning orbit information 204*b* and the second turning orbit information 204*c* are information defining the turning orbit of the X-ray detecting unit 44. As described above, the movement of the X-ray detecting unit 44 is the combined movement of the turning operation of the X-ray detecting unit 44 by the turning mechanism 62 and the movement operation of the turning shaft 96 by the axis moving mechanism 70 during the turning by the turning mechanism 62. For this reason, for example, the first turning orbit information 204b and the second turning orbit information 204c may be information in which the turning operation of the X-ray detecting unit 44 by the turning mechanism 62 and the movement path of the turning shaft 96 by the axis moving mechanism 70 with respect to the turning operation are associated with each other. For example, the turning operation of the X-ray detecting unit 44 by the turning mechanism 62 may be expressed as a rotation angle of the X-ray detecting unit 44 based on any initial angle. For example, the movement path of the turning shaft 96 may be expressed by data defining a change in the rotation direction and the rotation speed of the X-axis drive motor 76a and the Y-axis drive motor 76b that move the turning shaft 96, a data row of the XY-coordinate defining the position of the turning shaft 96, a relational expression using the x-coordinate and the y-coordinate as variables, or the like. The support controller 102a can turn the X-ray detecting unit 44 along the first turning orbit R1 defined in the first turning orbit information 204b or the second turning orbit R2 defined in the second turning orbit information 204c by controlling the turning mechanism 62 and the axis moving mechanism 70 based on the first turning orbit information 204b or the second turning orbit information 204c.

Figure 17A:
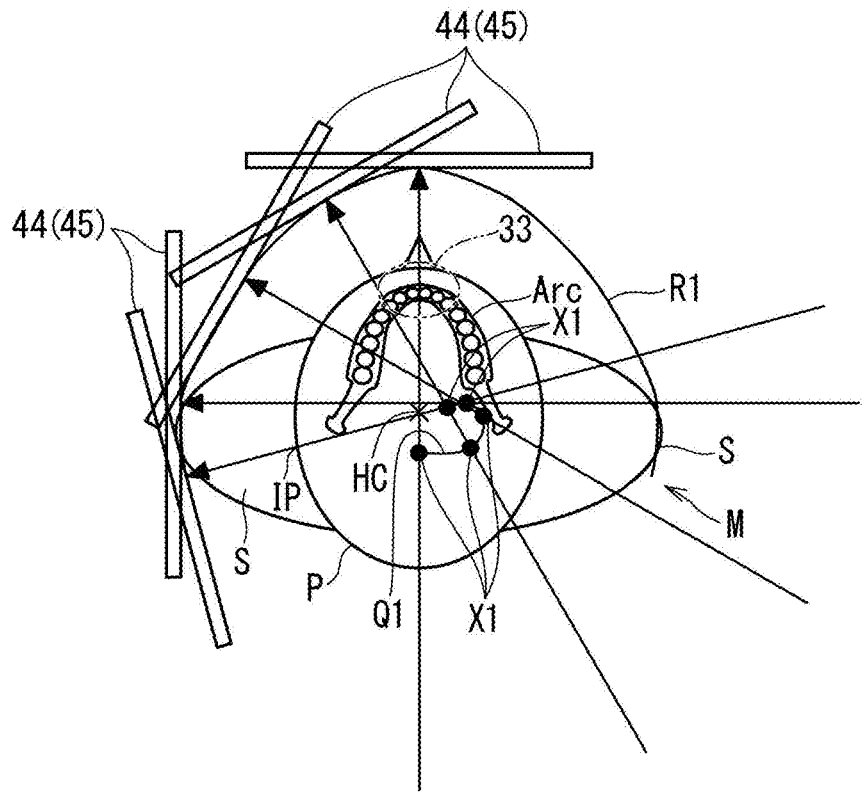
FIGS. 17A and 17B are explanatory views each illustrating an example of a second turning orbit.
Figure 17B:
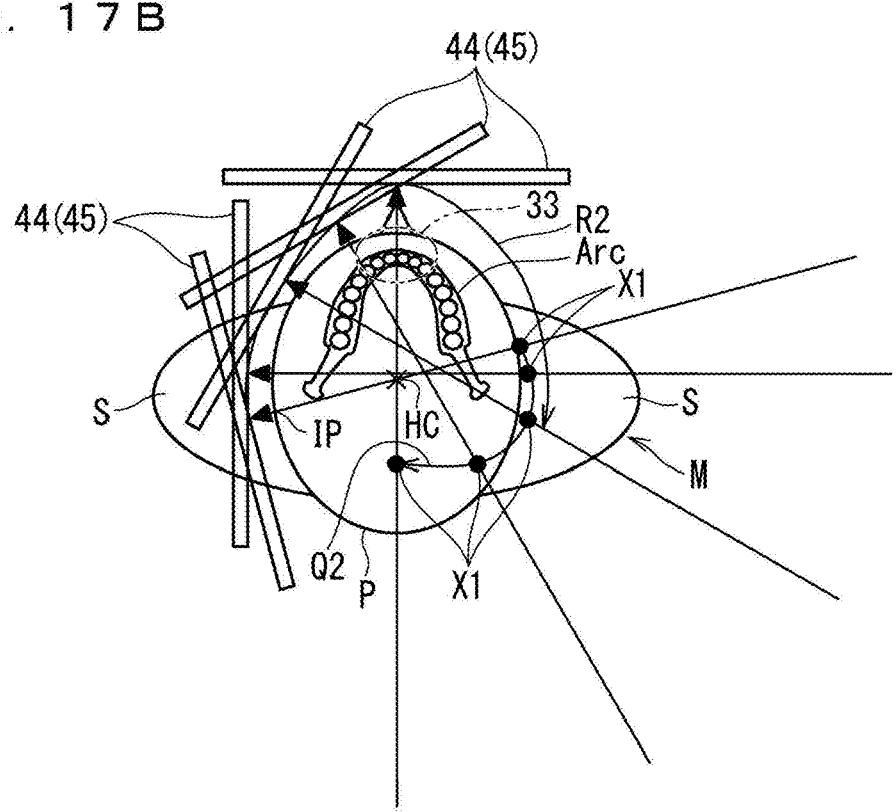

Examples of the first turning orbit R1 and the second turning orbit R2 will be described. FIGS. 17A and 17B illustrate examples in which the first turning orbit R1 and the second turning orbit R2 are set as the turning orbit R. The turning orbit R1 in FIG. 17A is an example of the first turning orbit R1. FIG. 17B illustrates an example of the second turning orbit R2. FIGS. 17A and 17B illustrate the shape of the head P and the shape of the shoulder S. The shapes of the head P and the shoulder S are standard.

The first turning orbit R1 and the second turning orbit R2 are arc-shaped lines along the outer peripheral side of the dental arch Arc. The first turning orbit R1 and the second turning orbit R2 may be set in the range in which the X-ray transmitted through the front tooth and the molar in the dental arch and the region including the vicinity of the mandibular angle from the temporomandibular joint can be detected. From this viewpoint, the first turning orbit R1 and the second turning orbit R2 may be an arc-shaped orbit in the range (for example, the range of ±115°) exceeding 90° to the left and right with the front portion at the center in the left-right direction of the head P as the center.

The second turning orbit R2 is set to an orbit closer to the head surface than the first turning orbit R1 in at least one of the front (at least the front in the center in the left-right direction of the head P) of the head P and the lateral (at least the left and right in the center in the front-rear direction of the head P). For this reason, the X-ray detecting unit 44 turning on the second turning orbit R2 can detect the X-ray closer to the dental arch Arc that is the region of interest. In the illustrated example, the second turning orbit R2 is an orbit closer to the head surface than the first turning orbit R1 in both the front and the lateral of the head P.

As illustrated in FIGS. 17A and 17B, in order to move the X-ray detecting unit 44 along the first turning orbit R1 or the second turning orbit R2, for example, when the X-ray detecting unit 44 turns around the turning shaft 96, the turning shaft 96 may be moved by the axis moving mechanism 70. For example, the position of the turning shaft 96 may be adjusted according to the distance of the first turning orbit R1 or the second turning orbit R2 with respect to the surface of the head P. For example, in a portion of the turning orbits R1, R2 that approaches the surface of the head P, the movement approaching the surface is implemented by moving the turning shaft 96 in the reverse irradiation direction, and in a portion of the turning orbits R1, R2 that moves away from the surface of the head P, the movement moving away from the surface is implemented by moving the turning shaft 96 in the forward irradiation direction.

A movement orbit Q2 of the turning shaft 96 corresponding to the second turning orbit R2 is set at a position advanced in the reverse irradiation direction in the rear and the lateral of the head P with respect to a movement orbit Q1 of the turning shaft 96 corresponding to the first turning orbit R1. Thus, the X-ray detecting unit 44 moving along the second turning orbit R2 comes closer to the surface of the head P than the X-ray detecting unit 44 moving along the first turning orbit R1 in the front and lateral of the head P.

The first turning orbit R1 may be an orbit adapted to the shape of the standard head P. That is, the first turning orbit R1 may be set to the path in which the X-ray detecting unit 44 can turn around the head P without contacting with the standard head P in consideration of the shape and size of the X-ray detecting unit 44 with respect to the standard head P.

Here, the shape of the standard head P may mean an average head shape in a country or an area where the X-ray imaging apparatus 20 is used regardless of an adult, a child, a gender, or the like. The shape of the standard head P may mean an average head in a country or region where the X-ray imaging apparatus 20 is used for the adult in the country or region. The standard head P has the standard shape and standard size of the dental arch Arc in the head P, and thus the first turning orbit R1 may be set as the turning in the range in which the dental arch Arc can exist. Needless to say, a plurality of groups may be distinguished, and for example, the adult and the child may be distinguished and adapted to an average head shape for each group.

The second turning orbit R2 may have a similar shape and a small shape with respect to the first turning orbit R1. In addition, a degree of contraction of the left-right width (X direction width) of the second turning orbit R2 with respect to the left-right width (X direction width) of the first turning orbit R1 is larger than a degree of contraction of the front-back length (Y direction length) of the second turning orbit R2 with respect to the front-back length (Y direction length) of the first turning orbit R1. Consequently, the second turning orbit R2 may have the shape contracted more in the left-right (X direction) than the front-back (Y direction) with respect to the first turning orbit R1.

The second turning orbit R2 is also an orbit closer to the chin rest 33 than the first turning orbit R1 in front of the chin rest 33 that is an example of the front tooth region fixing portion. The second turning orbit R2 is also an orbit closer to the surface of the head P than the first turning orbit R1 in front of the head P. The second turning orbit R2 is also an orbit closer to the chin rest 33 than the first turning orbit R1 in the left-right direction, namely, in the X direction of the imaging subject M held by the subject holding unit 32.

In relation to the shape of the head P, the second turning orbit R2 may be an orbit passing through the position within 10 cm from the surface of the head P in front of the head P (at least in front of the center in the left-right direction (X direction) of the head P).

The second turning orbit R2 may be an orbit in which the partial orbit in the front range of the front tooth region Pa comes closer to the surface of the head P than the partial orbit in other ranges. In other words, the second turning orbit R2 may be an orbit in which a region portion at the center in the left-right direction (X direction) of the head P comes closest to the surface of the head P with respect to other regions.

In these cases, the shoulder S with which the X-ray detecting unit 44 easily comes into contact does not exist in front of the head P, so that the X-ray detecting unit 44 can easily approach the head P without coming into contact with the imaging subject M.

Furthermore, the second turning orbit R2 may be an orbit passing through the position within 10 cm from the surface of the head P over the entire circumference of the head P. In this case, whether the X-ray detecting unit 44 comes into contact with the shoulder S may be checked according to the shape of the shoulder S of the imaging subject M. When there is a possibility that the X-ray detecting unit 44 comes into contact with the shoulder S, it is conceivable to stop the setting of the second turning orbit R2 or adjust the vertical position of the X-ray detecting unit 44 during the turning along the second turning orbit R2. A modification of this case will be described later.

At least one of the first turning orbit R1 and the second turning orbit R2 may be an orbit in which the distance to the surface of the head P in the lateral of the head P is larger than the distance to the surface of the head P in front of the head P. In other words, at least one of the first turning orbit R1 and the second turning orbit R2 may be a forward approach orbit. That is, at least one of the first turning orbit R1 and the second turning orbit R2 may be an orbit in which the distance to the surface of the head P at the center in the front-back direction (Y direction) of the head P is longer than the distance to the surface of the head P at the center in the left-right direction (X direction) of the head P. More specifically, at least one of the first turning orbit R1 and the second turning orbit R2 may be an orbit in which the distance to the side surface of the head P at the center in the front-back direction (Y direction) of the head P in the portion where the X-ray detecting unit 44 faces the side portion of the head P in the turning orbit is longer than the distance to the front surface of the head P at the center in the left-right direction (X direction) of the head P in the portion where the X-ray detecting unit 44 faces the front portion of the head P in the turning orbit.

The first turning orbit R1 may be set as illustrated in FIG. 17A, and the second turning orbit R2 may be set as illustrated in FIG. 9. The approach degree of the second turning orbit R2 in the lateral of the head may be set higher than the approach degree of the first turning orbit R1. In this case, a height difference FS2 of the second turning orbit R2 may be larger than a height difference FS1 of the first turning orbit R1. Furthermore, the difference between the height difference FS2 of the second turning orbit R2 and the height difference FS1 of the first turning orbit R1 may be increased or decreased depending on the physical constitution. For example, for the imaging subject M(3) having the square shoulder, the difference between the height difference FS2 of the second turning orbit R2 and the height difference FS1 of the first turning orbit R1 may be made larger than that of the imaging subject M(1) having a standard falling shoulder.

Here, a portion protruding from roundness of the head as viewed in the —Z direction, such as the nose or the ear or both, is referred to as a head protrusion. When the distance between the head and the X-ray detecting unit 44 is considered, the distance may be considered as the distance between the surface including the head projection, and the distance may be considered as the distance between the roundness of the head assuming that the head protrusion does not exist. Only a part of the plurality of head protrusions may be considered not to exist, for example, it may be considered that the nose does not exist.

The protrusion of the trunk in the front lower portion of the head P is hardly observed, whereas the shoulder S can be observed in the lateral lower portion of the head P. For this reason, when the X-ray detecting unit 44 passes through the lateral of the head P, there is a possibility that the X-ray detecting unit 44 comes into contact with the shoulder S. In general, the upper surface of the shoulder S has the shape that goes downward with increasing distance from the surface of the head P. Accordingly, in the lateral of the head P, the X-ray detecting unit 44 passes through the position away from the surface of the head P, so that the X-ray detecting unit 44 hardly comes into contact with the shoulder S.

Figure 18:
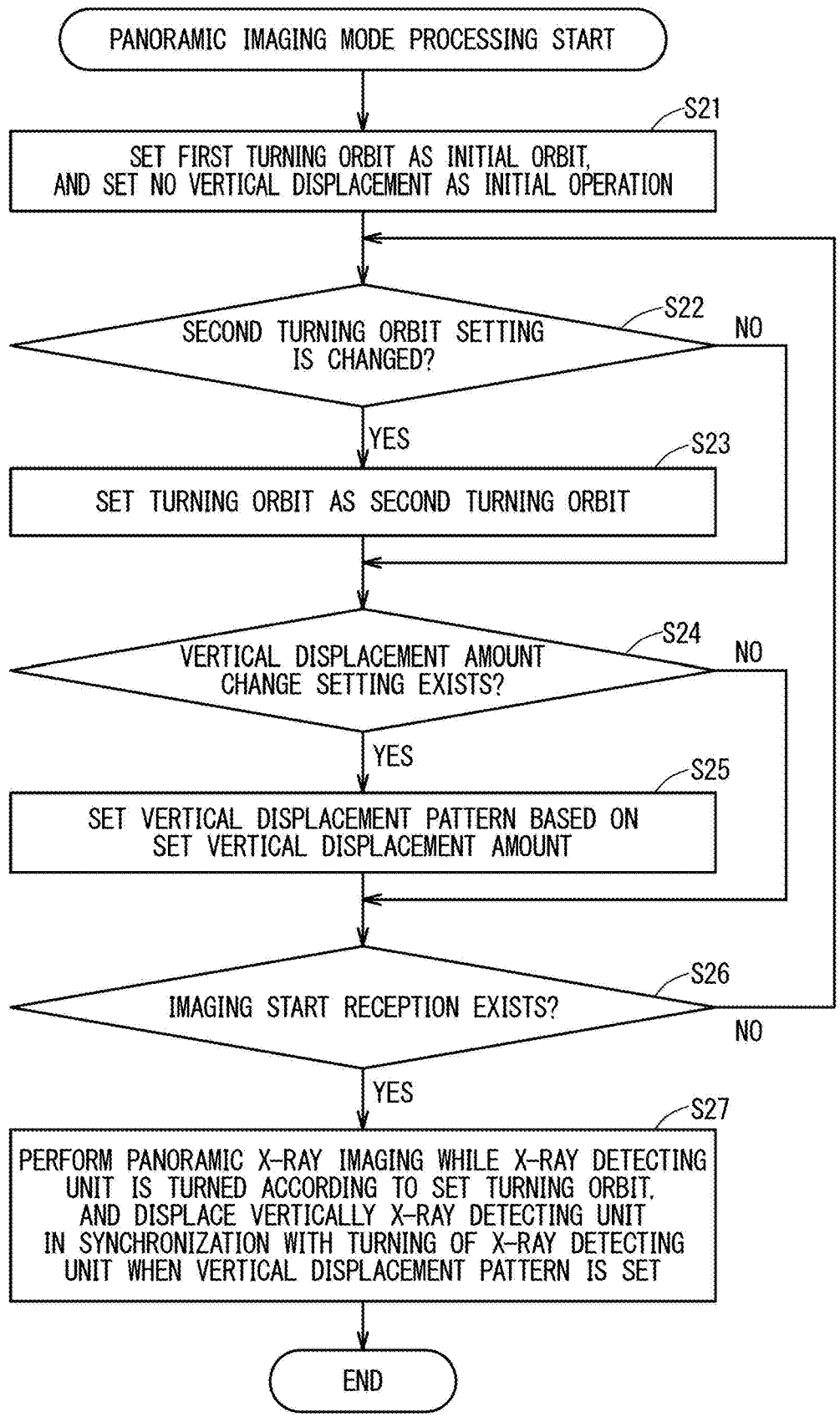
FIG. 18 is a flowchart illustrating an example of processing performed by the turning controller.

FIG. 18 is a flowchart illustrating an example of processing performed by the imaging controller 202 of the X-ray imaging apparatus 200.

When the panoramic imaging mode processing is started, in step S21, the first turning orbit R1 is set as the initial orbit or the default orbit based on the first turning orbit information 204b. The first turning orbit R1 may be a general-purpose turning orbit conventionally adopted in the panoramic X-ray imaging apparatus. For this reason, the panoramic X-ray imaging in which the X-ray detecting unit 44 is turned along the first turning orbit is performed when the special instruction on the turning orbit does not exist. In addition, no vertical displacement is set as the initial operation. For this reason, the X-ray detecting unit 44 performs the panoramic X-ray imaging without the vertical displacement when the special instruction to change the vertical displacement amount does not exist.

In next step S22, the presence or absence of the setting change to the second turning orbit R2 is checked. For example, the setting change to the second turning orbit R2 is performed through the operation display 110. For example, an icon for setting change to the second turning orbit R2 is displayed on the operation display 110, and the setting change to the second turning orbit is received by touching the icon. When it is determined that the setting change to the second turning orbit R2 exists, the processing proceeds to step S23. When it is determined that the setting change does not exist, the processing skips step S23 and proceeds to step S24.

In step S23, the second turning orbit R2 is set as the turning orbit based on the second turning orbit information 204c. Then, the processing proceeds to step S24.

In step S24, similarly to step S2, it is determined whether the vertical displacement amount is set. When it is determined that the setting of the vertical displacement amount is changed, the processing proceeds to step S25. When it is determined that the setting is not changed, the processing skips step S25 and proceeds to step S26.

In step S25, the vertical displacement pattern is set based on the set vertical displacement amount. When the approach degree of the second turning orbit R2 in the lateral of the head is set higher than the approach degree of the first turning orbit R1, the second turning orbit R2 in which the height difference FS2 is larger than the height difference FS1 can be set or selected such that the height difference FS2 of the second turning orbit R2 can be made larger than the height difference FS1 of the first turning orbit R1. The height difference FS2 of the second turning orbit R2 may be configured to be larger than the height difference FS1 of the first turning orbit R1 based on the detection result of the imaging apparatus 22 that is the physical constitution detecting unit.

The vertical displacement pattern of the second turning orbit R2 may be chosen from the plurality of vertical displacement patterns.

Further, the vertical displacement pattern of the first turning orbit R1 also may be chosen from the plurality of vertical displacement patterns.

In next step S26, similarly to step S4, it is determined whether the reception of imaging start exists. When it is determined that the imaging start reception does not exist, the processing returns to step S22, and the pieces of processes after step S22 are repeated. When it is determined that the imaging start reception exists, the processing proceeds to step S27. When it is determined that the imaging start reception does not exist, the processing may return to appropriate processing from immediately after step S22 to immediately before step S26 itself without returning to step S22.

In step S27, the panoramic X-ray imaging is performed while the X-ray detecting unit 44 is turned according to the set turning orbit. That is, the X-ray detecting unit 44 is turned along the first turning orbit R1 or the second turning orbit R2 by controlling the turning mechanism 62 and the axis moving mechanism 70 according to the set first turning orbit information 204b or second turning orbit information 204c. In the panoramic X-ray imaging, because the entire turning arm 40 turns and moves, the X-ray generating unit 42 also turns. At this time, when the vertical displacement pattern is set, the vertical drive unit 82 is controlled to move the turning arm 40 in the vertical direction in synchronization with the turning of the X-ray detecting unit 44, thereby vertically displacing the X-ray detecting unit 44 according to the vertical displacement pattern. At this time, by controlling the holding-unit drive unit 36, the subject holding unit 32 may be displaced upside down with respect to the moving direction of the turning arm 40, and the height position of the subject holding unit 32 may be kept constant. Thus, the X-ray imaging data is obtained. The image processing apparatus 180 generates the panoramic X-ray image based on the X-ray imaging data.

<Panoramic X-Ray Imaging Example>

Figure 19:
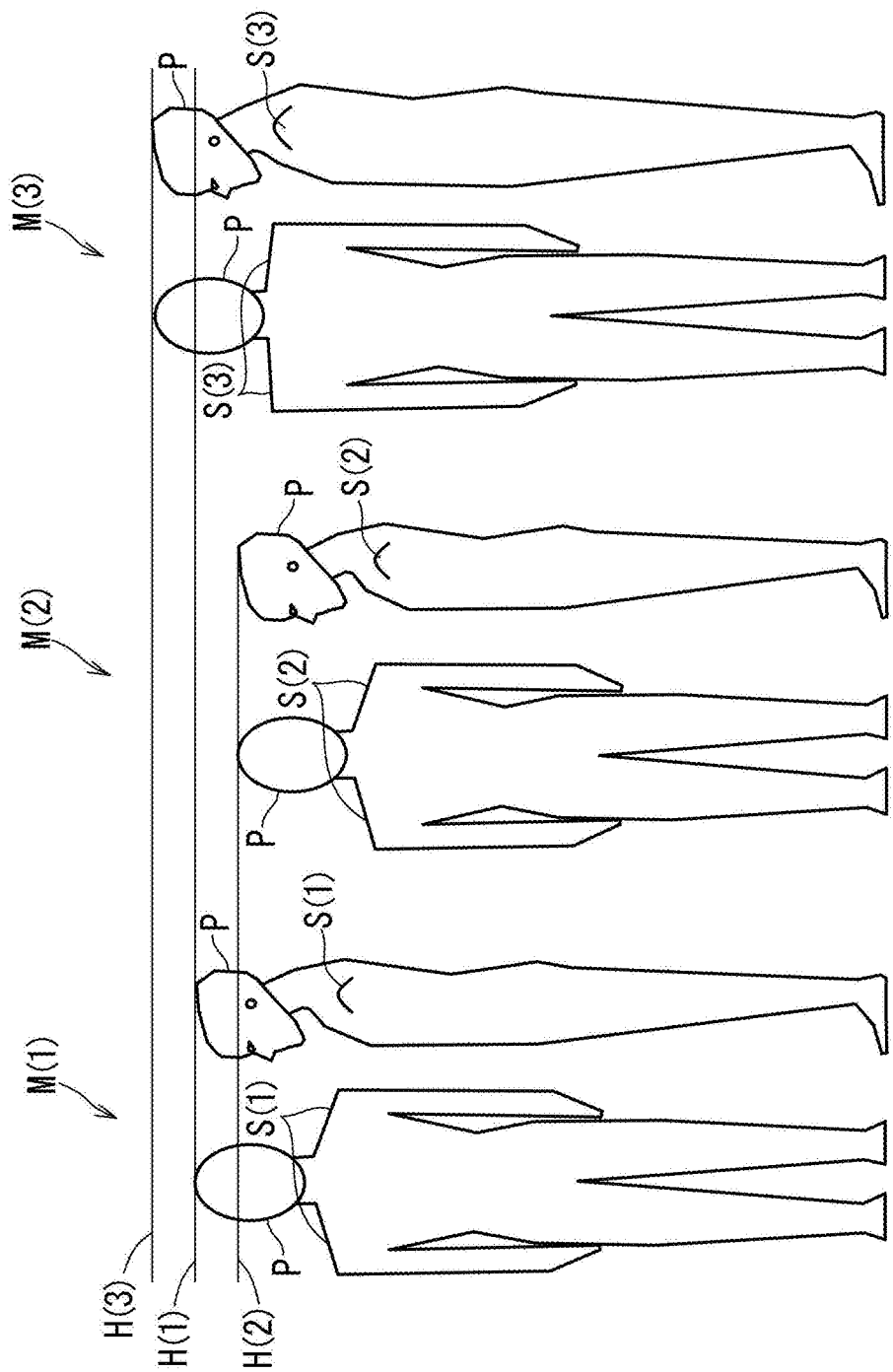
FIG. 19 is an explanatory view illustrating physical constitution examples of the plurality of imaging subjects.

As illustrated in FIG. 19, the panoramic X-ray imaging will be described with the imaging subject M(1), M(2), M(3) having different physical constitutions as an example. The imaging subject M(1), M(2) have different heights, and the height H(1) of the imaging subject M(1) is larger than the height H(2) of the imaging subject M(2). The imaging subjects M(1), M(2) have the shoulders S(1), S(2) that are normally lowered with respect to the head P. The height H(3) of the imaging subject M(3) is larger than the heights H(1), H(2) of the imaging subjects M(1), M(2). A shoulder S(3) of the imaging subject M(3) is a square shoulder. The relative position of the shoulder S(3) with respect to the head P of the imaging subject M(3) is higher than the relative positions of the shoulders S(1), S(2) with respect to the head P of the imaging subjects M(1), M(2).

It is considered that the panoramic X-ray imaging is performed while the X-ray detecting unit 44 is turned along the first turning orbit R1.

Figure 20:
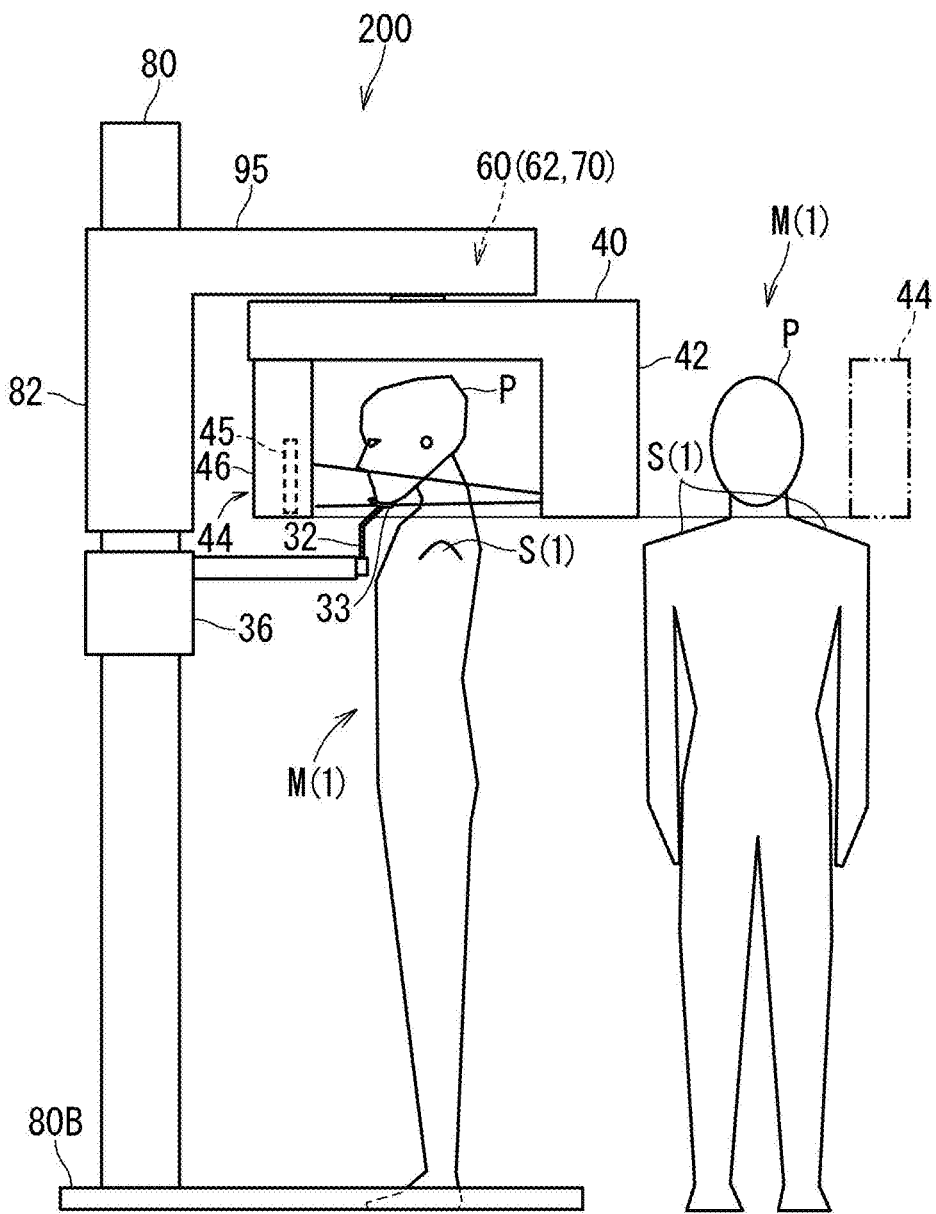
FIG. 20 is an explanatory view illustrating a positional relationship between the X-ray detecting unit and the housing with respect to the imaging subject during the panoramic imaging by the first turning orbit.

When the imaging subject M(1) is targeted, as illustrated in FIG. 20, the X-ray detecting unit 44 passes through the position away from the head P even in the lateral of the head P. At the position away from the lateral of the head P according to the first turning orbit R1, the shoulder S(1) is located below the jaw chip or the like of the head P. Thus, the X-ray detecting unit 44 hardly contacts with the shoulder S(1) even in the lateral of the head P. Consequently, even when the X-ray detecting unit 44 is not vertically displaced, the X-ray detecting unit 44 can be turned around the head P to perform the panoramic X-ray imaging.

Figure 21:
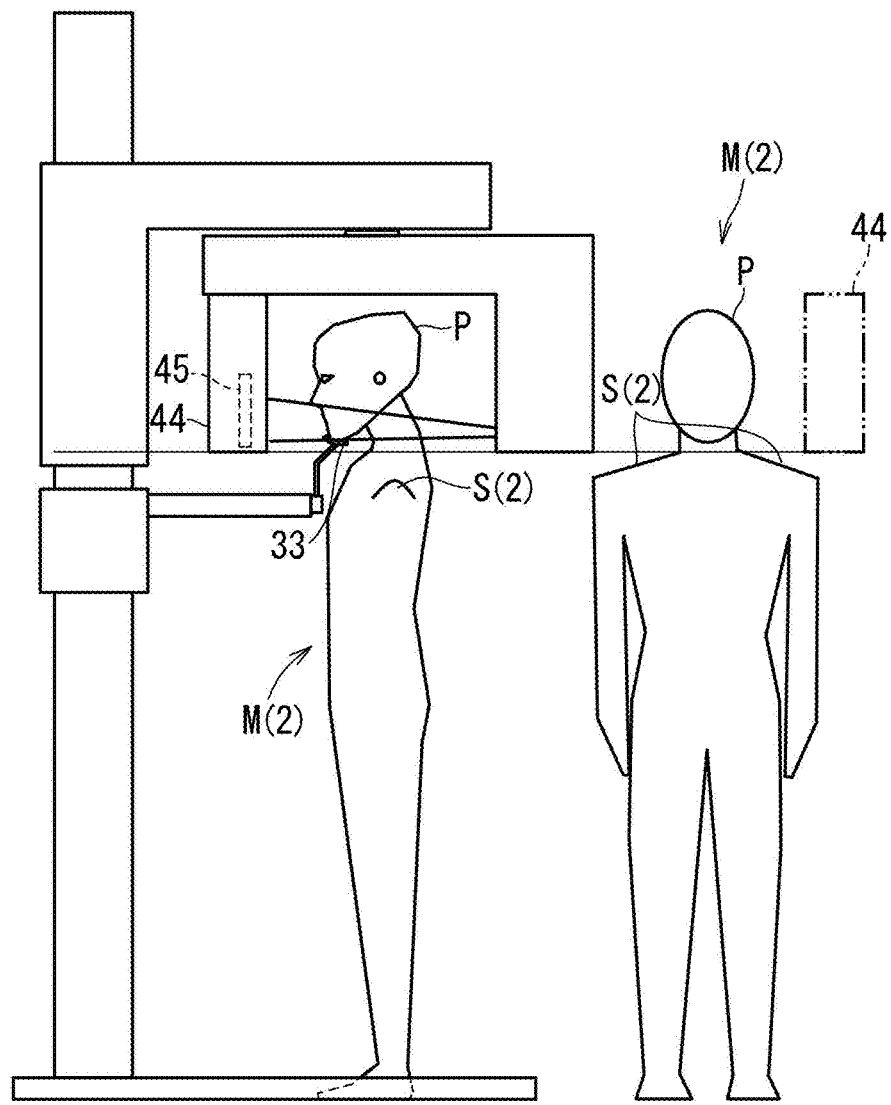
FIG. 21 is an explanatory view illustrating the positional relationship between the X-ray detecting unit and the housing with respect to the imaging subject during the panoramic imaging by the first turning orbit.

When the imaging subject M(2) is targeted, as illustrated in FIG. 21, the turning arm 40 that holds the X-ray generating unit 42 and the X-ray detecting unit 44 and the subject holding unit 32 are located below the case in FIG. 20 according to the height H(2) of the imaging subject M(2). In this state, the panoramic X-ray imaging can be performed similarly to the case in FIG. 19.

Figure 22:
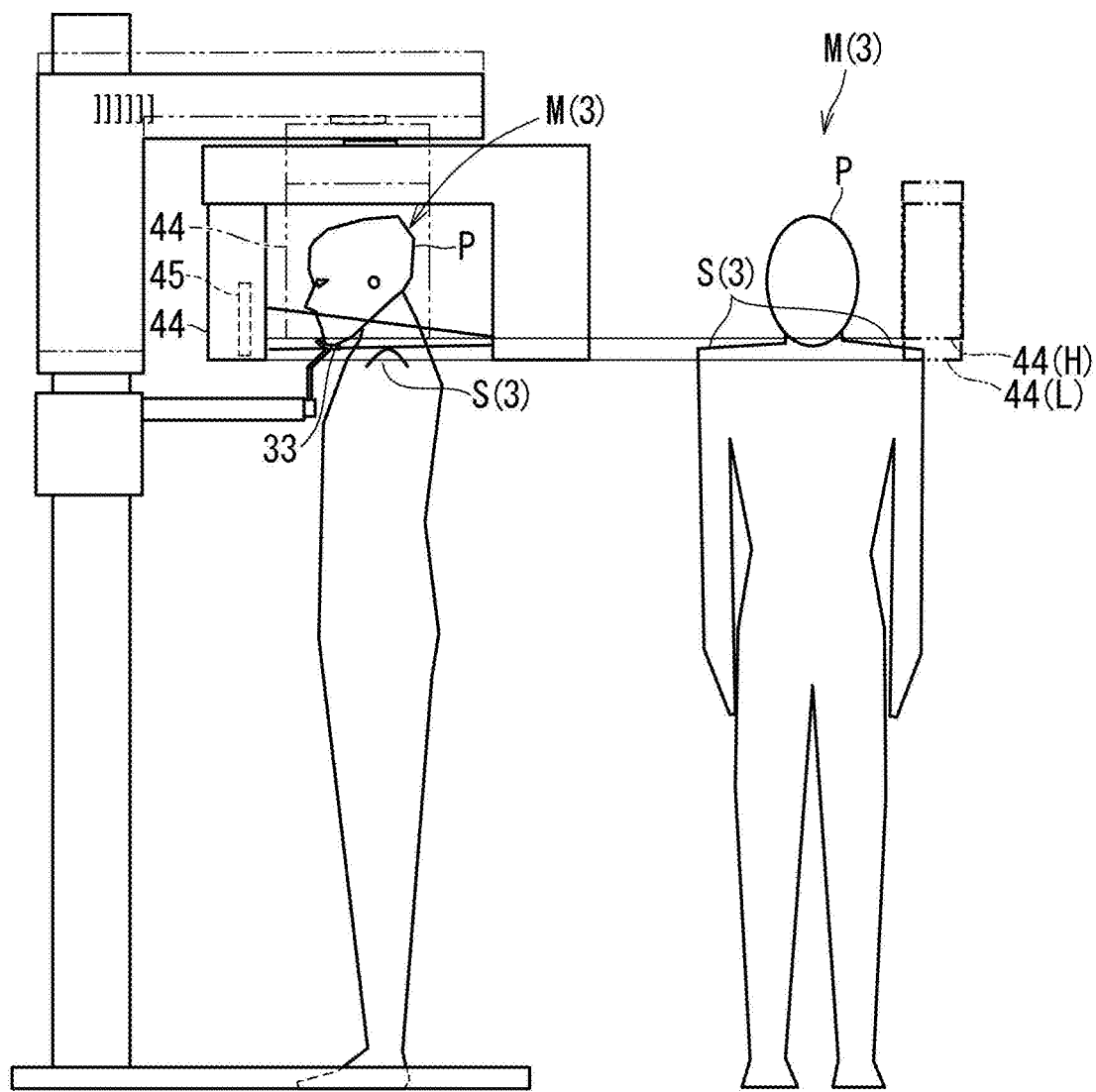
FIG. 22 is an explanatory view illustrating the positional relationship between the X-ray detecting unit and the housing with respect to the imaging subject during the panoramic imaging by the first turning orbit.

When the imaging subject M(3) is targeted, as illustrated in FIG. 22, the X-ray detecting unit 44 passes through the position away from the head P even in the lateral of the head P. When the imaging subject M(3) has the physical constitution such as the square shoulder, there is a possibility that the shoulder S(3) is located in the vicinity of the height position of the jaw chip or the like of the head P even at the position away from the lateral of the head P(1) according to the first turning orbit R1.

In this case, there is a possibility that the X-ray detecting unit 44 comes into contact with the shoulder S(3) in the lateral of the head P (see the position of the X-ray detecting unit 44(L) in FIG. 22). In such a case, it is also conceivable to perform the panoramic X-ray imaging without the vertical displacement while the X-ray detecting unit 44 is disposed at the height position (see the lowermost end position of an X-ray detecting unit 44(H)) that is not in contact with the shoulder S(3) in the state where the X-ray detecting unit 44 is located in the lateral of the head P. However, in this case, the lowermost end of the X-ray detecting unit 44 is located above the jaw chip, and there is a possibility that the front lower end of the dental arch Arc may not be imaged in the panoramic X-ray image.

Accordingly, the vertical displacement pattern is set as described in steps S24, S25, and the X-ray detecting unit 44 is vertically displaced such that the X-ray detecting unit 44 becomes lower in front of the head P and becomes higher in the lateral of the head P as described in step S27. Consequently, the X-ray detecting unit 44 can be turned along the first turning orbit R1 while avoiding the contact of the X-ray detecting unit 44 with the shoulder S. Consequently, the panoramic X-ray image in which the front lower end of the dental arch Arc is imaged while avoiding the contact of the X-ray detecting unit 44 with the shoulder S(3) can be generated.

Consequently, when the X-ray detecting unit 44 turns along the first turning orbit R1, the panoramic X-ray imaging can be performed while the X-ray detecting unit 44 is not vertically displaced (in the case of the imaging subjects M(1), M(2)) or is vertically displaced (in the case of the imaging subject M(3)) according to the physical constitution. The mechanical movement during the panoramic X-ray imaging can be simplified by performing the panoramic X-ray imaging without vertically displacing the X-ray detecting unit 44. The X-ray detecting unit 44 is vertically displaced to perform the panoramic X-ray imaging, so that the X-ray detecting unit 44 is prevented from contacting with the shoulder S.

In the imaging subject M(3), the panoramic X-ray imaging may be performed by turning the X-ray detecting unit 44 at the constant height position where the X-ray detecting unit 44 does not contact with the shoulder S in the lateral of the head P.

It is considered that the panoramic X-ray imaging is performed while the X-ray detecting unit 44 is turned along the second turning orbit R2.

Figure 23:
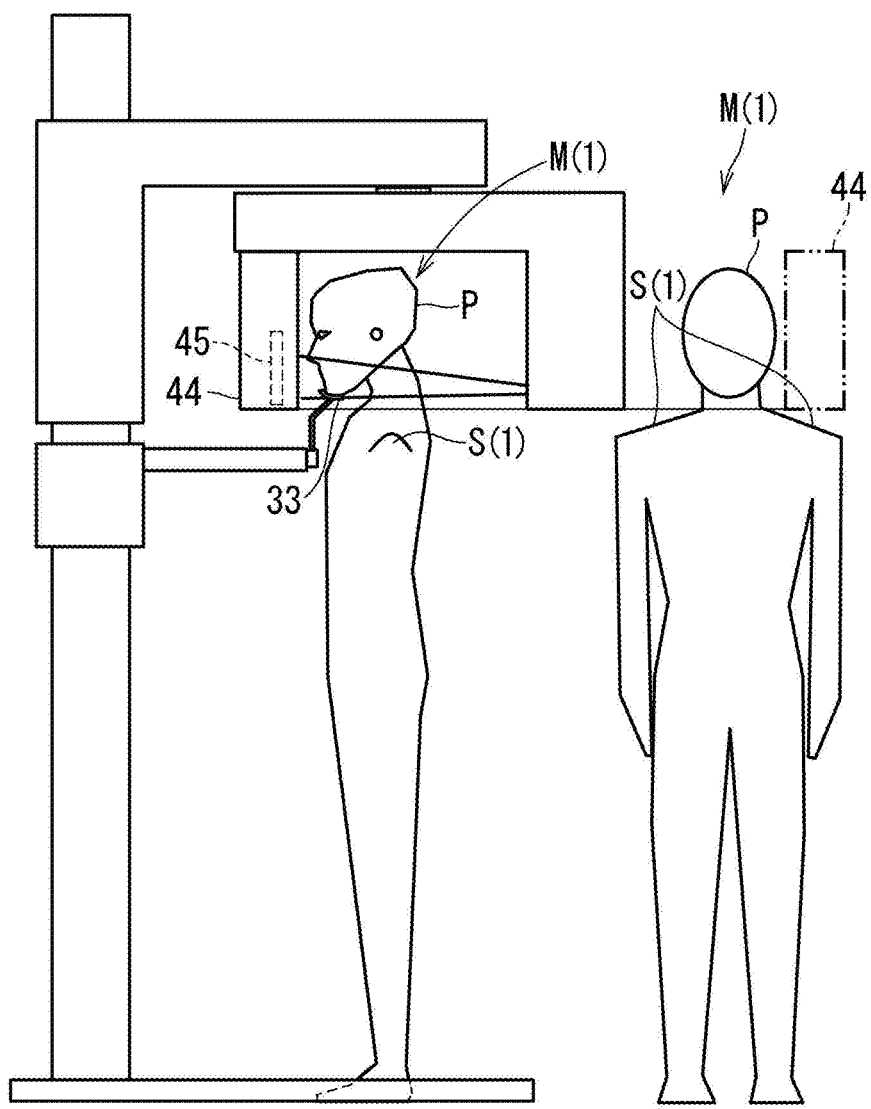
FIG. 23 is an explanatory view illustrating a positional relationship between the X-ray detecting unit and the housing with respect to the imaging subject during the panoramic imaging by the second turning orbit.

FIG. 23 illustrates the case of targeting the imaging subject M(1). The X-ray detecting unit 44 passes through the position closer to the head P in the lateral of the head P than in the case of FIG. 20. When the shoulder S(1) is located below the jaw chip or the like at this position, there is a possibility that the X-ray detecting unit 44 does not contact with the shoulder S(1) even at the lateral position of the head P through which the X-ray detecting unit 44 passes. In this case, the panoramic X-ray imaging can be performed by turning the X-ray detecting unit 44 around the head P without vertically displacing the X-ray detecting unit 44.

However, it is assumed that the case where the passing position of the X-ray detecting unit 44 in the lateral of the head P is extremely close to the upper surface of the shoulder S(1). In such a case, there may be the case where preferably the X-ray detecting unit 44 and the housing are displaced upward in the lateral of the head P in preparation for generation of the contact state caused by the slight movement of the imaging subject M(1). The upper surface of the shoulder S(1) has a shape that goes upward toward the head P. For this reason, the X-ray detecting unit 44 easily comes into contact with the shoulder S(1) as the position of the lateral portion of the head P in the second turning orbit R2 is closer to the head P. For this reason, depending on the set second turning orbit R2, it may be preferable to displace the X-ray detecting unit 44 upward in the lateral of the head P.

Figure 24:
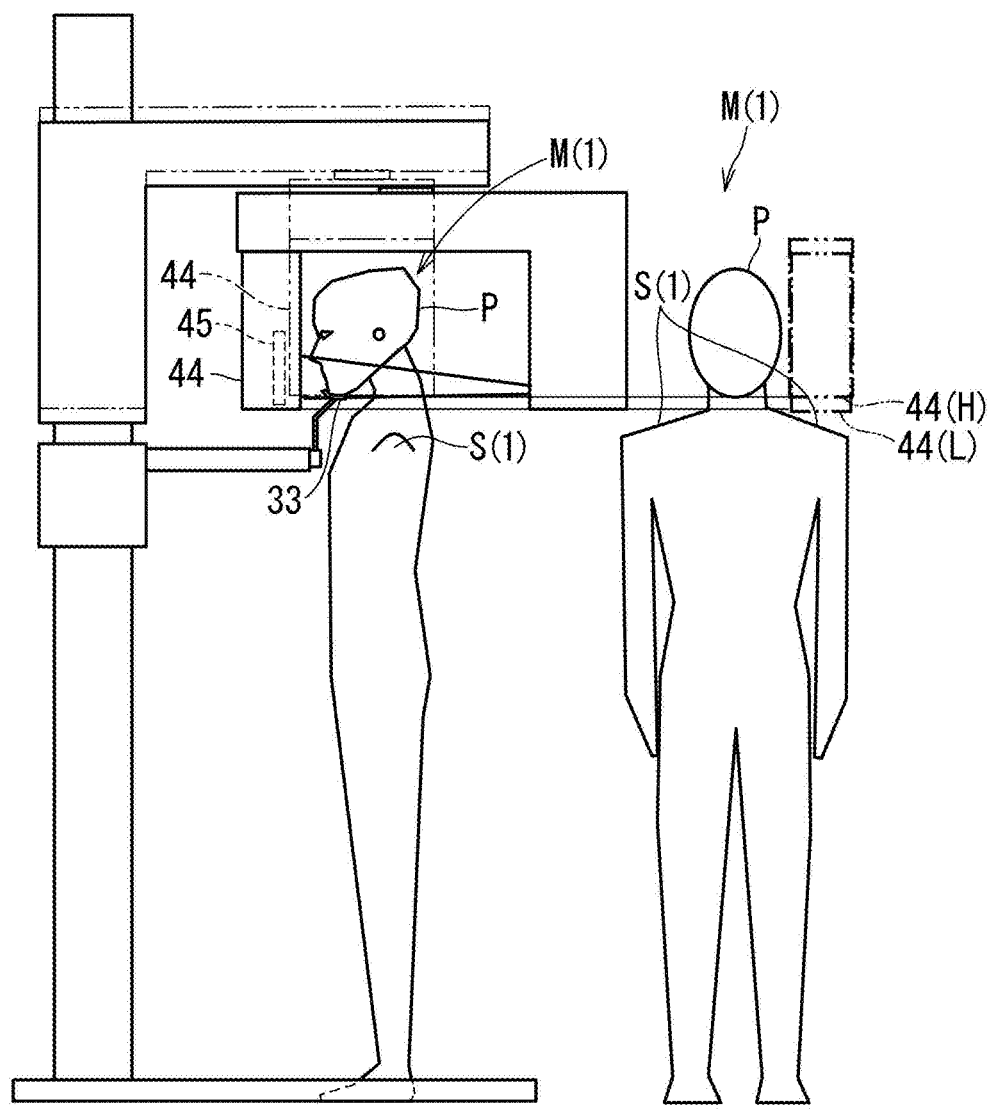
FIG. 24 is an explanatory view illustrating the positional relationship between the X-ray detecting unit and the housing with respect to the imaging subject during the panoramic imaging by the second turning orbit.

In such a case, similarly to the X-ray detecting unit 44(H) in FIG. 24, the X-ray detecting unit 44 may be vertically displaced to perform the panoramic X-ray imaging such that the X-ray detecting unit 44 becomes lower in front of the head P and becomes higher in the lateral of the head P.

Figure 25:
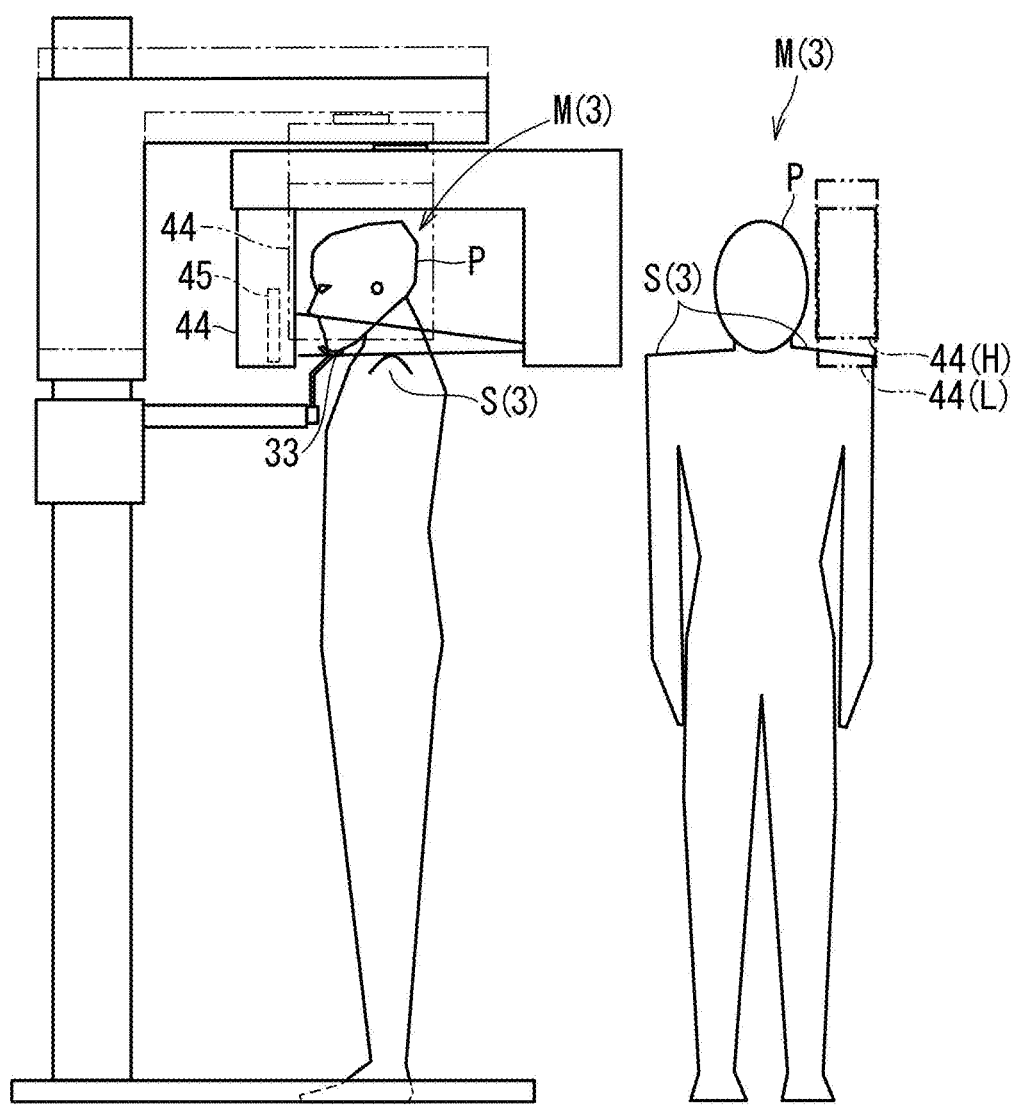
FIG. 25 is an explanatory view illustrating a positional relationship between the X-ray detecting unit and the housing with respect to the imaging subject during the panoramic imaging with the second turning orbit.

When the imaging subject M(3) is targeted, as illustrated in FIG. 25, the X-ray detecting unit 44 passes through the position near the lateral of the head P. When the imaging subject M(3) has the physical constitution such as the square shoulder, the height of the shoulder S(3) near the lateral of the head P according to the second turning orbit R2 is closer to the height of the jaw chip or the like of the head P than the case of the imaging subject M(1). For this reason, the X-ray detecting unit 44 easily comes into contact with the shoulder S(3) in the lateral of the head P (see the X-ray detecting unit 44(L) in FIG. 24).

The vertical displacement pattern is set as described in steps S24, S25, and the X-ray detecting unit 44 is vertically displaced so as to become lower in front of the head P and become higher in the lateral of the head P (see the X-ray detecting unit 44(H)) as described in step S27. Consequently, the X-ray detecting unit 44 can be turned along the second turning orbit R2 while avoiding the contact of the X-ray detecting unit 44 with the shoulder S. Consequently, the panoramic X-ray image in which the front lower end of the dental arch Arc is imaged while avoiding the contact of the X-ray detecting unit 44 with the shoulder S(3) can be generated.

In this way, the X-ray detecting unit 44 is vertically displaced, particularly vertically displaced so as to become higher in the lateral of the head P and become lower in front of the head P, so that the panoramic X-ray image in which the lower portion of the front end of the dental arch Arc is imaged can be obtained while the X-ray detecting unit 44 avoids coming into contact with the shoulder S.

Normally the upper surface of the shoulder S is shaped upward toward the head P, so that the X-ray detecting unit 44 easily comes into contact with the shoulder S when the X-ray detecting unit 44 turns along the second turning orbit R2 rather than the first turning orbit R1. For this reason, the X-ray detecting unit 44 may be vertically displaced when the X-ray detecting unit 44 turns along the second turning orbit R2. The second turning orbit R2 in this case is an example of the turning elevation orbit REL in which the displacement amount of the movement in the vertical direction of the X-ray detecting unit 44 during the panoramic X-ray imaging is larger than zero.

When the second turning orbit R2 can be selected or adjusted, the X-ray detecting unit 44 may be vertically displaced when the orbit close to the head P is selected or adjusted as the second turning orbit R2. When the orbit closer to the head P is selected or adjusted as the second turning orbit R2, the vertical displacement amount of the X-ray detecting unit 44 may be increased. For example, as initial setting values of both the first turning orbit R1 and the second turning orbit R2, the vertical displacement amount of the initial setting of the second turning orbit R2 is set to be larger than the vertical displacement amount of the initial setting of the first turning orbit R1.

The X-ray detecting unit 44 may be vertically displaced in both the first turning orbit R1 and the second turning orbit R2. In this case, the vertical displacement amount of the X-ray detecting unit 44 may be set to be larger in the second turning orbit R2 than in the first turning orbit R1. Similarly to the previous stage, for example, as initial setting values of both the first turning orbit R1 and the second turning orbit R2, the vertical displacement amount of the initial setting of the second turning orbit R2 is set to be larger than the vertical displacement amount of the initial setting of the first turning orbit R1. The vertical displacement amount of the second turning orbit R2 may be automatically set according to the vertical displacement amount of the first turning orbit R1. In this case, for example, it is conceivable to set the vertical displacement amount obtained by multiplying the vertical displacement amount of the first turning orbit R1 by a multiple of a predetermined magnification as the vertical displacement amount of the second turning orbit R2.

When the first turning orbit R1 and the second turning orbit R2 are compared and described in relation to the same imaging subject M, the X-ray detecting unit 44 can move without contacting with the imaging subject M because other human body regions that become a contact object do not exist in the front lower portion of the head P when the X-ray detecting unit 44 passes through the front of the head P along the first turning orbit R1. Even when passing through the lateral of the head P along the first turning orbit the X-ray detecting unit 44 passes through a spot laterally away from the surface of the head P as compared with the case where the X-ray detecting unit 44 moves along the second turning orbit R2. Usually, the upper surface of the shoulder S has the shape that goes downward with increasing distance from the head P. For this reason, the upper surface of the shoulder S is also located on the lower side because the X-ray detecting unit 44 is laterally away from the head P, and the upper surface of the shoulder S is hardly in contact with the shoulder S.

When turning along the second turning orbit R2, the X-ray detecting unit 44 can move without contacting with the imaging subject M similarly to the above description because other human body region that becomes the contact object does not exist in the front lower portion of the head P when the X-ray detecting unit 44 passes through the front of the head P. When passing through the lateral of the head P, the X-ray detecting unit 44 passes through the position closer to the surface of the head P as compared with the case where the X-ray detecting unit 44 moves along the first turning orbit R1. Normally, the upper surface of the shoulder S has the shape that goes upward toward the head P. Thus, the X-ray detecting unit 44 easily comes into contact with the shoulder S as the X-ray detecting unit 44 approaches the head P.

In the head P, there is an individual difference in the positional relationship between the dental arch Arc to be subjected to the panoramic X-ray imaging and the shoulder S. For example, when the imaging subject M has the square shoulder and a short neck, because the difference in the vertical position of the surface of the shoulder S with respect to the height position of the dental arch Arc is small, it is considered that the X-ray detecting unit 44 easily comes into contact with the shoulder S. Furthermore, for example, when the imaging subject M has a sloping shoulder and a long neck, the difference in the vertical position of the surface of the shoulder S with respect to the height position of the dental arch Arc is larger than the above case. For this reason, it is considered that the X-ray detecting unit 44 hardly comes into contact with the shoulder S.

Consequently, it is considered that the panoramic X-ray imaging by the first turning orbit R1 can be performed on the imaging subject M having most of the physical constitution, whereas an executable case and an executable case are easily generated depending on the physical constitution for the panoramic X-ray imaging by the second turning orbit R2.

As a measure of the user, either the measure in which the panoramic X-ray imaging is performed without vertically displacing the X-ray detecting unit 44 or the measure in which the panoramic X-ray imaging is performed by vertically displacing the X-ray detecting unit 44 can be adopted.

In the former case, when setting the second turning orbit R2 by observing the physical constitution of the imaging subject M or actually turning the X-ray detecting unit 44 on a trial basis, the user determines whether the X-ray detecting unit 44 comes into contact with the imaging subject M. Alternatively, whether the second turning orbit R2 is applicable may be determined based on the output result of the physical constitution detecting unit (imaging apparatus 22). When the second turning orbit R2 is applicable, the panoramic X-ray imaging can be performed using the second turning orbit R2 by setting the second turning orbit R2 (see steps S2, S3). When the second turning orbit R2 is hardly applicable, the panoramic X-ray imaging is performed using the first turning orbit R1.

In the latter case, the user sets the turning orbit in which the X-ray detecting unit 44 can be brought close to the head P, for example, the second turning orbit R2 within the range in which the contact with the head P can be avoided. Under the condition that the second turning orbit R2 is set, the vertical displacement pattern is set in order to avoid the contact with the shoulder S. The X-ray detecting unit 44 is vertically displaced according to the set vertical displacement pattern to perform the panoramic X-ray imaging.

In the case where it is difficult to avoid the contact of the X-ray detecting unit 44 with the shoulder S when the turning orbit of the X-ray detecting unit 44 is too close to the head P, the user may set the turning orbit and the vertical displacement amount such that the approach degree of the X-ray detecting unit 44 to the head P and the vertical displacement amount of the X-ray detecting unit 44 are well balanced.

The X-ray imaging apparatus 200 can further improve the resolution of the panoramic X-ray image by turning the X-ray detecting unit 44 along the second turning orbit R2 closer to the head P.

In general, in the second turning orbit R2 closer to the head P, the vertical displacement of the X-ray detecting unit 44 is more required than the first turning orbit R1, and the vertical displacement amount tends to be increased. It is easy to obtain the appropriate panoramic X-ray image by setting the turning orbit of the X-ray detecting unit 44 and the vertical displacement amount of the X-ray detecting unit 44 in consideration of the case, the physical constitution, the importance of the high resolution, the allowable range of the vertical displacement in the panoramic X-ray image, and the like of the imaging subject M.

In addition, when at least one of the first turning orbit R1 and the second turning orbit R2, particularly the second turning orbit R2 is an orbit close to within 10 cm from the surface of the head P in front of the head P, the resolution of the panoramic X-ray image, particularly the resolution in the front tooth region Pa can be improved.

In addition, when at least one of the first turning orbit R1 and the second turning orbit R2, particularly the second turning orbit R2 is an orbit that approaches within 10 cm from the surface of the head P in front of the head P over the entire region, the resolution of the panoramic X-ray image can be further improved over the entire region.

In addition, when the orbit in which the partial orbit in the front range of the front tooth region Pa comes closer to the surface of the head P than the partial orbit in other ranges is set as the second turning orbit R2, the X-ray detecting unit 44 can be brought close to the front tooth region Pa, and the resolution of the panoramic X-ray image representing the front tooth region can be further improved.

When the orbit in which the distance to the surface of the head P in the lateral of the head P is larger than the distance to the surface of the head P in front of the head P is set as the second turning orbit R2, the X-ray detecting unit 44 easily turns while avoiding the contact with the shoulder S. Similarly, when the orbit in which the distance to the surface of the head P in the lateral of the head P is larger than the distance to the surface of the head P in front of the head P is set as the first turning orbit R1, the X-ray detecting unit 44 easily turns while avoiding the contact with the shoulder S.

<Modifications>

In the second preferred embodiment, the example in which the second turning orbit information 204*c* defining the second turning orbit R2 is previously set and stored in the storage 104 has been described. The imaging controller 202 may set the second turning orbit R2 for each individual according to the physical constitution data of the individual of the imaging subject M.

Figure 26:
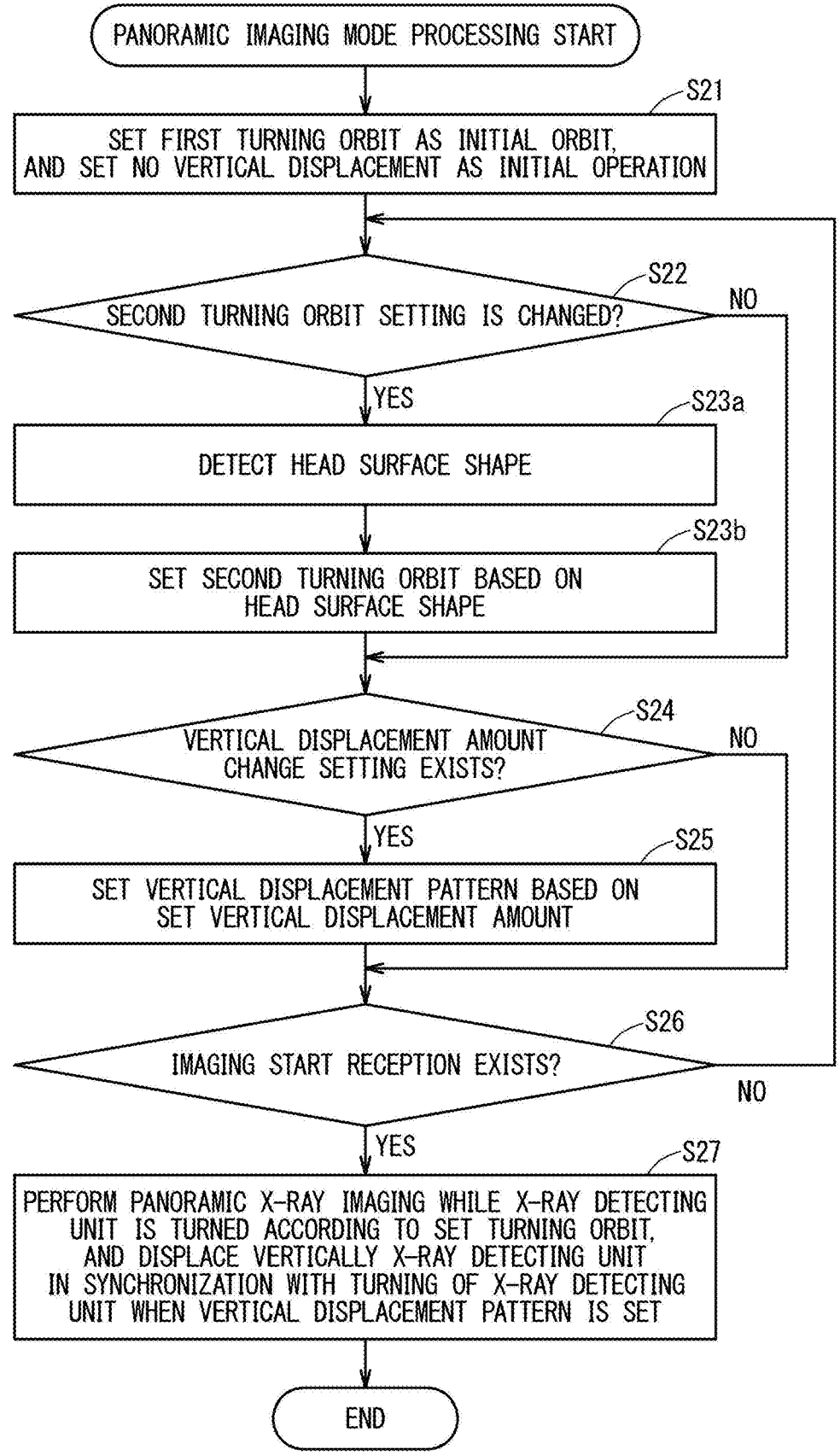
FIG. 26 is a flowchart illustrating an example of processing performed by a turning controller according to a modification.

FIG. 26 is a flowchart illustrating an example of processing performed by the imaging controller 202 according to a modification. Differences of this flowchart from the flowchart in FIG. 18 will be mainly described. In this flowchart, step S23 in FIG. 18 is changed to steps S23*a* and S23*b*.

In steps S23*a* and S23*b*, the imaging apparatus 22 is used as a head surface shape detecting unit that detects the surface shape of the head P, and the second turning orbit R2 is set according to the detection result of the imaging apparatus 22.

That is, in step S23*a*, the head P and the shoulder S that are held by the subject holding unit 32 are imaged by the imaging apparatus 22. For example, the X-ray detecting unit 44 may be turned along the first turning orbit R1 that hardly contacts with the imaging subject M, and the image data obtained by imaging the head P from a plurality of spot directions may be used as the detection result. The imaging data may include the shoulder S. Because the image data includes the surface shape of the head P, the image data is an example of the physical constitution data including the physical constitution of the head P of the imaging subject M.

In subsequent step S23b, the second turning orbit R2 is set based on the surface shape of the head P.

Figure 27:
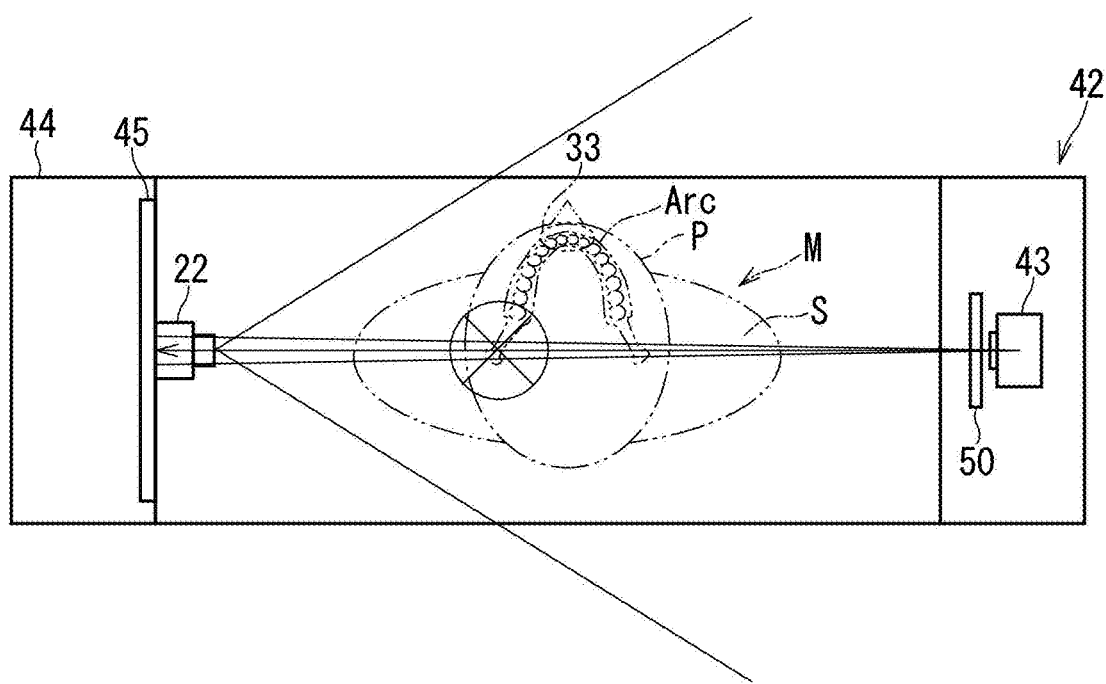
FIG. 27 is an explanatory view illustrating an example of head surface shape data representing a surface shape of a head with respect to an X-ray detecting unit.

A more specific example of steps S23a and S23b will be described. First, the positional relationship of the imaging apparatus 22 with respect to the turning arm 40 and the X-ray detecting unit 44 can be known information. For this reason, as illustrated in FIG. 27, the head surface shape data indicating the surface shape of the head P with respect to the X-ray detecting unit 44 can be generated based on the image data obtained by imaging the head P. The image data obtained by imaging the head P may be image data obtained by imaging the head P from a plurality of directions. For example, a combination of image data obtained by imaging the head P from the front or the rear and image data obtained by imaging the head P from the left side or the right side can be used. The horizontal section of the head P represented in the head surface shape data may be a horizontal section passing through the most widening portion of the horizontal section of the head P, for example, the tip of the nose. In the head surface shape data, the second turning orbit R2 in which the X-ray detecting unit 44 hardly contacts with the head P can be set. For example, a passing point passing through a predetermined distance less than or equal to 10 cm from the front of the surface of the head P may be set, and a curve passing through the passing point may be set as the second turning orbit R2. For example, a plurality of passing points passing through a predetermined distance less than or equal to 10 cm from the surface of the head P may be set at a plurality of positions around the dental arch Arc in the head P, and a curve passing through the plurality of passing points may be set as the second turning orbit R2. In addition, for example, a plurality of candidate orbits of the second turning orbit R2 may be previously set and stored in the storage 104, and one of the plurality of candidate orbits in which the X-ray detecting unit 44 can pass through the closest point to the surface of the head P without contacting with the head P may be set as the second turning orbit R2 based on the head surface shape data. For example, the initial candidate orbit of the second turning orbit R2 is previously set and stored in the storage 104, and the initial candidate orbit is sequentially increased or decreased (for example, the orbit passing through the position close to or the position far from the head P by a predetermined distance (for example, 1 cm) with respect to the initial candidate orbit is sequentially set), the orbit in which the X-ray detecting unit 44 can pass through the closest point to the surface of the head P without contacting with the head P is specified based on the head surface shape data, and the orbit may be set as the second turning orbit R2.

Although the first turning orbit R1 may also be set according to the detection result of the imaging apparatus 22, the second turning orbit R2 is set based on at least the surface shape of the head P because the priority of determining the second turning orbit R2 close to the head surface by the actual measurement using the highly reliable head surface shape detecting unit is high.

The setting of the second turning orbit R2 according to the individual of the imaging subject M may be performed based on the X-ray image data obtained by previously imaging the imaging subject M, for example, the cephalogram imaging data. The left and right regions of the head P are imaged in the front cephalographic imaging data and the front region of the head P is imaged in the side cephalographic imaging data, so that the positions of the left and right regions and the front region of the head P can be determined based on the cephalographic imaging data to set the second turning orbit R2 in the similar manner as described above. The cephalographic data is also an example of the physical constitution data. The surface shape of the head P is also imaged in the cephalographic imaging data, so that the X-ray detector 45 that images the cephalographic imaging data can be used as an example of the head surface shape detecting unit.

In both the visible light image and the X-ray image, the surface or the boundary of the head P can be automatically extracted by performing the image recognition processing such as the edge extraction image processing. However, the surface or the boundary of the head P may be designated by designation of a pointer by the user or the like.

The apparatus that detects the surface shape of the head P as the head surface shape detecting unit may be the mobile terminal device 300 having the imaging apparatus such as a smartphone or a tablet terminal apparatus (see FIG. 2). The mobile terminal device 300 performs the imaging of the image in which the head P and the reference region in the X-ray imaging apparatus 20 are imaged, and performs image processing or the like based on the imaging image, so that the surface position of the head P in the X-ray imaging apparatus 20 can be recognized. Thus, similarly to the above, the second turning orbit R2 and the like can be set for each individual.

Furthermore, for example, the visible light sensor or the laser sensor that detects the surface of the head P, in particular, the front region and the lateral region may be incorporated in the turning arm 40, and the surface position of the head P, in particular, the front region and the lateral region may be detected based on the output of the sensor. The data including these detection results is an example of the physical constitution data. The surface position, in particular, the front region and the lateral of the head P with respect to the turning arm 40 and the X-ray detecting unit 44 are specified based on the detection results, so that the second turning orbit R2 can be set similarly to the above.

The second turning orbit R2 may be set for each individual by user setting. For example, a plurality of candidate orbits of the second turning orbit R2 may be previously set and stored in the storage 104, the user inputs the distinction between the adult size and the child size or the distinction among the S size, the M size, and the L size, so that the candidate orbit corresponding to the input size may be set as the second turning orbit R2.

When the shoulder S of the imaging subject M is higher than the standard position, the second turning orbit R2 may be set so as to make a more detour in the lateral of the head P.

When coming into contact with the shoulder S in turning on the second turning orbit R2, the X-ray detecting unit 44 is vertically displaced during the turning as described above.

According to this modification, the imaging controller 202 can set the second turning orbit R2 for each individual according to the physical constitution data of the individual of the imaging subject M. Consequently, according to the physical constitution of the individual, the X-ray detecting unit 44 is brought as close to the head P as possible to perform panoramic X-ray imaging, and the high-resolution panoramic X-ray image can be obtained.

In this case, the second turning orbit R2 can be easily set by setting the second turning orbit R2 based on the detection result of the head surface shape detecting unit such as the imaging apparatus 22. In addition, the second turning orbit R2 passing immediately near the surface of the head P can be easily set based on the detection result.

The resolution of the panoramic X-ray image is further improved by setting the orbit passing through the position within 10 cm from the surface of the head P as the second turning orbit R2.

In the modification, the example in which the second turning orbit R2 is set for each individual has been described. The first turning orbit R1 that turns at a position farther from the head P than the first turning orbit R1 may also be set for each individual similarly to the above.

The user (operator) may arbitrarily set the turning orbit R, or the user may set a new turning orbit R by changing the turning orbit R based on the turning orbit information 204 stored in the storage 104. In this case, when the X-ray detecting unit 44 faces the lateral of the head P, the X-ray detection orbit may be set such that the additional displacement amount of the vertical movement to the X-ray detecting unit 44 becomes larger as the turning orbit R with respect to the lateral surface of the head P of the X-ray detecting unit 44 approaches the lateral surface of the head P.

In the setting of the X-ray detection orbit of the panoramic X-ray imaging of the X-ray imaging apparatuses 20, 200, the relationship of the position of the shoulder S with respect to the head P, particularly, the position in the Z direction, namely, the height relationship may be adaptable for each physical constitution of the individual imaging subject M. In order to cope with this, the X-ray imaging apparatuses 20, 200 may be configured such that the addition displacement amount of the vertical movement to the X-ray detecting unit 44 by the vertical drive unit 82 can be changed according to the position of the shoulder S with respect to the head P for each physical constitution of the individual imaging subject M.

The additional displacement amount of the vertical movement may be changed according to the reception of the user input operation according to the position of the shoulder S with respect to the head P for each physical constitution of the individual imaging subject M or the detection result by the imaging apparatus 22 according to the position of the shoulder S with respect to the head P for each physical constitution of the individual imaging subject M. For example, the input operation is received through the imaging setting receiving unit 110a.

{Modifications}

The configurations described in the above embodiments and the modifications can appropriately be combined as long as they are not inconsistent with each other.

Thus, the present specification and the drawings disclose the following aspects.

According to a first aspect, a panoramic X-ray imaging apparatus including: an X-ray generating unit that includes an X-ray generator; an X-ray detecting unit that includes an X-ray detector; a support that supports the X-ray generating unit and the X-ray detecting unit such that the X-ray generating unit and the X-ray detecting unit are opposite to each other; a drive mechanism that turns at least the X-ray generating unit and the X-ray detecting unit by driving the support; a displacement mechanism that adds movement including a displacement component in a direction different from the turning to the X-ray detecting unit; a subject holding unit that holds an imaging subject; and a turning controller that controls drive of the support by the drive mechanism and addition of movement to the X-ray detecting unit by the displacement mechanism such that panoramic X-ray imaging is performed by turning around a head of the imaging subject while the head of the imaging subject held by the subject holding unit is positioned between the X-ray generating unit and the X-ray detecting unit, wherein the turning controller controls the drive mechanism and the displacement mechanism so as to add the movement avoiding the contact with the shoulder of the imaging subject to the X-ray detecting unit during the turning of the X-ray generating unit and the X-ray detecting unit by the drive mechanism during the panoramic X-ray imaging.

According to the panoramic X-ray imaging apparatus, when the X-ray generating unit and the X-ray detecting unit turn around the head located between the X-ray generating unit and the X-ray detecting unit, the movement avoiding the contact with the shoulder of the imaging subject is added to the X-ray detecting unit. Thus, the X-ray detecting unit can be brought close to the head of the imaging subject as much as possible while the shoulder hitting of the X-ray detecting unit is prevented. When the X-ray detector can be brought close to the head of the imaging subject as much as possible, the resolution of the panoramic X-ray image can be improved.

A second aspect is the panorama X-ray photographing apparatus according to the first aspect, the displacement mechanism includes a vertical displacement mechanism that vertically displaces the X-ray detecting unit with respect to the head, and the turning controller applies vertical movement to the X-ray detecting unit by the vertical displacement mechanism such that a lower end position of the X-ray detecting unit passing through a lateral of the head is located higher than a lower end position of the X-ray detecting unit passing through a front of the head.

In this case, when the X-ray detector passes through the front of the head, the X-ray detector hardly comes into contact with the human body even when the X-ray detector is located on the lower side, so that the X-ray detector can be brought close to the head. Because the X-ray detector is located on the upper side when the X-ray detector passes through the lateral of the head, the X-ray detector can be brought close to the head while the X-ray detector is prevented from contacting with the shoulder. Thus, the resolution of the panoramic X-ray image can be further improved while the X-ray detector is prevented from hitting the shoulder.

A third aspect is the panorama X-ray photographing apparatus according to the second aspect, and the vertical displacement mechanism is a mechanism that vertically moves the support with respect to the head.

Thus, the X-ray generating unit and the X-ray detecting unit can be vertically moved by vertically moving the support.

A fourth aspect is the panorama X-ray imaging apparatus according to the second or third aspect further includes a physical constitution detecting unit that detects a physical constitution of the imaging subject, and the turning controller controls drive of the vertical displacement mechanism according to a detection result of the physical constitution detecting unit.

According to the fourth aspect, the operation of the vertical displacement mechanism can be controlled according to the physical constitution of the imaging subject, and the shoulder hitting can be prevented.

A fifth aspect is the panoramic X-ray photographing apparatus according to the fourth aspect, and the turning controller determines whether the vertical movement avoiding the contact with the shoulder is required according to the detection result of the physical constitution detecting unit, and adds the vertical movement to the X-ray detecting unit by the vertical displacement mechanism when the vertical movement is required.

According to the fifth aspect, the panoramic X-ray image imaged without vertically displacing the X-ray detector is obtained depending on the physical constitution.

A sixth aspect is the panorama X-ray photographing apparatus according to the fourth or fifth aspect, and the turning controller determines a vertical displacement amount avoiding contact with the shoulder according to the detection result of the physical constitution detecting unit, and adds the vertical movement to the X-ray detecting unit by the vertical displacement mechanism according to the determined vertical displacement amount.

According to the sixth aspect, the panoramic X-ray imaging is performed with an appropriate vertical displacement amount according to the physical constitution.

A seventh aspect is the panorama X-ray photographing apparatus according to any one of the first to sixth aspects, and the drive mechanism includes a turning mechanism that turns the X-ray generating unit and the X-ray detecting unit and a two-dimensional moving mechanism that moves the X-ray generating unit and the X-ray detecting unit in a two-dimensional direction along a turning plane of the X-ray generating unit and the X-ray detecting unit by the turning mechanism.

According to the seventh aspect, when the X-ray generating unit and the X-ray detecting unit are turned by the turning mechanism, the two-dimensional moving mechanism moves the X-ray generating unit and the X-ray detecting unit in the two-dimensional direction along the turning surface, so that the turning orbits of the X-ray generating unit and the X-ray detecting unit can be changed.

An eighth aspect is the panorama X-ray photographing apparatus according to the seventh aspect, the turning mechanism is a turning mechanism that turns the support about a turning axis of a turning shaft, and the two-dimensional moving mechanism is a turning axis moving mechanism that moves the turning shaft in a direction intersecting an axial direction of the turning shaft.

According to the eighth aspect, the turning axis moving mechanism moves the turning shaft in synchronization with the turning of the support by the turning mechanism, and the support performs the combined motion, so that the turning orbits of the X-ray generating unit and the X-ray detecting unit can be changed.

A ninth aspect is the panorama X-ray imaging apparatus according to the seventh or eighth aspect, the turning controller is configured to be able to set a first turning orbit and a second turning orbit of the X-ray detecting unit in the panoramic X-ray imaging, and the second turning orbit is an orbit closer to a surface of the head than the first turning orbit in front of the head.

Consequently, the resolution of the panoramic X-ray image can further be improved by turning the X-ray detector along the second turning orbit brought closer to the head.

A tenth aspect is the panoramic X-ray imaging apparatus according to any one of the first to ninth aspects, and the turning controller sets the turning orbit of the X-ray detecting unit in the panoramic X-ray imaging such that the turning orbit passes through a position within 10 cm from the surface of the head in front of the head.

Consequently, the resolution of the panoramic X-ray image can further be improved by turning the X-ray detector along the turning orbit brought closer to the head within 10 cm from the surface of the head in front of the head.

An eleventh aspect is the panorama X-ray imaging apparatus according to the 10 aspect, and the turning controller sets the turning orbit of the X-ray detecting unit in the panoramic X-ray imaging such that the turning orbit passes through the position within 10 cm from the surface of the head over the whole head.

Thus, the X-ray detector can be brought close to within 10 cm from the surface of the head to obtain a clearer panoramic X-ray image.

The first turning orbit R1 is illustrated in FIG. 17A, and the first turning orbit R1 in FIG. 17A and the second turning orbit R2 in FIG. 9 may be selectively switched. The second turning orbit R2 is set to an orbit closer to the head surface than the first turning orbit R1 in front of the head P (at least in front of the center in the left-right direction of the head P). Thus, the X-ray detecting unit 44 turning on the second turning orbit R2 can detect the X-ray closer to the front tooth region of the dental arch Arc that is the region of interest.

In front of the head P, the approach degree of the X-ray detecting unit 44 to the head surface of the second turning orbit R2 is higher than that of the first turning orbit R1. In addition, the second turning orbit R2 has a higher front proximity ratio and a lower lateral proximity ratio than the first turning orbit R1. Under this condition, the height difference FS2 of the second turning orbit R2 may be set larger than the height difference FS1 of the first turning orbit R1. Thus, for example, even in the case where a degree of square shoulder of the imaging subject is stronger, it is possible to cope with the case.

In addition, in the configuration in which the first turning orbit R1 in FIG. 9 and the second turning orbit R2 in FIG. 26 are selectively switched, still another second turning orbit R2 may also be selectable. For example, the still another second turning orbit R2 is the second turning orbit R2 in FIG. 17B, and the height difference of the second turning orbit R2 in FIG. 17B may be set to be larger than other turning orbits. Thus, valuation of the approach to the head P of the imaging subject can be enhanced.

The approach degree of the X-ray detecting unit 44 to the head surface may be set such that at least a part of the entire region of the second turning orbit R2 is larger than the first turning orbit R1, and the remaining region is equal to the first turning orbit or smaller than the first turning orbit.

The above description is illustrative in all aspects, and the present invention is not limited thereto. Innumerable modifications not illustrated can be envisaged without departing from the scope of the present invention.

While the invention has been shown and described in detail, the foregoing description is in all aspects illustrative and not restrictive. It is therefore understood that numerous modifications and variations can be devised without departing from the scope of the invention.

What is claimed is:

1. A panoramic X-ray imaging apparatus comprising:
   a first housing that accommodates an X-ray generator;
   a second housing that accommodates an X-ray detector;
   a support that supports the first housing and the second housing such that the X-ray generator and the X-ray detector are opposite to each other;
   a shaft located between the X-ray generator and the X-ray detector;
   a first motor that turns the support around the shaft;
   a second motor that provides movement to the second housing, said movement including a displacement in a direction different from the turning;
   a subject holder that holds an imaging subject; and a processor that controls drive of the support by the first motor and addition of movement to the second housing by the second motor such that panoramic X-ray imaging is performed by turning around a head of the imaging subject while the head of the imaging subject held by the subject holder is positioned between the X-ray generator and the X-ray detector, wherein the processor controls the first motor and the second motor so as to add the movement avoiding the contact with the shoulder of the imaging subject to the second housing during the turning of the X-ray generator and the X-ray detector by the first motor during the panoramic X-ray imaging.

2. The panoramic X-ray imaging apparatus according to claim 1, wherein the second motor vertically displaces the second housing with respect to the head, and the processor applies vertical movement to the second housing by the second motor such that a lower end position of the second housing passing through a lateral of the head is located higher than a lower end position of the second housing passing through a front of the head.

3. The panoramic X-ray imaging apparatus according to claim 2, wherein the second motor vertically moves the support with respect to the head.

4. The panoramic X-ray imaging apparatus according to claim 2, further comprising an imaging apparatus that detects a physical constitution of the imaging subject, wherein the processor controls drive of the second motor according to a detection result of the imaging apparatus.

5. The panoramic X-ray imaging apparatus according to claim 4, wherein the processor determines whether the vertical movement avoiding the contact with the shoulder is required according to the detection result of the imaging apparatus, and adds the vertical movement to the second housing by the second motor when the vertical movement is required.

6. The panoramic X-ray imaging apparatus according to claim 4, wherein the processor determines a vertical displacement amount avoiding contact with the shoulder according to the detection result of the imaging apparatus, and provides the vertical movement to the second housing by the second motor according to the determined vertical displacement amount.

7. The panoramic X-ray imaging apparatus according to claim 1, further comprising a two-dimensional moving motor that provides power to move the shaft in a two-dimensional direction along a turning plane of the first housing and the second housing by the first motor.

8. The panoramic X-ray imaging apparatus according to claim 7, further comprising a XY-table that includes an X direction movable table and a Y direction movable table, the two-dimensional moving motor moves the X direction movable table and the Y direction movable table to moves the turning shaft in a direction intersecting an axial direction of the turning axis.

9. The panoramic X-ray imaging apparatus according to claim 7, wherein the processor is configured to be able to set a first turning orbit and a second turning orbit of the second housing in the panoramic X-ray imaging, and the second turning orbit is an orbit closer to a surface of the head than the first turning orbit in front of the head.

10. The panoramic X-ray imaging apparatus according to claim 1, wherein the processor sets a turning orbit of the second housing in the panoramic X-ray imaging such that the turning orbit passes through a position within 10 cm from the surface of the head in front of the head.

11. The panoramic X-ray imaging apparatus according to claim 10, wherein the processor sets the turning orbit of the second housing in the panoramic X-ray imaging such that the turning orbit passes through the position within 10 cm from the surface of the head over the whole head.

12. A panoramic X-ray imaging apparatus comprising:

a generate means for generating X-ray;

a detect means for detecting X-ray;

a support means for supporting the generate means and the detect means such that the generate means and the detect means are opposite to each other;

a drive means for turning at least the generate means and the X-ray detect means by driving the support means;

a displacement means provides movement including a displacement component in a direction different from the turning to the detect means;

a subject hold means for holding an imaging subject; and a turning control means for controlling drive of the support means by the drive means and addition of movement to the detect means by the displacement means such that panoramic X-ray imaging is performed by turning around a head of the imaging subject while the head of the imaging subject held by the subject hold means is positioned between the generate means and the detect means, wherein the turning control means controls the drive means and the displacement means so as to add the movement avoiding the contact with the shoulder of the imaging subject to the detect means during the turning of the generate means and the detect means by the drive means during the panoramic X-ray imaging.

* * * * *